US012059353B2

United States Patent
Vogt et al.

(10) Patent No.: US 12,059,353 B2
(45) Date of Patent: Aug. 13, 2024

(54) DEVICE AND METHOD FOR PRODUCING KNEE SPACER COMPONENTS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 246 days.

(21) Appl. No.: 17/204,656

(22) Filed: Mar. 17, 2021

(65) Prior Publication Data

US 2021/0290395 A1    Sep. 23, 2021

(30) Foreign Application Priority Data

Mar. 20, 2020   (EP) ..................................... 20164541

(51) Int. Cl.
| | | |
|---|---|---|
| *A61F 2/30* | (2006.01) | |
| *A61F 2/38* | (2006.01) | |
| *A61F 2/46* | (2006.01) | |
| *B29C 43/00* | (2006.01) | |
| *B29C 43/02* | (2006.01) | |
| *B29C 43/36* | (2006.01) | |
| *B29C 45/00* | (2006.01) | |
| *B29C 45/23* | (2006.01) | |
| *B29C 45/26* | (2006.01) | |
| *B29K 33/00* | (2006.01) | |
| *B29L 31/00* | (2006.01) | |

(52) U.S. Cl.
CPC ............ *A61F 2/30942* (2013.01); *A61F 2/38* (2013.01); *A61F 2/4684* (2013.01); *B29C 43/003* (2013.01); *B29C 43/02* (2013.01); *B29C 43/36* (2013.01); *B29C 45/0001* (2013.01); *B29C 45/23* (2013.01); *B29C 45/26* (2013.01); *A61F 2002/30957* (2013.01); *A61F 2310/00353* (2013.01); *B29K 2033/12* (2013.01); *B29L 2031/7532* (2013.01)

(58) Field of Classification Search
CPC ............ A61F 2/30942; B29C 45/0001; B29C 43/003
See application file for complete search history.

(56) References Cited

U.S. PATENT DOCUMENTS

| | | | |
|---|---|---|---|
| 7,789,646 B2 | 9/2010 | Haney et al. | |
| 8,801,983 B2 | 8/2014 | Haney et al. | |
| 8,900,322 B2 | 12/2014 | De Beaubien | |
| 9,433,506 B2 * | 9/2016 | Lomicka | A61F 2/38 |
| 10,071,511 B2 | 9/2018 | Smith et al. | |
| 11,154,343 B2 * | 10/2021 | Vogt | A61L 24/043 |

(Continued)

FOREIGN PATENT DOCUMENTS

| | | |
|---|---|---|
| CN | 201335161 Y  * | 10/2009 |
| DE | 102015104704 B4 | 10/2016 |

(Continued)

*Primary Examiner* — Farah Taufiq
*Assistant Examiner* — Timothy G Hemingway
(74) *Attorney, Agent, or Firm* — Dicke, Billig & Czaja, PLLC

(57) ABSTRACT

The invention relates to a device for producing a knee spacer component by curing bone cement paste. The invention also relates to methods for producing knee spacer components using such a device.

30 Claims, 33 Drawing Sheets

(56) References Cited

U.S. PATENT DOCUMENTS

| | | | |
|---|---|---|---|
| 11,255,463 B2* | 2/2022 | Thurau | ................ F16K 41/046 |
| 2010/0101989 A1 | 4/2010 | Berndt | |
| 2010/0102484 A1 | 4/2010 | Haney et al. | |
| 2013/0187310 A1* | 7/2013 | Vogt | .......................... A61F 2/36 |
| | | | 264/313 |
| 2016/0013094 A1 | 1/2016 | Min | |
| 2020/0009771 A1* | 1/2020 | Smith | ................... A61F 2/4684 |

FOREIGN PATENT DOCUMENTS

| | | | |
|---|---|---|---|
| DE | 202018105406 U1 * | 1/2020 | |
| EP | 2617393 B1 | 7/2015 | |
| EP | 2931180 B1 | 11/2016 | |
| EP | 3143963 B1 | 11/2018 | |
| JP | 2018118056 A | 8/2018 | |
| WO | 20160205077 | 12/2016 | |

* cited by examiner

DEVICE AND METHOD FOR PRODUCING KNEE SPACER COMPONENTS

CROSS-REFERENCE TO RELATED APPLICATIONS

This application claims priority to European Patent Application No. 20164541.3 filed on Mar. 20, 2020, the entire disclosure of which is incorporated by reference herein.

DESCRIPTION

The invention relates to a device for producing a knee spacer component of a knee spacer, i.e. a femoral component or a tibial component, by curing bone cement paste. The knee spacer or tibial component and femoral component are provided as a temporary placeholder in medical applications for temporarily replacing a knee joint or part of a knee joint comprising an articulating surface of the knee joint. The tibial component and femoral component are preferably suitable and provided for temporarily replacing a knee joint. The invention also relates to a method for producing a knee spacer component of a knee spacer, meaning a femoral component or a tibial component, with such a device. The present invention thus provides a device and a method for producing knee spacer components. The device is intended for fabrication of knee spacer components by operating personnel prior to insertion of the knee spacer, i.e. before the actual operation. The term "knee spacer components" is taken to mean the tibial component and femoral component of articulating knee spacers.

Knee joint endoprostheses are implanted in large numbers worldwide. Unfortunately, in a small percentage of cases, knee joint endoprostheses are colonized by microbial microorganisms, in particular Gram-positive bacteria and also Gram-negative bacteria, and to a very small extent by yeasts and fungi. These microbial microorganisms, mainly typical skin microbes such as *Staphylococcus aureus* and *Staphylococcus epidermidis*, may enter a patient's body during a surgical operation (OP). It is also possible for microbial microorganisms to enter joint endoprostheses hematogenically. When joint endoprostheses are colonized by microbial microorganisms, the surrounding bone and soft tissue also become infected and damaged by the microbial microorganisms.

The prior art primarily encompasses two treatment methods for infected joint endoprostheses, one-stage septic revision and two-stage septic revision. In the case of one-stage revision, the infected joint endoprosthesis is removed first, next radical debridement is performed and then a revision joint endoprosthesis is implanted within one OP.

In two-stage septic revisions, the infected knee joint endoprosthesis is initially removed in a first OP, then debridement is performed and thereafter a knee spacer is implanted. A knee spacer has a tibial component and a femoral component and basically replicates the shape and size of the knee joint endoprosthesis. The tibial component has a stem and tibial plateau, wherein the tibial plateau forms a sliding or rolling surface of the knee joint and the stem can be anchored in the tibia. The femoral component has a stem for anchoring in the femur and two condyles for rolling on the tibial plateau. The tibial component and femoral component are anchored with bone cement to the respective bones, i.e. for example in the case of the femoral component to the distal femur or in the femoral canal and in the case of the tibial component with the stem to the proximal tibia or in the tibial canal. The knee spacer remains in the patient for up to several weeks until the inflammation has subsided and clinical inflammation markers have receded. The knee spacer is then removed in a second OP and a revision knee joint endoprosthesis implanted after fresh debridement.

In the case of knee spacer components, antibiotics are added to the cement powder before the actual production of the knee spacer. Using this antibiotically modified bone cement powder, a bone cement paste is then produced by admixing monomer liquid and knee spacer components are cast from this bone cement paste which then cure by polymerization with the assistance of the monomer liquid added to the cement powder. The bone cement paste thus substantially incorporates the antibiotics. The antibiotic particles situated in areas close to the surface are released under the action of bodily fluids, such as wound secretions. Active ingredient release is greatest at the start and then diminishes over the course of several days.

WO 2016/205077 A1 and U.S. Pat. No. 8,900,322 B2 describe knee spacers with an irrigation function. It is further known to use knee spacers provided with antibiotics. Knee spacers may be produced with PMMA bone cement powder, antibiotics and monomer liquid, for example using a spacer mold, as described for example in patents DE 10 2015 104 704 B4, U.S. Pat. No. 7,789,646 B2, U.S. Pat. No. 8,801,983 B2 or EP 2 617 393 B1. On the other hand, it is also conventional to use knee spacers industrially prefabricated from bone cement.

Patent EP 2 931 180 B1 discloses a cement mold for producing a tibial component of a knee spacer which is suitable for release of antibiotics. Patent EP 3 143 963 B1 discloses a three-part spacer mold with a tibia spacer mold, a femur spacer mold and a third mold for producing a component which fills an intramedullary canal.

U.S. Pat. No. 10,071,511 B2 discloses casting molds for producing tibial components of knee spacers. Tibial components of differing heights may be fabricated using these casting molds. The casting mold consists of a lower part and an upper part which form a cavity into which a polymethyl methacrylate bone cement paste may be injected via a port. The height of the tibial component to be cast is defined by a latch mechanism with teeth which sets the distance between the lower part and the upper part of the casting mold.

A similar concept is known from U.S. Pat. No. 9,433,506 B2 which claims a mold for a knee spacer. The casting mold here contains a port which, after demolding, is present as a stem in the intramedullary space. The casting mold is filled via the port with the assistance of a cement cartridge.

It is thus the object of the present invention to overcome the disadvantages of the prior art. In particular, the object of the invention is to develop an inexpensive device for producing a knee spacer component of a knee spacer by curing bone cement paste and in the development of a method which can be carried out simply and expensively for producing a knee spacer component of a knee spacer by curing bone cement paste, with which one-part knee spacer components, i.e. tibial components and femoral components, can be produced by medical personnel in the operating room using bone cement paste, in particular polymethyl methacrylate bone cement. Tibial components and femoral components are similar in structure. They consist of a stem and a head or plateau.

A further object of the invention is to develop a device with which medical personnel can produce knee spacer components intraoperatively using bone cement paste, in particular polymethyl methacrylate bone cement paste (PMMA bone cement paste). The basic structure of the device to be developed should in principle be identical for the tibial component and for the femoral component of knee spacers. The device should therefore be suitable in a first variant for producing the tibial component and in a second variant for producing the femoral component of knee spacers. It is intended to be possible to produce the knee spacer components of knee spacers using polymethyl methacrylate bone cement paste of both normal and high viscosity.

A high injection pressure is needed for completely filling a casting mold with a high-viscosity bone cement paste. The device to be developed should therefore be such that (polymethyl methacrylate) bone cement paste can be injected into the device from a bone cement cartridge. When using non-high-viscosity bone cement paste, the bone cement paste must not flow out of the sprue once the casting mold has been filled. To this end, it is necessary to configure the casting mold so as reliably to prevent lower viscosity bone cement paste from flowing out of the casting mold during separation of the casting mold from the bone cement cartridge. Such closure should be possible without the need for openings for valves of complex construction in the wall of the casting mold. Openings in the wall of the casting mold may lead to leaks in the casting mold if the bone cement paste is injected into the casting mold under high pressure. Furthermore, the sprue region of the casting mold should be configured such that, on the one hand, easy filling of the casting mold with bone cement paste is possible and, on the other hand, any sprue residues can be easily removed once curing of the bone cement paste is complete.

Furthermore, it should be possible in one configuration of the device to also produce knee spacer components without using bone cement cartridges using (polymethyl methacrylate) bone cement paste which is mixed manually in suitable mixing bowls.

SUMMARY

The objects of the invention are achieved by a device for producing a knee spacer component by curing bone cement paste, wherein the knee spacer component is provided in the medical field for temporarily replacing part of a knee joint comprising an articulating surface of the knee joint, the device having

- a casting mold for molding the knee spacer component from bone cement paste;
- a valve seat which is connected to the casting mold, wherein the valve seat has a regionally or in places closed head side with at least one first feed-through, wherein the at least one first feed-through opens into the casting mold;
- a valve body which is mounted so as to be rotatable relative to the valve seat and which has a sealing face, wherein the sealing face is oriented in the direction of the regionally closed head side of the valve seat, wherein at least one second feed-through is arranged in the sealing face;
- wherein the valve seat and the valve body together form a valve, wherein the valve is reversibly transferable into an open position and a closed position by rotation of the valve body relative to the valve seat, wherein, in the open position of the valve, the at least one first feed-through of the valve seat and the at least one second feed-through of the valve body are located above one another at least in places and provide a connection through the valve which is permeable to bone cement paste, wherein, in the closed position of the valve, the at least one first feed-through of the valve seat is covered by the sealing face of the valve body, wherein, in the closed position of the valve, the casting mold is closed in liquid-tight manner for bone cement paste.

Liquid-tight means that the non-cured, i.e. fluid, bone cement paste and preferably also a liquid monomer liquid as starting component of the bone cement cannot flow out of or penetrate through the connection at the port.

Covered for bone cement paste means that the bone cement paste in the valve is prevented from flowing to such a degree that it cannot flow through the valve prior to curing. For normal-viscosity bone cement pastes, it is sufficient to this end for the bone cement paste to be incapable of flowing in a straight line through the valve and for the free passage cross-sections to be smaller than 1 mm. Bone cement pastes are viscous or high-viscosity fluids, as indicated by the term "paste". The viscosity of a bone cement paste amounts to at least 10 Pa's, which is essentially equivalent to the viscosity of liquid honey. In addition, the bone cement paste cures within a few minutes, meaning that passage is then no longer possible. Provision may preferably be made for the bone cement paste to have a viscosity of at least 10 Pas.

A bone cement paste or a fluid bone cement paste is understood to mean a mixed (i.e. ready-to-use) bone cement paste which has a viscid consistency. The viscosity of bone cement preferably corresponds to that of honey or is even higher. The terms fluid bone cement and bone cement paste are used synonymously.

The casting mold is preferably internally hollow.

Provision may be made for the sealing face to be closed apart from the at least one second feed-through.

Provision may preferably also be made for the casting mold to have an interior which replicates a negative shape of a tibial plateau or of condyles.

Provision may also be made for the valve seat to be connected to a casting mold wall of the casting mold in liquid-impermeable manner.

Provision may further be made for the valve seat to be configured at one end face of a cavity delimited by the casting mold as a disk, in particular as a planar disk.

Provision may preferably also be made for the valve seat and the valve body to be hollow-cylindrical.

Provision may further be made for the casting mold to be in two parts or multiple parts, wherein the parts of the casting mold are preferably able to be pushed into one another. The casting mold is particularly preferably in two parts.

The casting mold is intended to withstand a pressure of 10 $N/cm^2$, in order also to enable the use of high-viscosity bone cement.

In the present patent application, the statements of direction ("proximal", "distal" and "lateral") and the statements relating to planes ("sagittal plane", "front plane" and "transverse plane") relating to the knee spacer or knee spacer components and the casting mold are used in the same way as would be understood as a main anatomical direction or body plane when inserted into the patient. Here, "proximal" means towards the center of the body and "distal" means remote from the center of the body.

The stem is provided for connection to a bone (in the case of tibial components with the tibia and in the case of femoral components with the femur) and for this purpose may preferably be introduced into a proximal or distal end of the prepared bone or into the bone canal.

Provision may preferably be made for the device for producing a knee spacer component of a knee spacer to be suitable for application of at least one antibiotic and/or antimycotic active ingredient.

The knee spacer component should preferably be fabricated in one part from a biocompatible bone cement paste, such as polymethyl methacrylate (PMMA), wherein the PMMA particularly preferably contains at least one antibiotic and/or antimycotic dissolvable from the PMMA.

Provision may preferably be made for the regionally closed head side of the valve seat and the sealing face of the valve body to be disks or be disk-shaped.

Provision may preferably be made for the valve seat to delimit the casting mold.

The terms "open state" and "closed state" of the valve or of the valve body relative to the valve seat and the terms "open position" and "closed position" of the valve or of the valve body relative to the valve seat are used synonymously.

Provision may be made for the valve seat to be connected to the casting mold so as not to be rotatable relative to the casting mold, preferably for the valve seat to be connected fixedly and/or rigidly to the casting mold or to be formed as one part with the casting mold.

In this way, sealing or liquid-tight connection of the valve seat relative to the casting mold may be achieved in a structurally simple and thus inexpensive way.

Provision may further be made for the valve to be manually operable, preferably manually operable from outside the device, wherein the valve body is particularly preferably manually rotatable relative to the valve seat and the valve is transferable by rotation from the closed position into the open position and from the open position into the closed position.

In this way, the valve of the device can conveniently be operated from outside, in order to change or detach a bone cement cartridge.

Provision may moreover be made for the at least one first feed-through of the valve seat to be covered, in the closed position of the valve, with the sealing face of the valve body, wherein the regionally closed head side of the valve seat and the sealing face of the valve body are preferably spaced apart from one another by a maximum of 2 mm, particularly preferably by a maximum of 1 mm and very particularly preferably by a maximum of 0.5 mm.

In this way, it may be ensured that the bone cement paste filled into the casting mold (the fluid bone cement) cannot be expelled back out of the casting mold through the valve when the valve is closed. If the bone cement paste cures with these thicknesses or cross-sections in the region of the sprue, it may be readily manually broken off or cut through once the spacer has cured and need not be separated with a saw. Sprues of such thicknesses are therefore harmless since they do not appreciably delay OP procedures during an OP.

According to a preferred further development of the present invention, provision may be made for the valve body to be mounted so as to be rotatable about an axis of rotation relative to the valve seat, wherein the axis of rotation extends perpendicular to the sealing face of the valve body or wherein the axis of rotation extends along an axis of rotational symmetry of the sealing face of the valve body.

As a result, the bone cement paste flowing through the valve can be cut or twisted off the valve body by rotation. This enables a smooth cut surface and little application of force during shearing off. Rotation of the bone cement cartridge may further also be used for shearing off the bone cement paste. It is preferred for the axis of rotation to extend along the axis of rotational symmetry of the sealing face of the valve body. If the axis of rotation extends perpendicular to the sealing face of the valve body, the valve may be constructed in the manner of a tap (for example for beer).

Provision may also be made for the valve body to have a port for liquid-tight connection of a bone cement cartridge or of a handle of the device or to be firmly connected to such a port.

Provision may further be made for the valve body to have a port for liquid-tight connection of a bone cement cartridge or to be firmly connected to such a port.

In this way, the valve body can be operated with the assistance of a connected bone cement cartridge or with the handle.

Provision may here be made for the device to have an adapter element which is connected or connectable to a bone cement cartridge, wherein the adapter element is detachably and interlockingly connected or connectable to the port, such that an interior of a bone cement cartridge is connected or connectable permeably for bone cement paste via the adapter element to the at least one second feed-through.

This ensures that the bone cement paste can be straightforwardly filled into the casting mold from the bone cement cartridge through the valve in the open position thereof.

Provision may further be made for the port to comprise, for liquid-tight connection of a bone cement cartridge or a handle, an inner thread in the valve body or an outer thread on the valve body, wherein an adapter element of the bone cement cartridge or on the bone cement cartridge preferably has a mating thread matching the inner thread or the outer thread, or the handle of the device has a mating thread matching the inner thread or the outer thread.

In this way, a stable and liquid-tight connection to the port may on the one hand be produced and on the other hand use may be made of the rotation during the screwing movement at the start or after the end of the screwing movement to rotate the valve body relative to the valve seat and so transfer the valve from the open to the closed state or transfer the valve from the closed to the open state.

By using a suitable thread, an additional safety function of the device may in particular be achieved by its only being possible to detach a bone cement cartridge or the handle with the valve closed and its only being possible to open the valve with the bone cement cartridge or the handle connected.

Provision may be made for the inner thread in the valve body or the outer thread on the valve body to be a right-hand thread and for the valve to be transferable from the closed to the open position by equidirectional rightward rotation of the valve body and for the valve to be transferable from the open to the closed position by contradirectional leftward rotation of the valve body or for the inner thread in the valve body or the outer thread on the valve body to be a left-hand thread and for the valve to be transferable from the closed to the open position by equidirectional leftward rotation of the valve body and for the valve to be transferable from the open to the closed position by contradirectional rightward rotation of the valve body or for the inner thread of the valve seat and the inner thread and the outer thread of the valve body all to be left-hand threads or all to be right-hand threads, wherein an outer thread of an adapter element or an outer thread of the handle for liquid-tight connection of a bone cement cartridge to the port preferably also has the same direction of rotation.

The purpose of these measures is also to ensure that the valve closes automatically when the bone cement cartridge or the handle is unscrewed and the valve opens automatically when the bone cement cartridge or handle is screwed in.

Provision may also be made for the valve body to be mounted so as to be rotatable about an axis of rotation relative to the valve seat, wherein the axis of rotation is oriented in the direction of the at least one first feed-through.

Provision may further be made for the valve body to be rotatable by an angle of a maximum of 280° relative to the valve seat, preferably of a maximum of 180°, particularly preferably of a maximum of 100° relative to the valve seat and very particularly preferably of up to 90° relative to the valve seat.

Two feed-throughs may preferably be arranged in each of the valve seat and the valve body, wherein two feed-throughs are preferably arranged offset by 180° about the center point of disks of the valve seat and of the valve body, wherein the disks form the regionally closed head side of the valve seat and the sealing face of the valve body.

Provision may moreover be made for the device to have a bone cement cartridge for mixing bone cement starting components and for delivering mixed bone cement paste from the bone cement cartridge and preferably to have a bone cement cartridge for mixing polymethyl methacrylate bone cement starting components and for delivering mixed polymethyl methacrylate bone cement paste from the bone cement cartridge, wherein the bone cement cartridge particularly preferably contains the bone cement starting components for producing the bone cement paste in mutually separate regions.

In this way, the device is further completed since the device may then also provide the bone cement paste which is filled into the casting mold for forming the knee spacer component of the knee spacer.

As an alternative to the bone cement cartridge, provision may also be made for the device to have a monomer liquid container containing monomer liquid, a bone cement powder (preferably a packaged bone cement powder) and a mixing cup for manually preparing and mixing a bone cement paste from the monomer liquid and the bone cement powder, wherein the device additionally particularly preferably has a mixing spatula.

Provision may also be made for the device to have a handle which is connectable to the valve body and with which the valve body is rotatable relative to the valve seat, wherein the handle preferably has a cavity for receiving bone cement paste, which cavity is connected to the at least one second feed-through in liquid-permeable manner.

As a result, the valve may be transferred manually from the closed to the open state with the assistance of the handle.

Provision may preferably also be made for the sum of all free openings of the at least one first feed-through in the closed head side to be at most as large as the closed surface of the head side and for the sum of all free openings of the at least one second feed-through in the sealing face to be at most as large as the closed surface of the sealing face.

This ensures that the valve can be closed stably and impermeably to the bone cement paste by rotation of the valve body relative to the valve seat.

Provision may also be made for the valve seat to have an inner thread on the inside and the valve body to have a matching outer thread on the outside, such that the valve body is able to be screwed into the valve seat.

Due to this measure, a good sealing effect can be achieved at the connection between the valve body and the valve seat. In addition, the valve can be simply and inexpensively assembled in this way.

Provision may further be made for the casting mold to have a trough-shaped mold with a cavity and a punch, wherein the punch is insertable or inserted into the cavity of the trough-shaped mold and the punch is axially displaceable in the cavity, and wherein the trough-shaped mold preferably has a cavity bottom, wherein the cavity bottom forms the contour of one or more articulating sliding surfaces of the knee spacer component.

In this way, the knee spacer component may be molded by pressing the bone cement paste in the casting mold with the assistance of the punch. In addition, this also makes it possible to vary the height of the knee spacer component.

Provision may here advantageously be made for the bottom of the punch to be concavely shaped. In this way, air can escape from the casting mold in the direction of a gap between the punch and the mold.

Provision may here be made for the valve seat to be arranged in the punch, preferably to be arranged at the end of a part of the punch which shapes a stem of the knee spacer component.

As a result, any excess bone cement paste can be expelled from the casting mold by the punch on pressing the punch in. In this way, the height of the knee spacer component can be adjusted.

A stem or stem mold is not necessary. The knee spacer component may also be embodied without a stem. The valve or the sprue or flash may here be arranged directly on a level on one side of the tibial platform.

Provision may preferably also be made for the at least one first feed-through in the regionally closed head side to have the same size and shape as the at least one second feed-through in the sealing face.

Provision may preferably likewise be made for the at least one first feed-through in the regionally closed head side to be two first feed-throughs and the at least one second feed-through in the sealing face to be two second feed-throughs, wherein the two first feed-throughs are preferably arranged in the valve seat in quadrants arranged opposingly with regard to the axis of rotation of the valve body and the two second feed-throughs are arranged in the sealing face in quadrants arranged opposingly with regard to the axis of rotation of the valve body.

Due to these two measures, a sufficient flow area can be provided for the viscid bone cement paste and unilateral loading of the valve which might otherwise lead to valve leaks can be avoided.

The present invention also proposes that a collar is arranged on the sealing face of the valve body, which collar rests on an edge of the valve seat or a collar is arranged on the regionally closed head side of the valve seat, which collar rests on an edge of the valve body.

In this way, stable guidance of the valve body on the valve seat can be achieved. In the event of a given thread length of the valve body, the position of the at least one second feed-through may further be precisely defined with regard to the at least one first feed-through.

Provision may moreover be made for a handgrip to be fastened or fastenable to the valve body, which handgrip has at least one radial extent with regard to the axis of rotation of the valve body, wherein the handgrip is preferably fastened or fastenable to an opposite side of the valve body from the sealing face, wherein the valve body may particularly preferably be rotated by a maximum of 90° relative to the valve seat.

As a result, the valve is conveniently manually operable from outside. Using this handgrip, the valve body can be rotated from the open position into the closed position of the valve.

Provision may further be made for the valve body and the valve seat to be fabricated of plastics, in particular of thermoplastics, wherein the valve seat is preferably formed as one part with the casting mold.

In this way, the valve and thus the device can be fabricated inexpensively and as a hygienic disposable product.

Provision may preferably also be made for a latch element to be arranged on the sealing face of the valve body and a mating latch element to be arranged on the head side of the valve seat, wherein the latch element is able to be brought into engagement with the mating latch element, wherein the latch element is positioned on the valve body such that rotation or unscrewing of the valve body from the valve seat is limited to an angle of rotation of a maximum of 90° when the valve body is maximally put or screwed into the valve seat.

As a result, it can be ensured that the valve body is not rotated by more than 90° relative to the valve seat in the latched state. As a result, it is possible to prevent the valve body from being unscrewed too far out of the valve seat, an excessively large gap between the valve body and the valve seat thereby being created and the valve also becoming permeable to the bone cement paste in the closed position.

Provision may moreover be made for the casting mold to be in two parts or multiple parts, wherein a gap through which air or gas can escape from the interior of the casting mold is present between at least two of the parts of the assembled casting mold.

As a result, entrapped air which might impair the surface of the knee spacer component produced from the bone cement paste is prevented from remaining in the casting mold.

Provision may also be made for the device to have a collecting vessel, wherein the valve is connected or connectable on the side remote from the casting mold to the collecting vessel for receiving excess bone cement paste which emerges from the casting mold through the valve in the open position or the valve is formed as one part with the collecting vessel.

In this way, it is possible to prevent emerging bone cement paste from soiling or contaminating the operating room.

The objects underlying the present invention are also achieved by a method for producing a knee spacer component for temporarily replacing part of a knee joint comprising an articulating surface of the knee joint, wherein the method is carried out with a device according to the invention, the method having the following chronological steps:

A) connecting a bone cement cartridge to the device in liquid-tight manner;
B) injecting bone cement paste from the bone cement cartridge through the valve in the open position into the casting mold;
C) rotating the valve body relative to the valve seat and so transferring the valve into the closed position and shearing off the bone cement paste at the at least one first feed-through in the regionally closed head side of the valve seat by rotation of the valve body relative to the valve seat;
D) detaching the bone cement cartridge from the casting mold;
E) curing the bone cement paste in the casting mold; and
F) removing the resultant molded and cured knee spacer component from the casting mold.

The knee spacer is intended for medical applications. The method according to the invention does not comprise implantation in a patient but merely the forming of the knee spacer. After step F), the knee spacer can be trimmed of flash, smoothed, sanded, cleaned, polished and/or roughened in places.

In order to remove the molded and cured knee spacer from the casting mold in step F), the casting mold can be opened after step E).

Provision may be made according to the invention for the casting mold to have a trough-shaped mold and a punch. In this way, the knee spacer component can be molded by punch pressure in order to obtain a sliding surface which is maximally smooth and lacking in defects.

Provision may here preferably be made for the punch to be pressed into the trough-shaped mold in order to mold the knee spacer component. Provision may particularly preferably be made to this end for the punch to be pushed into the trough-shaped mold after step B) and particularly preferably before step C). Part of the bone cement paste may thus be expelled back out of the casting mold through the valve.

Provision may be made for the following intermediate steps to proceed after step D) and before step E):

D2) connecting a new bone cement cartridge to the device in liquid-tight manner, wherein bone cement paste or starting components for producing the bone cement paste is/are present in the new bone cement cartridge;
D3) rotating the valve body relative to the valve seat and so transferring the valve into the open position;
D4) injecting bone cement paste from the new bone cement cartridge through the valve in the open position into the casting mold;
D5) rotating the valve body relative to the valve seat and so transferring the valve into the closed position and shearing off the bone cement paste at the at least one first feed-through in the regionally closed head side of the valve seat by rotation of the valve body relative to the valve seat; and
D6) detaching the new bone cement cartridge from the casting mold;
wherein steps D2) to D6) are preferably repeated once or multiple times with in each case new bone cement cartridges which contain bone cement paste or the starting components thereof until the casting mold is filled completely or as required with bone cement paste.

In this way, a casting mold with a large volume may be filled with a plurality of bone cement cartridges containing small volumes of the bone cement paste. This is advantageous, for example, for the production of large-volume knee spacers.

For liquid-tight connection of the bone cement cartridge and/or the new bone cement cartridge, provision may moreover be made for said cartridge to be connected to a port on the valve body of the device, wherein the bone cement cartridge or the new bone cement cartridge is rotated or screwed into the port and, for detaching the bone cement cartridge and/or the new bone cement cartridge from the port, the bone cement cartridge or the new bone cement cartridge is rotated out of or unscrewed from the port, and/or In addition to being screw-fastened, the bone cement cartridge may for example be connected to the valve body with a bayonet closure.

By rotating or screwing the bone cement cartridge into the valve body, it is possible to provide a liquid-tight connection between the valve body and the bone cement cartridge. In addition, the rotation may also rotate or cause the valve body to rotate relative to the valve seat.

Provision may further be made for injection of the bone cement paste from the bone cement cartridge or the new bone cement cartridge to proceed by pushing a piston into an interior of the bone cement cartridge.

In this way, the bone cement paste can straightforwardly be injected from the bone cement cartridge through the open valve into the casting mold.

Provision may also be made for rotation of the valve body relative to the valve seat to proceed by screwing the valve body in the valve seat or by manually rotating the valve body relative to the valve seat, wherein manual rotation preferably proceeds by operation of a handgrip which is connected to the valve body.

As a result, the valve is simply operable by the user.

Provision may moreover be made for the casting mold to have a trough-shaped mold and a punch, wherein, before step E), the punch is pressed into the trough-shaped mold and as a result the knee spacer component is molded from the bone cement paste in the casting mold, wherein, preferably on pressing the punch into the trough-shaped mold, part of the bone cement paste is expelled from the casting mold through the valve in the open position and wherein particularly preferably the part of the bone cement paste which is pressed into a collecting vessel is that associated with the at least one second passage of the valve.

In this way, a knee spacer component with variable height can be molded. In addition, by pressing on the punch, the shaping interior surface of the casting mold can be completely wetted with bone cement paste so as to obtain a complete knee spacer component without defects.

It should be noted in this connection that the valve need not here any longer be the same valve through which the bone cement paste was filled into the casting mold. On removal of the bone cement cartridge, the valve body may be removed at the same time and a handle with a new valve body may be inserted into the valve seat, such that the valve seat on the casting mold and the valve body of the handle form a new valve which does, however, resemble the valve made up of the valve seat of the casting mold and the valve body for connection of the bone cement cartridge.

The objects underlying the present invention are further achieved by a method for producing a knee spacer component for temporarily replacing part of a knee joint comprising an articulating surface of the knee joint, wherein the method is carried out with a device according to the invention, the method having the following chronological steps:

A) producing a bone cement paste;
B) filling a mixed bone cement paste into the casting mold;
C) compressing the casting mold and so expelling part of the bone cement paste from the casting mold through the valve in the open position;
D) rotating the valve body relative to the valve seat and so transferring the valve into the closed position and shearing off the bone cement paste at the at least one first feed-through in the regionally closed head side of the valve seat by rotation of the valve body relative to the valve seat;
E) curing the bone cement paste in the casting mold; and
F) removing the resultant molded and cured knee spacer component from the casting mold.

The knee spacer is intended for medical applications. The method according to the invention does not comprise implantation in a patient but merely the forming of the knee spacer. After step F), the knee spacer can be trimmed of flash, smoothed, sanded, cleaned, polished and/or roughened in places.

Provision may be made for a step B1) to proceed between steps B) and C): B1) closing the casting mold apart from the valve.

This ensures that the bone cement paste can only emerge from the casting mold through the valve.

Provision may further be made for the casting mold to have a trough-shaped mold and a punch, wherein, in step c), the punch is pressed into the trough-shaped mold and as a result the knee spacer component is molded from the bone cement paste in the casting mold, wherein, preferably on pressing the punch into the trough-shaped mold, part of the bone cement paste is expelled from the casting mold through the valve in the open position.

In this way, a knee spacer component with variable height can be molded. In addition, by pressing on the punch, the shaping interior surface of the casting mold can be completely wetted with bone cement paste so as to obtain a complete knee spacer component without defects.

Provision may also be made for the bone cement paste to be mixed before step B) in the bone cement cartridge from a monomer liquid and a cement powder, wherein, optionally before step D3) and preferably before step D2), the bone cement paste is preferably mixed in the new bone cement cartridge from a monomer liquid and a cement powder.

In this way, a freshly mixed bone cement paste can be used for producing the knee spacer. PMMA bone cement pastes in particular can be stored for periods of more than a few minutes only with difficulty if at all in the mixed state. In addition, suitable therapeutic pharmaceutical active substances, such as antibiotics and antimycotics, may accordingly also be mixed into the bone cement paste shortly before production of the knee spacer.

Provision may moreover also be made for rotation of the valve body relative to the valve seat to proceed by screwing the valve body in the valve seat or by manually rotating the valve body relative to the valve seat, wherein manual rotation preferably proceeds by operation of a handgrip on the valve body.

As a result, the device is simply operable.

The invention is based on the surprising recognition that, due to a valve body which is rotatable in a valve seat, it is possible to provide a device with a casting mold in which the sprue or flash can be sheared off or largely sheared off with the valve body and simultaneously to close the casting mold or at least constrict the remaining channels to such an extent that the bone cement paste can continue to be held under pressure in the casting mold so that it can be pressed against the inside of the casting mold, wherein the bone cement paste is simultaneously prevented from being expelled back or any further out of the casting mold through the opening. The device also makes it possible to fill the casting mold in succession with the contents of a plurality of bone cement cartridges without the bone cement paste being able to flow back out of the casting mold through the opening. In this way, even with bone cement cartridges which provide only small volumes of bone cement, it is possible to produce knee spacers or knee spacer components with a large volume. It is likewise also possible to use punching of the knee spacer component to adjust the height of the knee spacer component and to press the bone cement paste against the shaping surfaces in the casting mold, wherein excess bone cement paste can be expelled from the casting mold through the open valve, wherein the resultant flash can be sheared off or largely sheared off with the valve body before the bone cement paste cures.

Bone cement paste, in particular non-high-viscosity bone cement paste, cannot flow out of the casting mold through the closure or closed valve. Any formation of defects in the knee spacer or in the knee spacer components as a result of bone cement flowing out is prevented as a result. Furthermore, the measures according to the invention ensure that any residue of bone cement paste left behind in the bone cement cartridge (sprue) and/or bone cement paste expelled from the casting mold (flash) is separated from the bone cement paste in the casting mold. Once curing of the bone cement paste is complete, it is therefore no longer necessary to separate the sprue or flash mechanically, for example by sawing. Any remaining thin connections can easily be broken or cut off. This saves time and effort for the OP personnel.

The sprue or flash of the knee spacer component is formed by the opening with the valve seat and the valve body. Rotating the valve body relative to the valve seat from the open position into the closed position of the valve closes the casting mold impermeably to bone cement paste. This means that the sprue/flash formed by the valve seat and the valve body, or the sprue-/flash-shaping parts simultaneously function as a valve. There is no need for complex additional valves.

The valve body may be manually rotated relative to the valve seat by a handgrip on the valve body. Rotation may advantageously also proceed by the valve body being co-rotated by the bone cement cartridge when the bone cement cartridge is unscrewed. It is, however, necessary here for a limit stop to limit the rotational movement of the valve body relative to the valve seat so that closure can be reliable and so that the valve body cannot be completely unscrewed from the valve seat.

Back pressure should be applied by the user in order to fill the casting mold. The casting mold may be filled with bone cement paste until the desired height of the knee spacer component is established in the casting mold. The punch of the casting mold may here be expelled from the trough-shaped mold of the casting mold as further bone cement paste is filled into the casting mold. The user must to this end maintain pressure on the casting mold via the punch. Entrapped air can escape from the gap between the punch and the trough-shaped mold. Once the desired height of the knee spacer component in the casting mold has been reached, the user can simply stop pressing further bone cement paste into the casting mold.

Alternatively, the bone cement paste may be filled into the casting mold in excess and the height is adjusted by compressing the casting mold after filling with the bone cement paste until the desired height of the knee spacer component in the casting mold is achieved. To this end, the punch may be pushed (for example with the handle) into the trough-shaped mold to a depth such that the desired height of the knee spacer component is established. Outflowing excess bone cement paste can flow away through the open valve. The excess bone cement paste is preferably received in a collecting vessel. The collecting vessel may be arranged in the handle with which the punch and the valve are operated.

The height of knee spacer component can be continuously adjusted in this manner. There is consequently no need with the device according to the invention and the method according to the invention for a height-adjusting latching or fastening means on the casting mold for adjusting the height of the knee spacer component.

The parts of the casting mold also need not be fastenable to one another in pressure-tight manner. No clips, screws or other fastening means are required to fasten together the parts of the casting mold or to absorb pressure. These parts consequently cannot be lost in the operating room and therefore cannot disrupt the course of an operation.

It is preferred according to the invention for an inner thread or parts of an inner thread to be arranged on the inside of a hollow-cylindrical valve body, wherein the inner thread is reversibly connectable by screwing together with the outer thread of a cartridge head of a bone cement cartridge. Using this device, knee spacer components may be produced in such a manner that firstly a polymethyl methacrylate bone cement paste is produced in a bone cement cartridge by mixing cement powder and monomer liquid, that in a second step the bone cement cartridge is screwed into the valve body, wherein the valve or valve body is rotated into the open position, that in a third step a punch of the casting mold with the valve seat, the valve body and the bone cement cartridge is pushed into a trough-shaped mold of the casting mold until the desired height above the bottom of the trough-shaped mold is reached, that in a fourth step the polymethyl methacrylate bone cement paste is pressed out of bone cement cartridge with a delivery device into the cavity of the casting mold under the punch until the desired filling level under the punch is reached, wherein the air escapes from the cavity of the casting mold via an interspace between the trough-shaped mold and the punch, that in a fifth step the bone cement cartridge is unscrewed from the valve body, wherein the valve or valve body is rotated relative to the valve seat into the closed position, whereby the polymethyl methacrylate bone cement paste in the cavity of the casting mold is separated from excess polymethyl methacrylate bone cement paste in the valve body, that in a sixth step, once the polymethyl methacrylate bone cement paste has cured, the punch is withdrawn from the trough-shaped mold, wherein the knee spacer component is detached from the punch, and in a seventh step the knee spacer component is removed from the casting mold or the trough-shaped mold of the casting mold.

In time and labor-saving manner, the knee spacer component does not here contain any sprue or flash of excess polymethyl methacrylate bone cement which has to be mechanically separated.

In a second variant configuration, the valve body assumes the form of a hollow cylinder on which a handgrip is arranged on the narrow side thereof opposite the sealing face. The device is handled in such a manner that in a first step polymethyl methacrylate bone cement powder and monomer liquid are mixed together in a mixing bowl or also in a bone cement cartridge to form a homogeneous polymethyl methacrylate bone cement paste, that in a second step an excess of bone cement paste in comparison with the volume of the knee spacer component to be produced is poured, injected or introduced with a spatula into a trough-shaped mold of the casting mold, that in a third step a punch of the casting mold with the valve seat and the valve body is put into the cavity of the casting mold, wherein the valve or valve body is moved relative to the valve seat into the open position by rotation of the handgrip, that in a fourth step, using the handgrip, the punch is pushed in the direction of the bottom of the trough-shaped mold until the desired height of the bone cement paste in the casting mold is reached, wherein the excess bone cement paste passes through the valve seat and the valve body (or through the at least one first passage in the valve seat and through the at least one second passage in the valve body), that in a fifth step the handgrip on the valve body is rotated such that the valve or the valve body is transferred into the closed position relative to the valve seat, whereby the excess polymethyl methacrylate bone cement paste in the valve body is separated from the polymethyl methacrylate bone cement paste in the cavity of the casting mold, that in a seventh step the polymethyl methacrylate bone cement paste cures in the casting mold, that in an eighth step the punch is withdrawn from the trough-shaped mold, wherein the punch separates from the cured knee spacer component and that in a ninth step the knee spacer component is removed from the casting mold or the trough-shaped mold of the casting mold.

In time and labor-saving manner, the knee spacer component here does not have any flash of excess polymethyl methacrylate bone cement which has to be mechanically separated in troublesome manner. It is furthermore advantageous for the bottom of the punch to be concavely shaped so that the air is guided in the direction of the valve seat and through the valve seat and the valve body out of the cavity of the casting mold.

A knee spacer or the knee spacer components produced with the device may advantageously be used in the context of two-stage septic revisions, in which an infection with two or more microbial microorganisms and in particular with problematic microorganisms is present.

An exemplary device according to the invention may be composed of
- a) a trough-shaped mold as part of the casting mold, wherein the trough-shaped mold has a cavity, wherein the cavity bottom has the contour of one or more articulating sliding surfaces,
- b) a punch as part of the casting mold which is axially displaceable in the cavity of the trough-shaped mold, wherein the punch contains the opening which liquid-permeably connects the bottom of the punch facing the cavity bottom of the trough-shaped mold to the opposing top of the punch,
- c) a dimensionally stable hollow-cylindrical valve seat,
- c1) which is arranged non-rotatably in the opening of the punch,
- c2) wherein the valve seat takes the form of a disk on its head side in which is arranged the at least one first feed-through which liquid-permeably connects the bottom of the punch to the top of the punch, wherein the area of the at least one first feed-through only occupies a maximum of 50 percent of the disk area of the valve seat, and
- c3) wherein the valve seat has an inner thread on the inside,
- d) a dimensionally stable, hollow-cylindrical valve body, which has an outer thread on the outside of the hollow cylinder, which thread is able to be screwed together with the inner thread of the valve seat
  wherein the valve body has on its sealing face, which faces the cavity of the trough-shaped mold and takes the form of a disk, the at least one second feed-through, wherein the area of the at least one second feed-through only occupies a maximum of 50 percent of the disk area of the valve body, and
  wherein the at least one second feed-through has an approximately identical size and shape as the at least one first feed-through of the valve seat,
  wherein, on being screwed into the valve seat, the valve body is rotated into an open position, such that the at least one second feed-through is located above the at least one first feed-through and a liquid-permeable connection from the interior of the casting mold to the surroundings is produced and can be rotated into a closed position such that the at least one second feed-through does not overlap with or cover the at least one first feed-through, and
- e) polymethyl methacrylate bone cement paste introduced into the cavity of the trough-shaped mold being delimited by the bottom of the punch and excess polymethyl methacrylate bone cement paste being arranged in the cavity of the valve body, wherein, by rotating the valve body into the closed position, the excess polymethyl methacrylate bone cement paste is separated or sheared off or largely sheared off from the polymethyl methacrylate bone cement paste in the cavity of the casting mold.

Once injection of the bone cement paste into the cavity of the casting mold is complete, the valve body is rotated manually such that the at least one second feed-through of the valve body is no longer located above or aligned with the at least one first feed-through of the dimensionally stable valve seat. In this way, the cavity of the casting mold is liquid-impermeably closed. Even a non-high-viscosity bone cement paste is consequently unable to flow out of the casting mold.

An exemplary method according to the invention for producing knee spacers with the device according to the invention may comprise the following successive steps:
- a) providing the casting mold and the trough-shaped mold of the casting mold,
- b) mixing the bone cement powder with the monomer liquid in a bone cement cartridge until a homogeneous bone cement paste has formed,
- c) liquid-permeably connecting the bone cement cartridge to the casting mold or to the valve on the casting mold by screwing the adapter element into an inner thread of the valve body, wherein the valve body is rotated into the open position,
- d) injecting the bone cement paste from the bone cement cartridge into the casting mold with the assistance of an expression device, wherein the bone cement paste expels the air in the cavity of the casting mold and the expelled air preferably emerges from the cavity of the casting mold into the surroundings through a gap between the trough-shaped mold and the punch,
- e) unscrewing the bone cement cartridge from the valve body, wherein the valve body is rotated from the open position into the closed position of the valve, whereby the at least one first feed-through and the at least one second feed-through are no longer located above one another, such that no bone cement paste can emerge from the cavity of the casting mold into the surroundings through the valve,
- f) detaching the bone cement cartridge from the casting mold,
- g) curing the bone cement paste in the casting mold,
- h) opening the casting mold once the bone cement paste has cured by taking the punch out of the trough-shaped mold and
- i) removing the knee spacer component.

An alternative exemplary method according to the invention for producing knee spacers with the device according to the invention may comprise the following successive steps:
- a) providing the casting mold and the trough-shaped mold of the casting mold,
- b) mixing a bone cement powder with a monomer liquid until a bone cement paste has formed (for example in a mixing bowl or also in a bone cement cartridge),
- c) filling the bone cement paste into the trough-shaped mold,
- d) optionally opening the valve by rotation of the valve body relative to the valve seat into the open position,
- e) inserting a punch of the casting mold with the valve in the open position into the cavity of the trough-shaped mold,
- f) pressing a punch of the casting mold in the direction of the cavity bottom of the trough-shaped mold until the desired height of the knee spacer component is reached, while simultaneously displacing the air and excess polymethyl methacrylate bone cement paste through the valve seat and the valve body in the open position into a cavity of the valve body, g) once the desired filling level of the polymethyl methacrylate bone cement paste has been reached, manually rotating the valve body relative to the valve seat into the closed position, such that the excess polymethyl methacrylate bone cement paste is separated from the polymethyl methacrylate bone cement paste in the cavity of the casting mold, h) curing the bone cement paste in the casting mold, i) opening the casting mold once the bone cement paste has cured by taking the punch out of the trough-shaped mold and i) removing the knee spacer component.

BRIEF DESCRIPTION OF THE DRAWINGS

Further exemplary embodiments of the invention are explained below with reference to thirty-three schematic figures but without thereby limiting the invention. In the figures:

FIG. 19 shows a schematic perspective cross-sectional view of the third device according to the invention with the valve open and punch pushed in;

FIG. 32 shows a schematic perspective external view of the fourth device according to the invention with punch pushed in.

DETAILED DESCRIPTION

Figure 1:
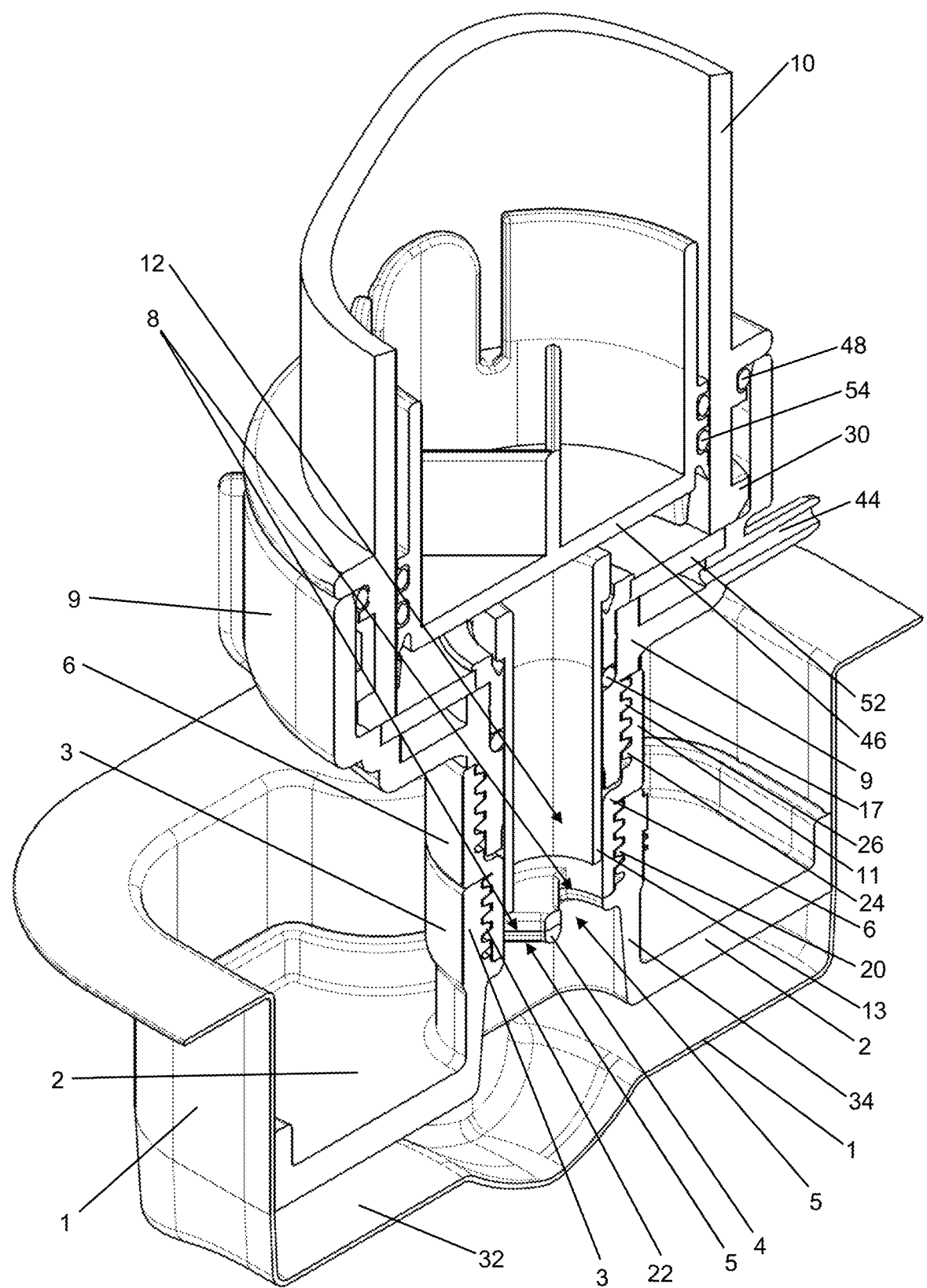
FIG. 1 shows a schematic perspective cross-sectional view of a first exemplary device according to the invention for producing a tibial component with the valve open.
Figure 2:
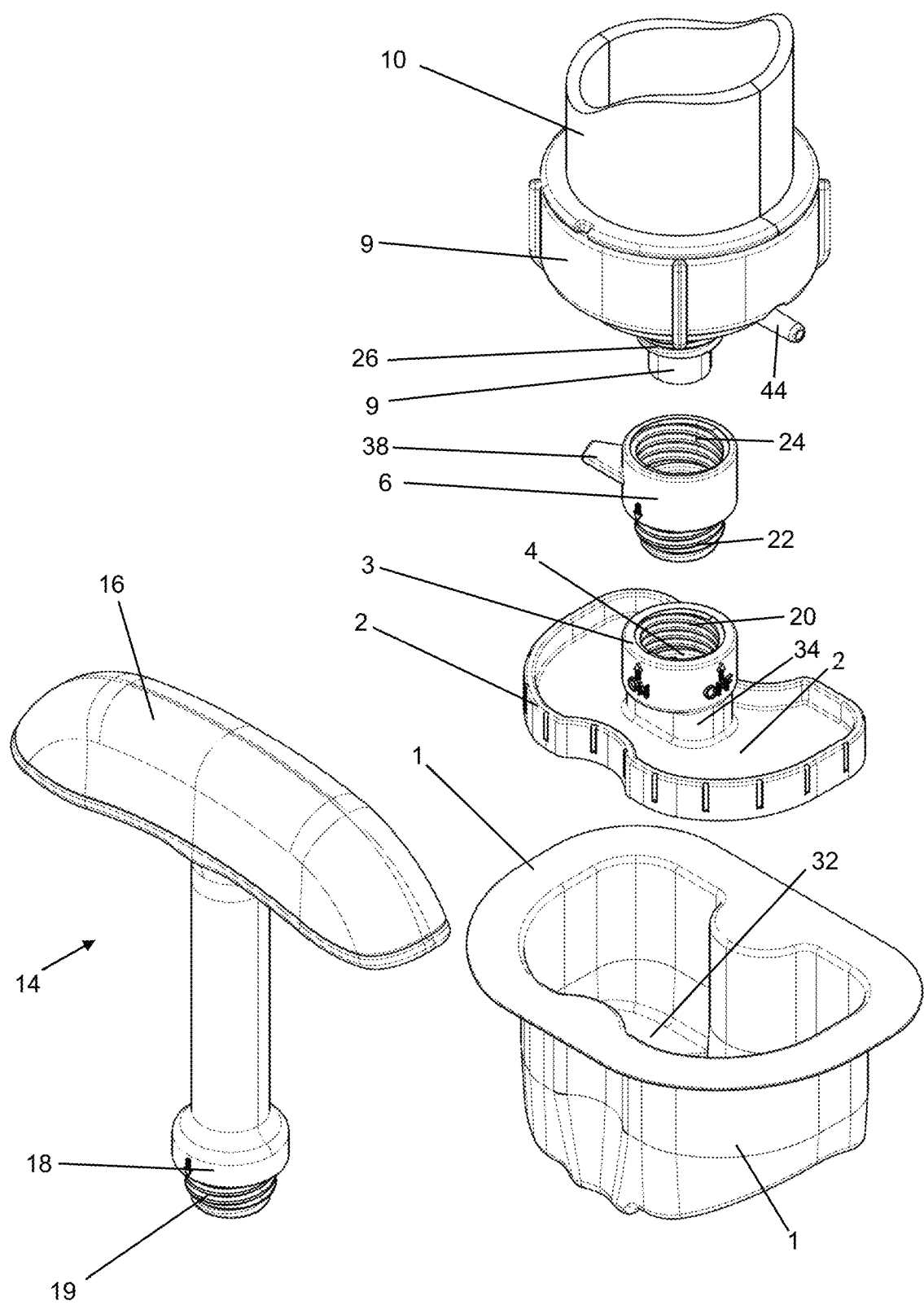
FIG. 2 shows a schematic external view of the parts of the first device according to the invention according to FIG. 1.

FIGS. 1 to 10 are drawings showing various views of a first exemplary embodiment of a device according to the invention for producing knee spacer components of a knee spacer and parts thereof.

The first device according to the invention is suitable and provided for producing a tibial component of a knee spacer. The device comprises a casting mold which is composed of two parts. The casting mold may have a trough-shaped mold 1 and a punch 2. The punch 2 can be inserted into the trough-shaped mold 1 and can be pushed into the trough-shaped mold 1 and preferably also withdrawn again. The trough-shaped mold 1 can be inexpensively fabricated from plastics film. The plastics film may have a plurality of layers. An opening for throughflow of bone cement paste 50, which may be delimited by a cylindrical wall of the punch 2, may be formed on one side of the punch 2. A valve seat 3 may be arranged in this opening. The valve seat 3 may be firmly connected to the punch 2 of the casting mold or even be formed as one part, as shown in FIGS. 1 to 10.

The valve seat 3 may take the form of a hollow cylinder which, apart from two first feed-throughs 5, is closed on a head side 4 oriented in the direction of the opening in the punch 2. The two first feed-throughs 5 may be quadrant-shaped and may preferably be arranged rotated or offset relative to one another by 180° with regard to the cylinder axis of the valve seat 3. A valve body 6 may be arranged in the interior of the valve seat 3 so as to be axially rotatable relative to the valve seat 3. The valve body 6 may have a sealing face 7 or surface oriented in the direction of the head side 4 of the valve seat 3. The valve body 6 may be constructed as a stepped hollow cylinder, the front part of which can be screwed or put into the valve seat 3.

Two second feed-throughs 8 may be arranged in the sealing face 7. The two second feed-throughs 8 may, similarly to the first feed-throughs 5, be quadrant-shaped and may preferably be arranged rotated relative to one another by 180° with regard to the cylinder axis of the valve body 6. The valve seat 3 and valve body 6 together form a valve of the device. An adapter element 9 for liquid-tight connection of a bone cement cartridge 10 may be screwed into the valve body 6. The bone cement cartridge 10 and the adapter element 9 may be part of the device according to the invention. The valve body 6 may on its open side, which is remote from the sealing face 7, be formed as a port 11 for connecting the adapter element 9.

The bone cement cartridge 10 may have on its front side a delivery opening 12 for delivering the bone cement paste 50 from the bone cement cartridge 10. The delivery opening 12 of the bone cement cartridge 10 may be arranged on the front side of a delivery tube 13 of the bone cement cartridge 10. The delivery opening 12 may also be arranged in and delimited by the adapter element 9. The adapter element 9 may close the bone cement cartridge 10 on its front side apart from the delivery opening 12 and optionally apart from a vacuum port 44, wherein the delivery tube 13 may project through the adapter element 9.

The device may have a handle 14 which forms a handgrip 16 at one end (see FIGS. 2, 4, 6, 7 and 10). A valve body 18 with an outer thread 19 may be arranged at the opposite end of the handle 14. The valve body 18 of the handle 14 may be or have been arranged in the valve seat 3 so as to be axially rotatable relative to the valve seat 3 (see FIGS. 6, 7 and 10). The valve body 18 of the handle 14 may have a sealing face or surface oriented in the direction of the head side 4 of the valve seat 3. The valve body 18 may be screwed or put into the valve seat 3.

Two second feed-throughs 21 of the handle 14 may be arranged in the sealing face. The two second feed-throughs 21 may, similarly to the first feed-throughs 5, be quadrant-shaped and may preferably be arranged rotated relative to one another by 180° with regard to the cylinder axis of the valve body 18 of the handle 14. The valve seat 18 of the handle 14 and the valve body 6 also together form a valve of the device. The handle 14 may have a hollow interior. The cavity in the interior of the handle 14 may be connected to the two second feed-throughs 21 of the handle 14. As a result, the cavity in the interior of the handle may form a collecting vessel for receiving excess bone cement paste 50, wherein the excess bone cement paste 50 from the casting mold can flow through the two second feed-throughs 21 into the collecting vessel when the valve formed by the valve body 18 and the valve seat 3 is in an open position in which the two first feed-throughs 5 in the valve seat 3 are connected liquid-permeably for the bone cement paste 50 to the two second feed-throughs 21 of the handle 14 or are arranged above one another.

The punch 2 can be pushed into the trough-shaped mold 1. The casting mold can be closed to the outside by putting the punch 2 into the trough-shaped mold 1. When the trough-shaped mold 1 and the punch 2 are nested in one another, a gap may be present for venting the interior of the casting mold (not visible in FIGS. 1 to 10). Air or gas can escape through the gap from the interior of the closed casting mold when a bone cement paste 50 is filled into the casting mold.

The valve seat 3 may have an inner thread 20 on its inside. The outer thread 19 of the handle 14 matches the inner thread 20 of the valve seat 3, such that the valve body 18 of the handle 14 can be screwed into the valve seat 3.

On the front half of the valve body 6 facing the sealing face 7, the valve body 6 may have on the outside thereof an outer thread 22 matching the inner thread 20 of the valve seat 3. The valve body 6 may be screwed with its outer thread 22 into the inner thread 20 of the valve seat 3.

The first feed-throughs 5 and the second feed-throughs 8 may be brought into overlap with one another by screwing the valve body 6 into the valve seat 3 until the limit stop is reached. The first feed-throughs 5 and the second feed-throughs 21 may likewise be brought into overlap with one another by screwing the valve body 18 of the handle 14 into the valve seat 3 until the limit stop is reached. The valve is then in the open state. In this open state, a bone cement paste 50 may flow out of the bone cement cartridge 10 into the casting mold through the first feed-throughs 5 and through the second feed-throughs 8, or a bone cement paste 50 may in this open state flow out of the casting mold into the collecting vessel in the handle 14 through the first feed-throughs 5 and through the second feed-throughs 21 of the handle 14.

By making a quarter rotation (by 90°) of the valve body 6 or valve body 18 relative to the valve seat 3, i.e. by unscrewing the valve body 6 or valve body 18 from the valve seat 3, the first feed-throughs 5 and the second feed-throughs 8 or second feed-throughs 21 may be offset relative to one another, such that the sealing face 7 of the valve body 6 covers the first feed-throughs 5 of the valve seat 3 and the closed regions of the head side 4 of the valve seat 3 cover the second feed-throughs 8 of the valve body 6 or the second feed-throughs 21 of the valve body 18. The valve is then in the closed state. Due to the small stroke of the valve body 6 or valve body 18 relative to the valve seat 3 in the event of a quarter rotation, the gap arising between the valve body 6 or valve body 18 and the valve seat 3 is so narrow (less than 1 mm wide) that a bone cement paste 50 of a normal, let alone high, viscosity, is incapable of passing through the gap. This is particularly the case because the bone cement paste 50 is deflected from its actual direction of flow by 90° in the gap.

The reverse side of the valve body 6 may have an inner thread 24 arranged in the port 11. The adapter element 9 has on its front side an outer thread 26 which matches the inner thread 24. The adapter element 9 may accordingly be screwed into the port 11 of the valve body 6. In this way, a liquid-tight connection can be created between the bone cement cartridge 10 and the valve body 6 and thus the casting mold. The inner thread 20 of the valve seat 3, the outer thread 19 of the valve body 18 of the handle 14, the outer thread 22 of the valve body 6, the inner thread 24 of the valve body 6 and the outer thread 26 of the adapter element 9 may all have the same direction of rotation, i.e. all these threads are right-hand threads or left-hand threads. As a result, the valve can be opened by screwing the adapter element 9 into the port 11 and continuing to rotate the adapter element 9 in the same direction. At the same time, the valve body 6 also provides a seal relative to the valve seat 3. The valve may as a result likewise be opened by screwing the handle 14 into the valve seat 3. At the same time, the valve body 18 also provides a seal relative to the valve seat 3.

The adapter element 9 may be or have been connected via a latching means 28 on the adapter element 9 to a mating latch 30 on a cylindrical wall of the bone cement cartridge 10. A circumferential seal 48 which seals the cylindrical wall of the bone cement cartridge 10 relative to the adapter element 9 may be provided for sealing.

The casting mold may have a bottom plate 32 for molding a sliding surface of a knee spacer component (not shown) molded with the casting mold. In the present case, this may be a tibial plateau. The bottom plate 32 may form the base or bottom of the trough-shaped mold 1. The punch 2 can be pushed into the trough-shaped mold 1 in the direction of the bottom plate 32. As a result, a bone cement paste 50 filled into the casting mold can be pressed against the bottom plate 32 of the trough-shaped mold 1. The casting mold and in particular the punch 2 of the casting mold may further have a stem molding 34 for forming a stem of a tibial component.

A grip 38 may be connected to the valve body 6. The valve body 6 can be manually rotated in the valve seat 3 with the grip 38.

A vacuum port 44 which is capable of evacuating an interior of the bone cement cartridge 10 in which the bone cement paste 50 is mixed may be arranged in the adapter element 9. As a result, the bone cement paste 50 can be mixed under a vacuum.

A piston 46 for discharging the bone cement paste 50 from the bone cement cartridge through the valve body 6 and the valve seat 3 into the casting mold 1 may be arranged in the cylindrical interior of the bone cement cartridge 10. The piston 46 may to this end be cylindrically shaped on the outside and be sealed relative to the cylindrical interior by means of two circumferential seals 54. By advancing the piston 46, the bone cement paste 50 can be pressed out of the delivery opening 12 of the bone cement cartridge 10 into or through the open valve consisting of the valve body 6 and the valve seat 3.

A porous disk 52 may be arranged in the adapter element 9. The porous disk 52 is impermeable to the bone cement paste 50 and its starting components. The vacuum port 44 can be covered by the porous disk 52. This prevents any bone cement powder as a starting component of the bone cement paste 50 from being able to penetrate into the vacuum port 44.

Figure 3:
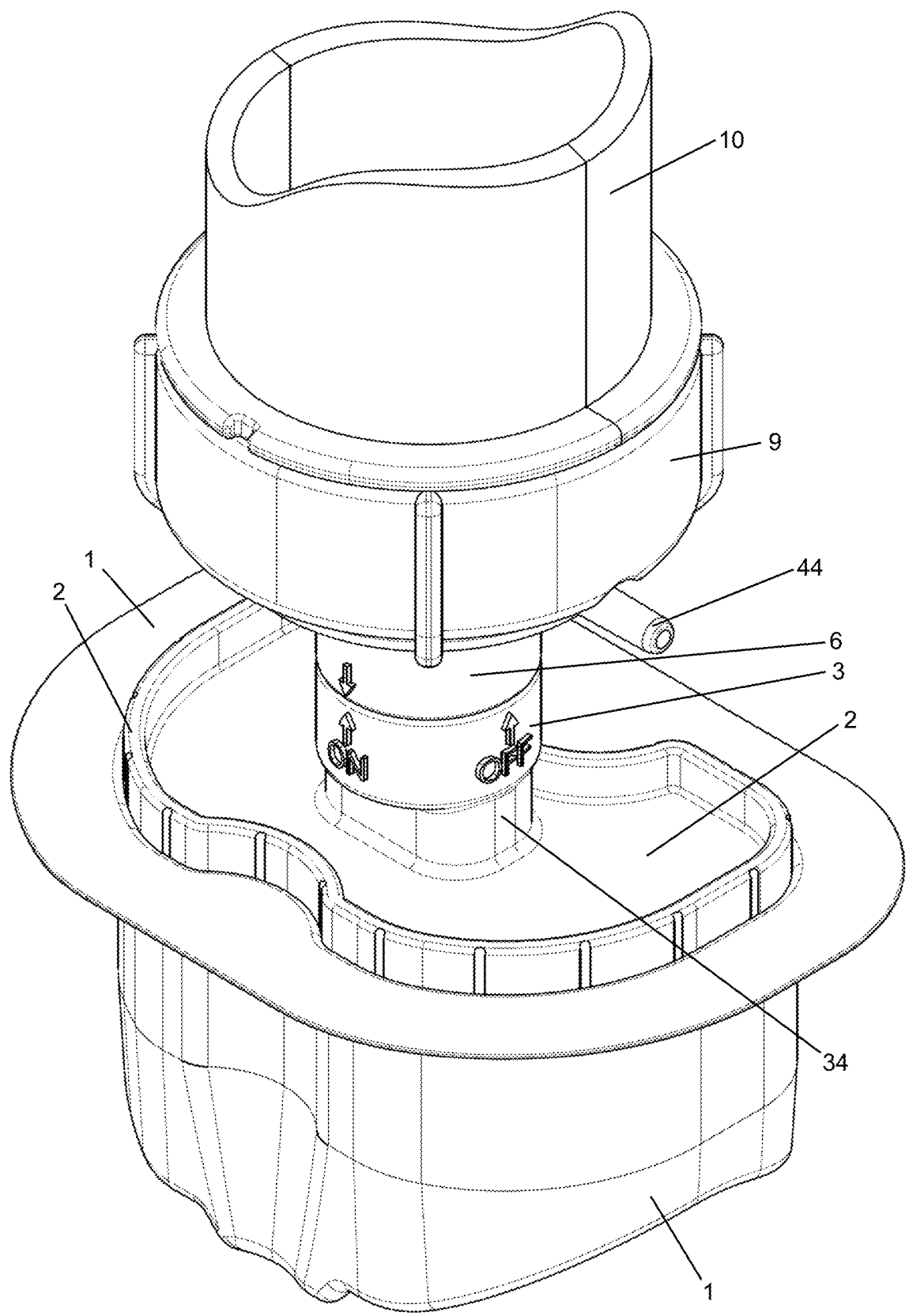
FIG. 3 shows a schematic perspective external view of the first device according to the invention according to FIGS. 1 to 2 with inserted punch.
Figure 4:
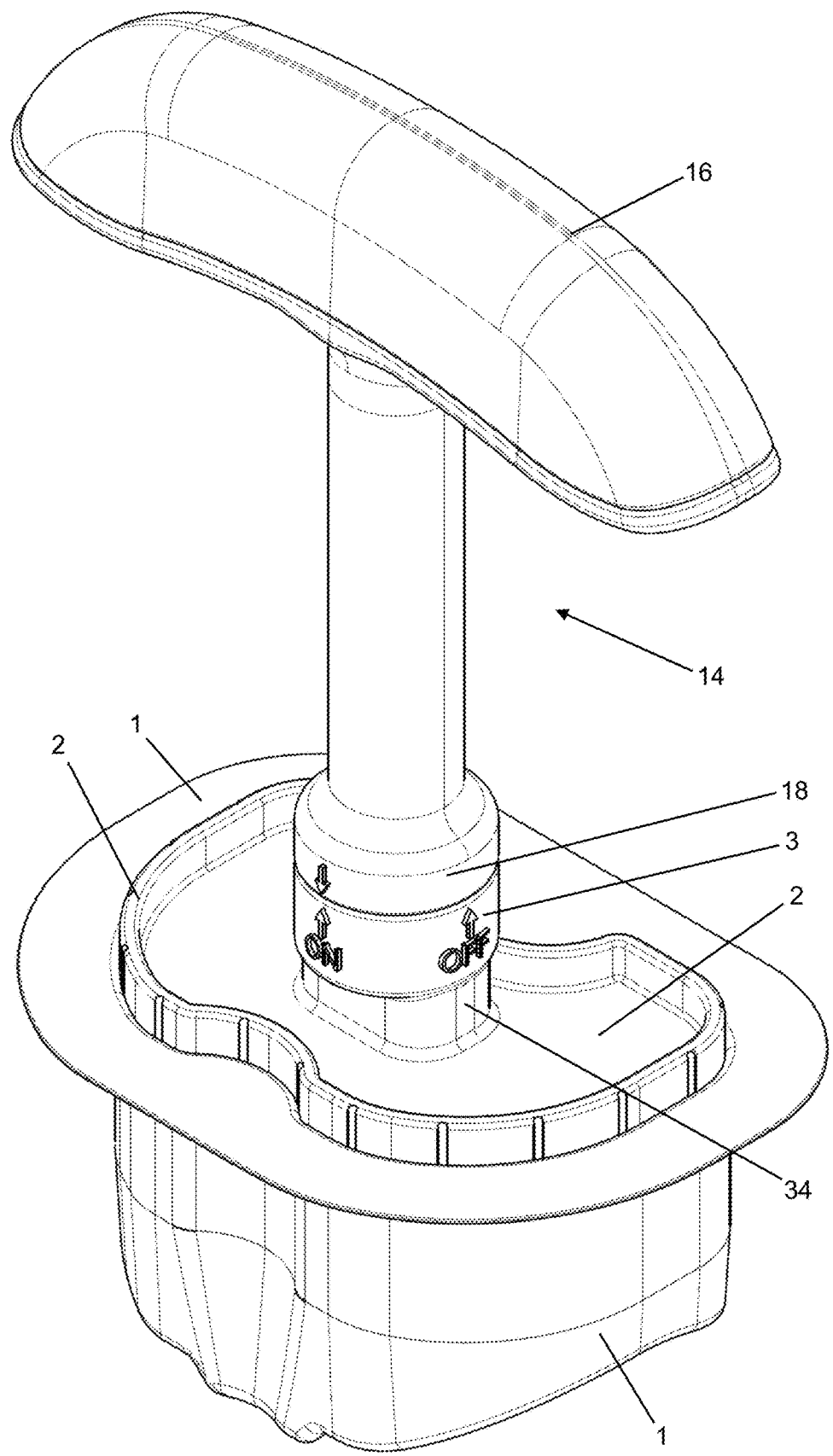
FIG. 4 shows a schematic perspective external view of the first device according to the invention according to FIGS. 1 to 3 with inserted punch.
Figure 6:
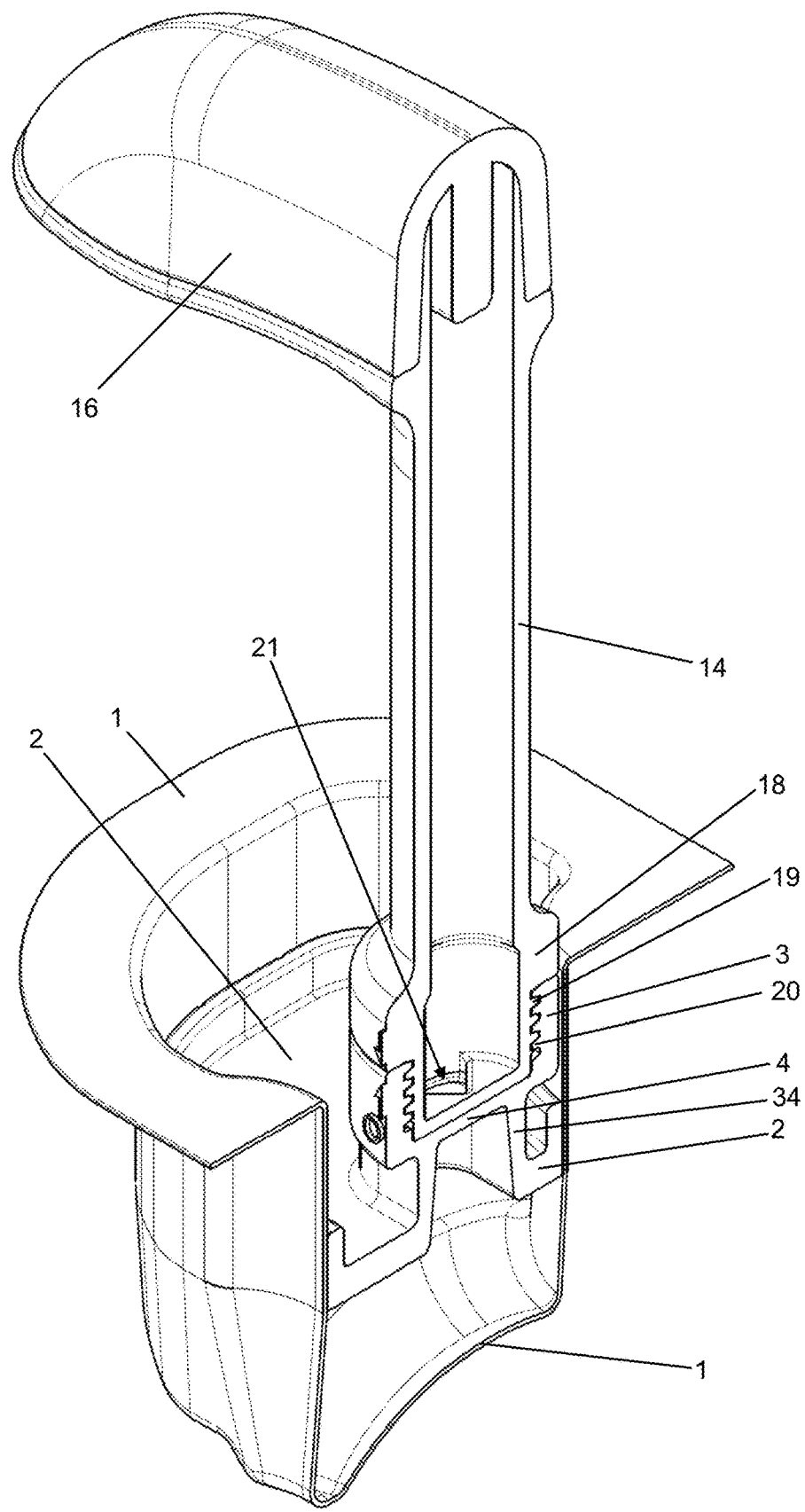
FIG. 6 shows a schematic perspective cross-sectional view of the first device according to the invention with the valve open during forming of the tibial component.
Figure 7:
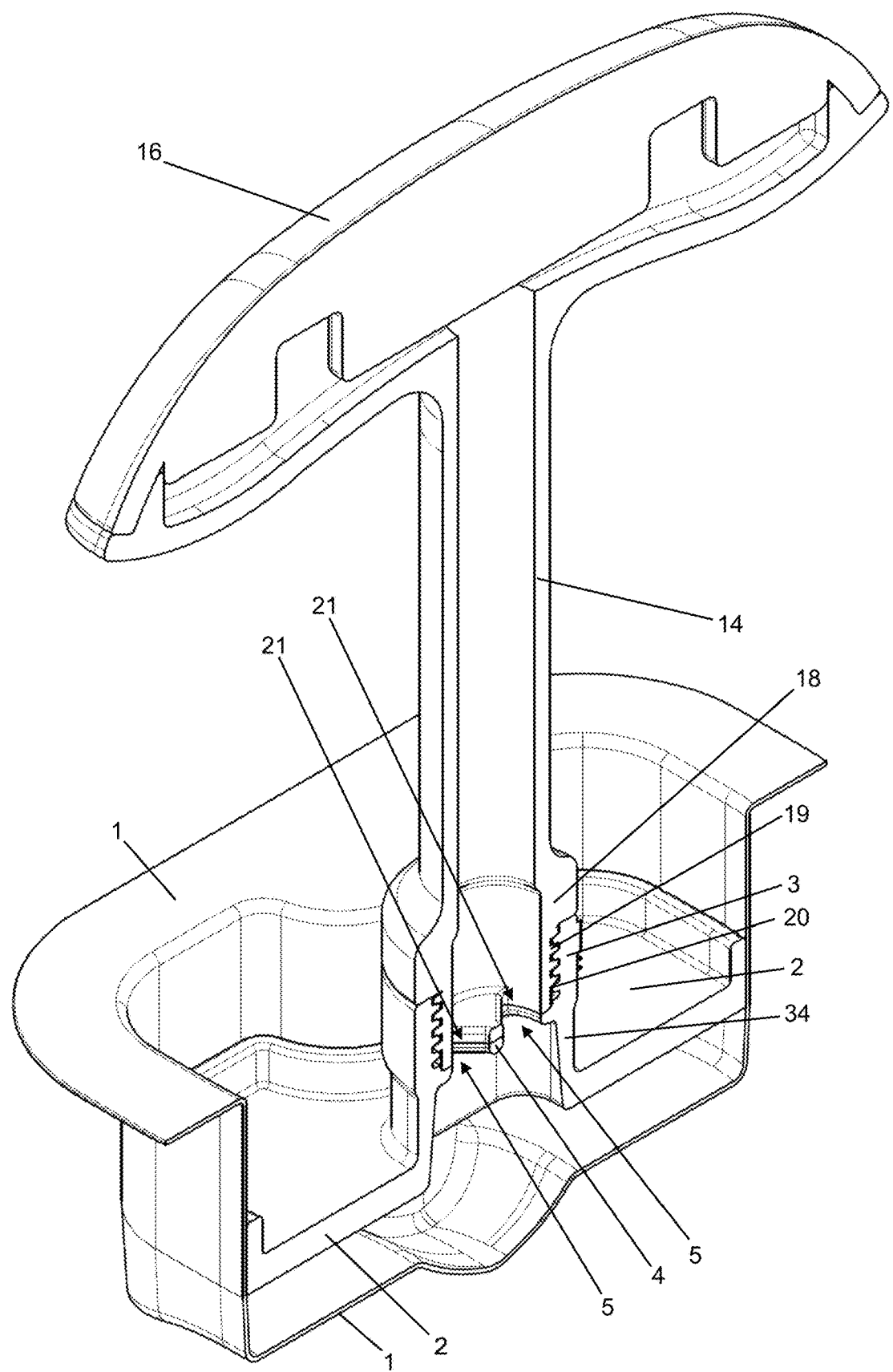
FIG. 7 shows a schematic perspective cross-sectional view of the first device according to the invention with the valve open during forming of the tibial component, wherein the section plane is rotated by 90° relative to FIG. 6.
Figure 8:
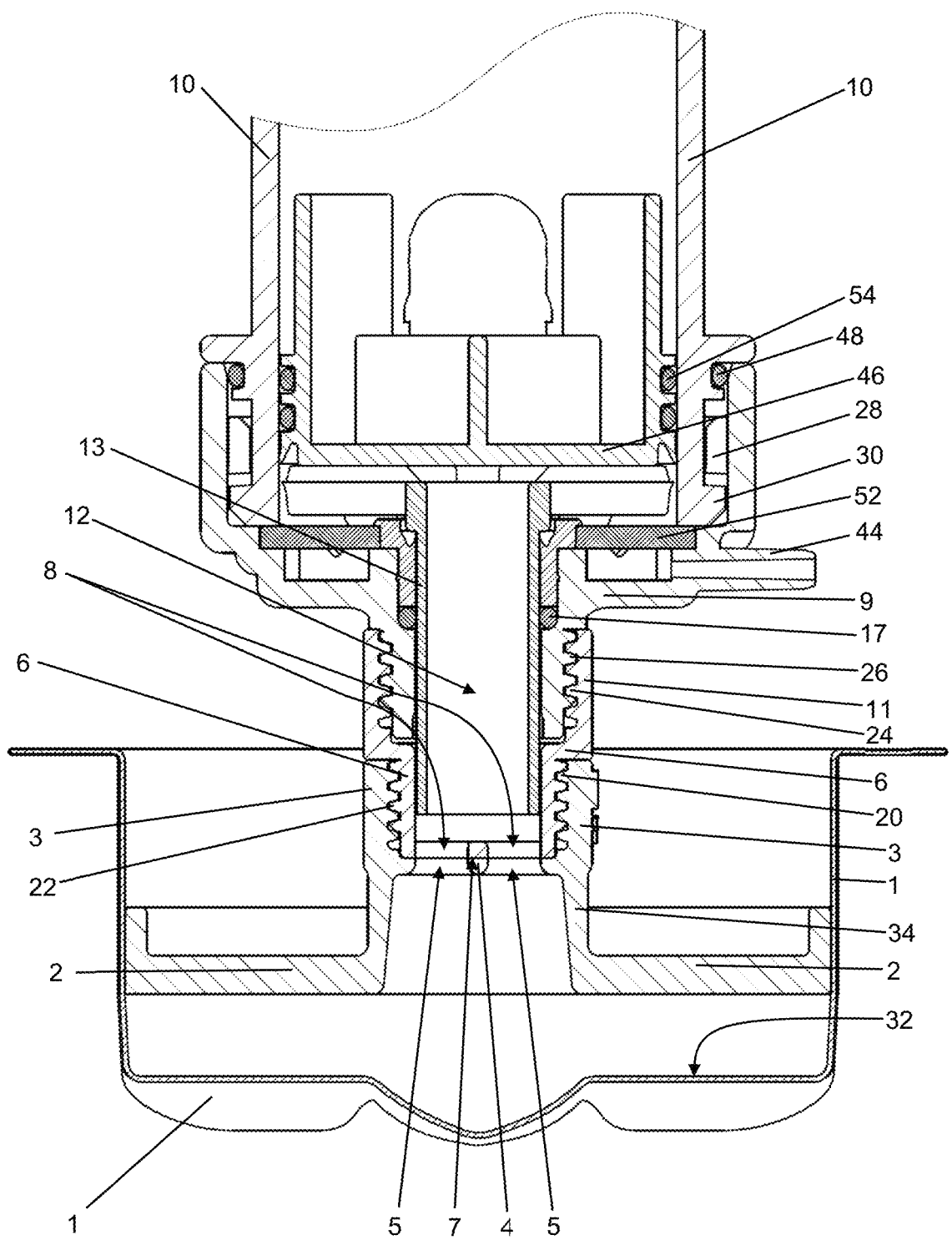
FIG. 8 shows a schematic cross-sectional view of the first device according to the invention with the valve open and a bone cement cartridge connected to the casting mold.

The course of a method according to the invention can be explained with reference to FIGS. 1 to 10 on the basis of the first device according to the invention. A bone cement paste 50 can be mixed under a vacuum in the bone cement cartridge 10. The bone cement cartridge 10 can then be screwed with the adapter element 9 into the port 11 of the valve body 6. On screwing in the adapter element 9, the valve can be transferred into the open position by screwing the valve body 6 into the valve seat 3 until the limit stop is reached. FIGS. 1, 3 and 8 show this situation.

The bone cement paste 50 is then pressed out of the bone cement cartridge 10 through the valve and through the overlapping first feed-throughs 5 and second feed-throughs 8 into the casting mold by advancing the piston 46. In so doing, the punch 2 may be expelled from the trough-shaped mold 1. In order to mold the knee spacer component by pressing the bone cement paste 50 against the inner walls of the casting mold, the user should maintain pressure on the punch 2 via the bone cement cartridge 10 on injection of the bone cement paste 50. By closing the valve by manually operating the grip 38 and so rotating the valve body 6 by a quarter rotation relative to the valve seat 3, a new bone cement cartridge 10 can be attached at intervals if the volume of the bone cement paste 50 from a single bone cement cartridge 10 is not enough to fill the casting mold sufficiently. The bone cement paste 50 contained in the casting mold cannot flow back out again since the first passages 5 and the second passages 8 are covered in the closed position of the valve and the gap therebetween is insufficient for the viscous bone cement paste 50 to be able flow through.

Figure 5:
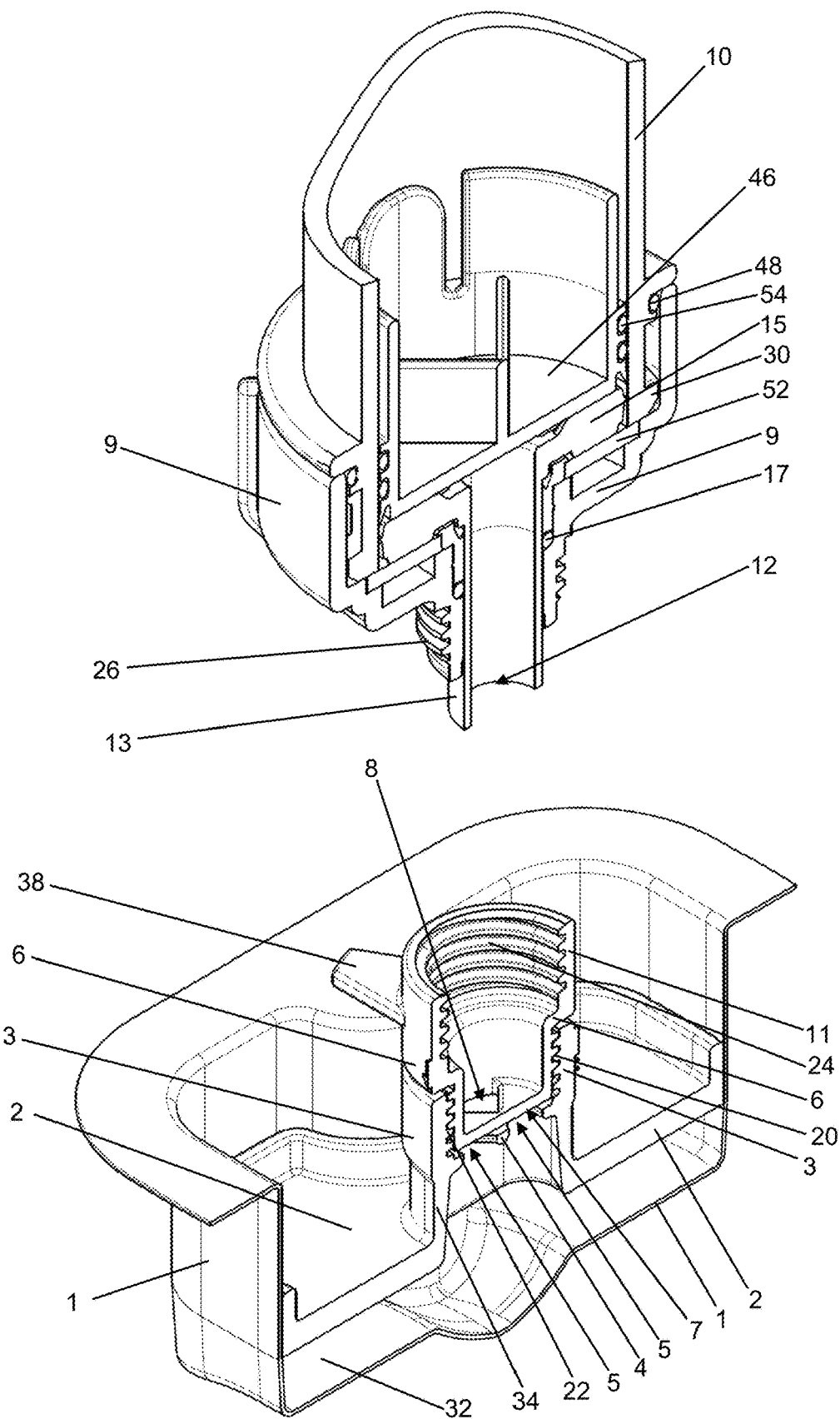
FIG. 5 shows a schematic perspective cross-sectional view of the first device according to the invention with the valve closed.
Figure 9:
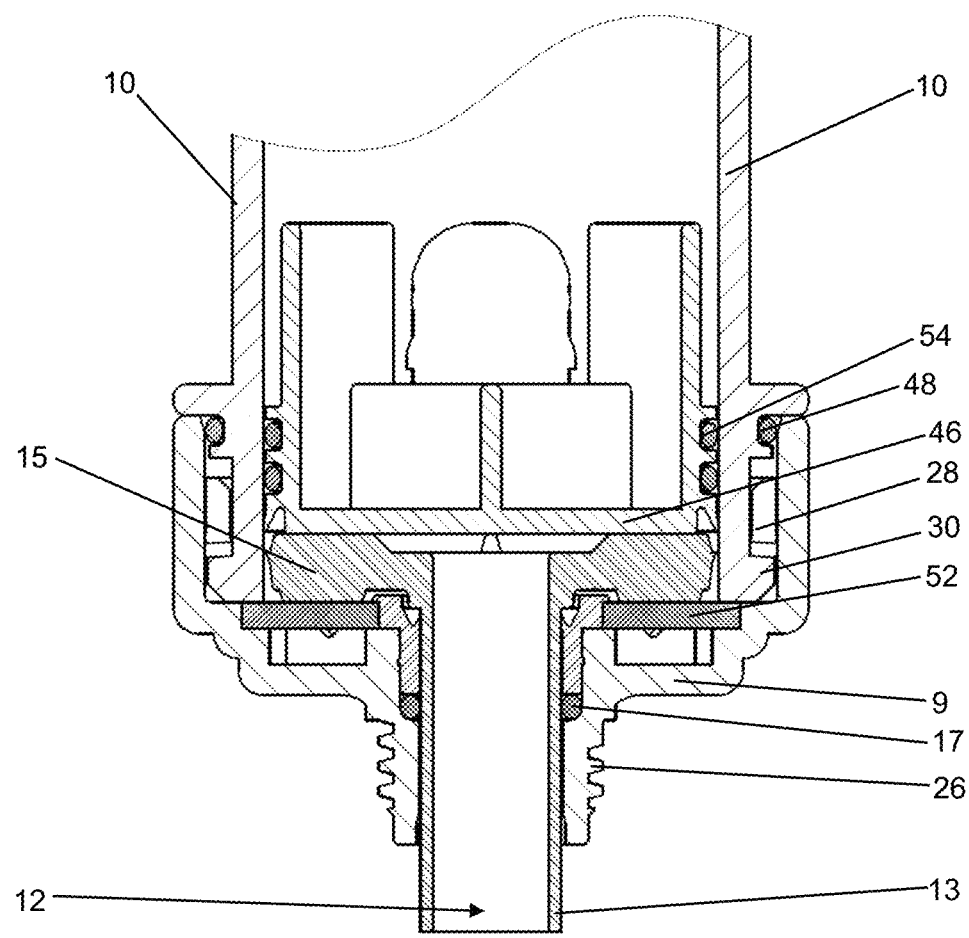
FIG. 9 shows a schematic cross-sectional view of the first device according to the invention with the valve closed and a bone cement cartridge detached from the casting mold.
Figure 9:
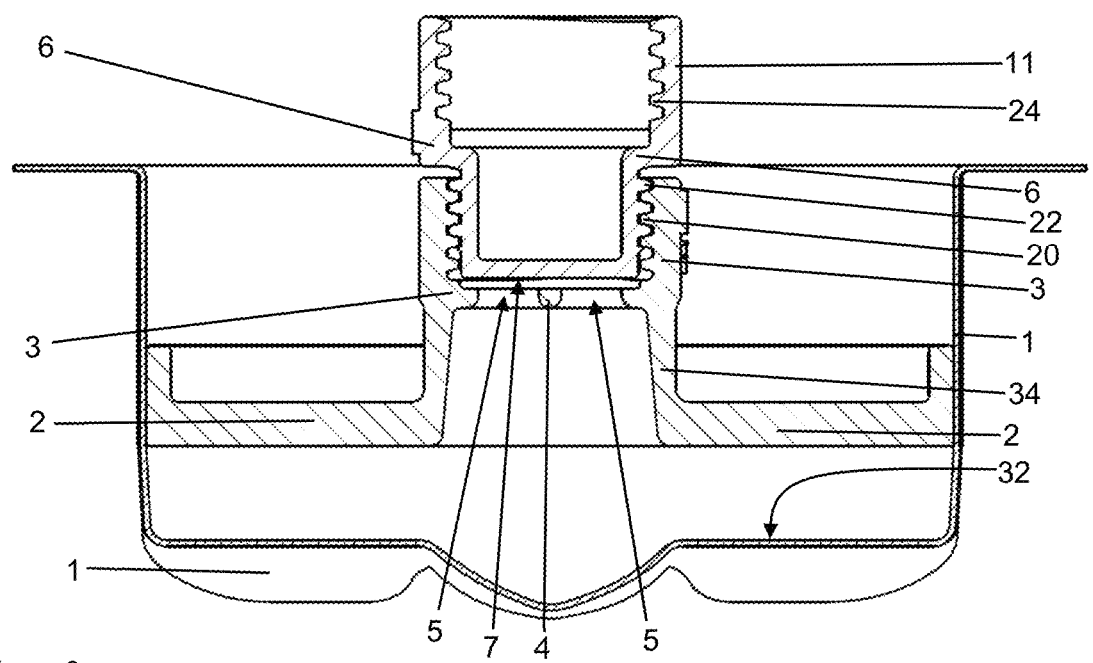

At some point, the casting mold is sufficiently filled with the bone cement paste 50. Air or gas from the casting mold can escape from the casting mold through the gap between the trough-shaped mold 1 and the punch 2. Once the desired height of the knee spacer component has been reached by the punch 2 being expelled by the exactly correct amount out of the trough-shaped mold, the valve can remain closed and the bone cement paste 50 cure in the casting mold in order to produce the knee spacer component. By closing the valve with the grip 38, the bone cement paste 50 is sheared or cut off. The bone cement cartridge 10 can be unscrewed and removed. Any remaining thin connections simply tear or break away. FIGS. 5 and 9 show this situation.

If excess bone cement paste 50 was filled into the casting mold or the height of the knee spacer component is too great, the desired height of the knee spacer component to be produced can be adjusted by screwing the handle 14 into the inner thread 20 of the valve seat 3. The valve body 18 here also forms a new valve with the valve seat 3. The valve is brought into the open position by screwing the handle 14 in until the limit stop is reached. FIGS. 6 and 7 show this situation.

Figure 10:
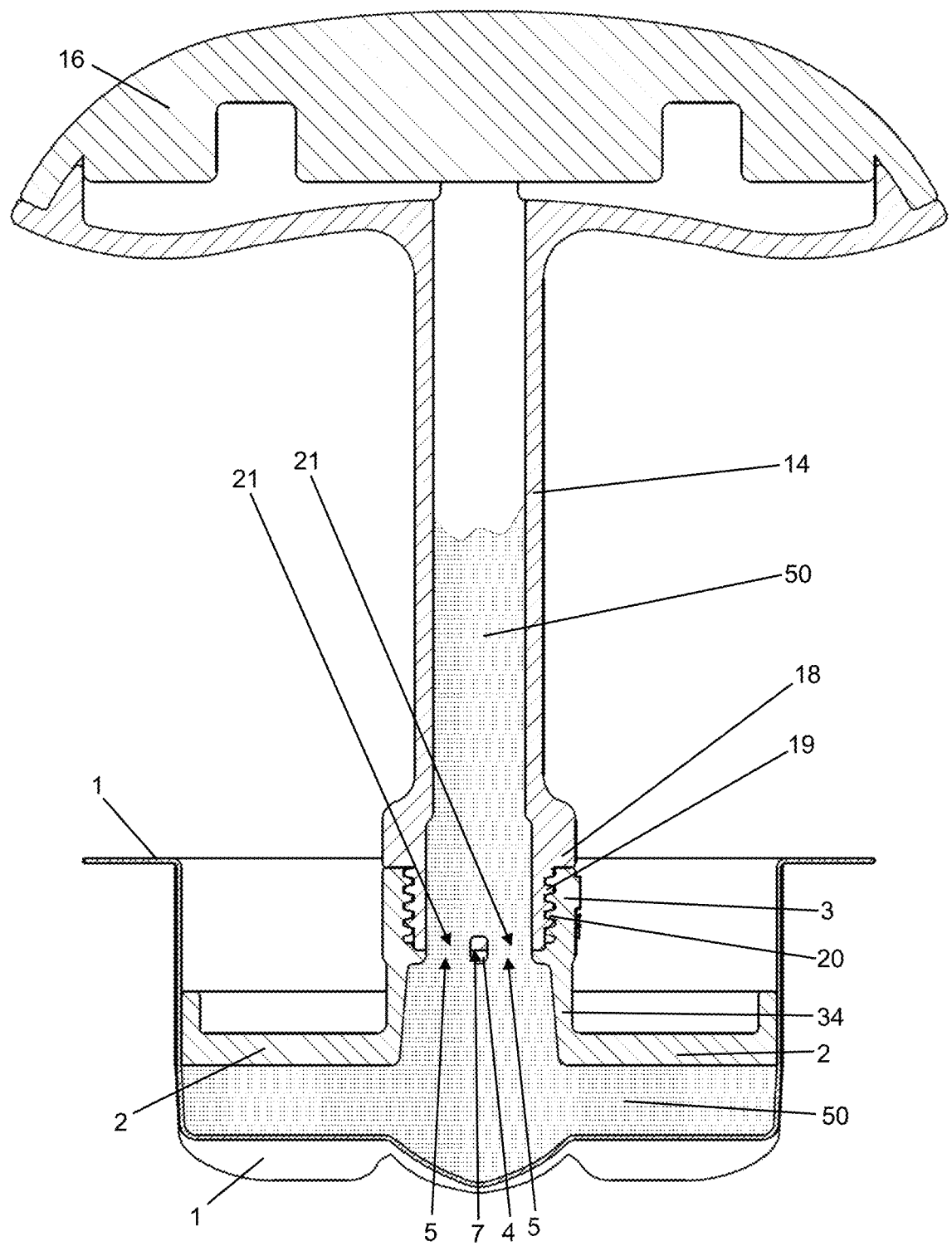
FIG. 10 shows a schematic cross-sectional view of the first device according to the invention with the valve open and the handle connected to the casting mold during forming of a tibial component.

Due to a reduction in the height of the interior of the casting mold by pushing the punch 2 into the trough-shaped mold 1, part of the bone cement paste 50 is expelled from the casting mold and through the two first feed-throughs 5 and the two second feed-throughs 21 into the collecting vessel of the handle 14. This is shown in FIG. 10. The handle 14 is then rotated by a quarter rotation (by 90°) and thus the two second openings 21 are rotated relative to the two first openings 5, so closing the valve. In so doing, the bone cement paste 50 is sheared off or largely sheared off in the valve.

In this state, the bone cement paste 50 can be cured in the casting mold. The tibial component molded in this manner is then removed from the casting mold. Any flash caused by the valve seat 3 and the first passages 5 can be cut off and removed. The surface of the tibial component can be polished and/or coated, for example with antibiotics.

Instead of a casting mold for molding a tibial component, it is also straightforwardly possible to use a casting mold for molding a femoral component.

Figure 14:
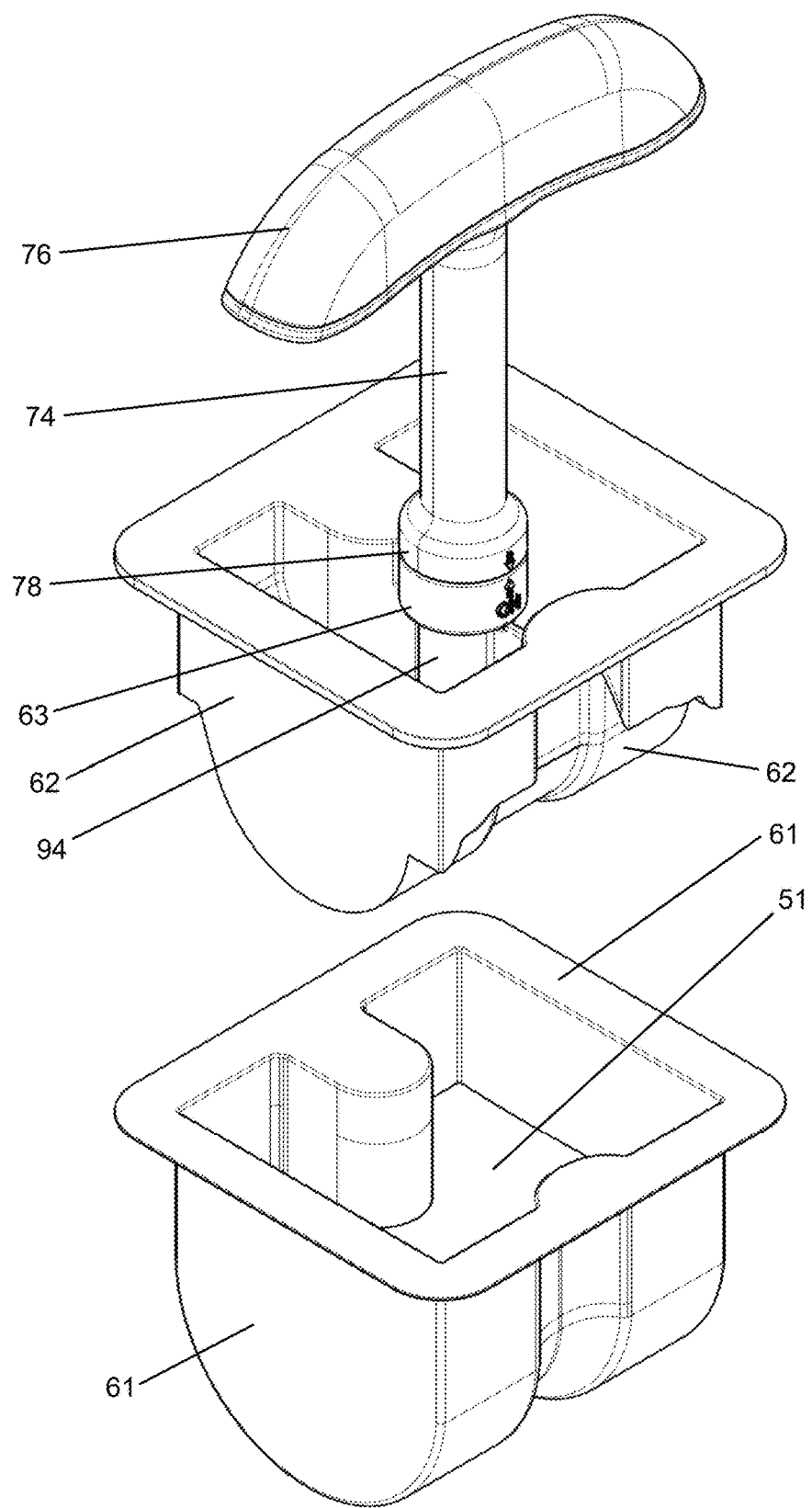
FIG. 14 shows a schematic perspective external view of the parts of the second device according to the invention before forming of the femoral component.
Figure 15:
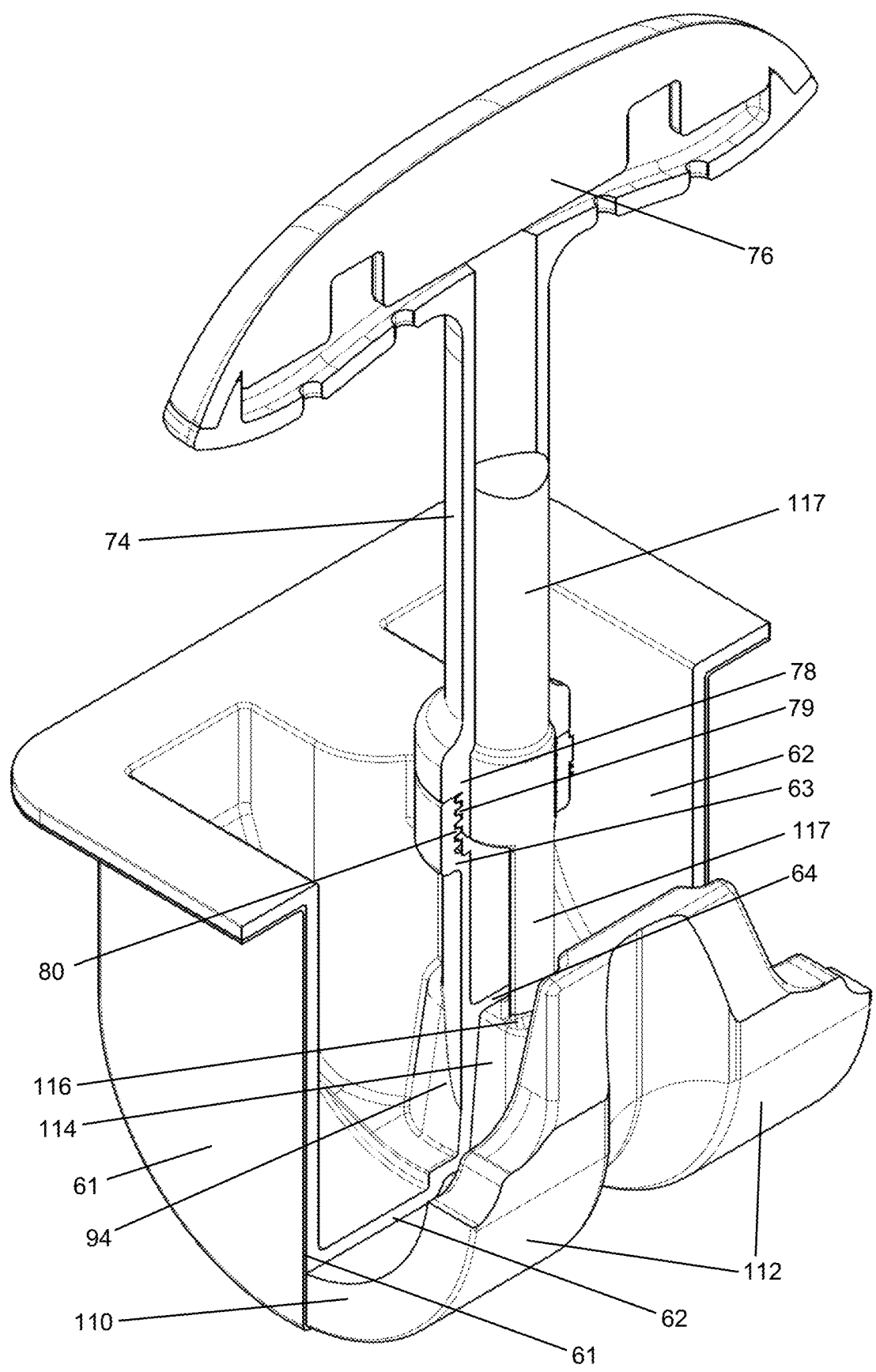
FIG. 15 shows a schematic perspective cross-sectional view of the closed second device according to the invention according to FIGS. 11 to 14 and the femoral component contained therein.
Figure 16:
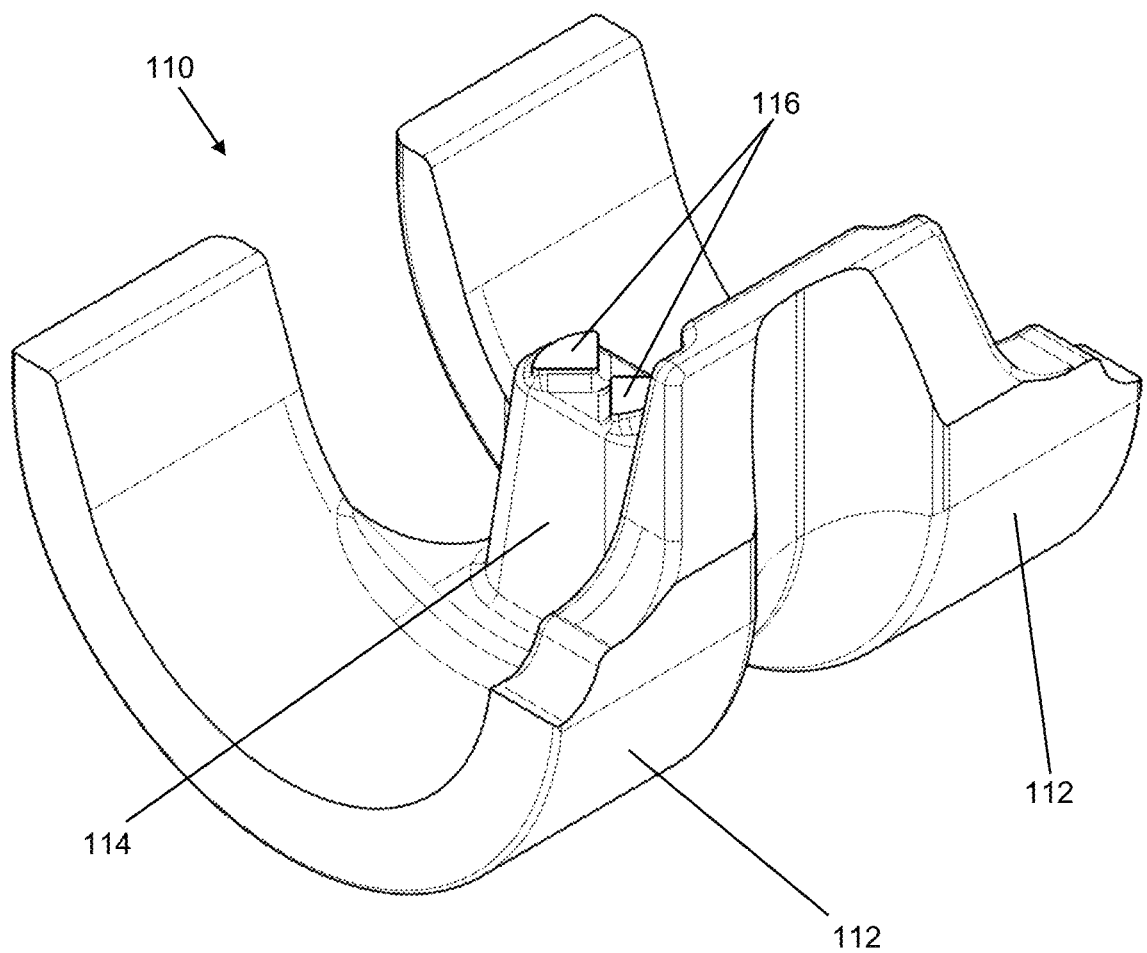
FIG. 16 shows a perspective view of a femoral component which has been produced using a second device according to the invention according to FIGS. 11 to 15.
Figure 17:
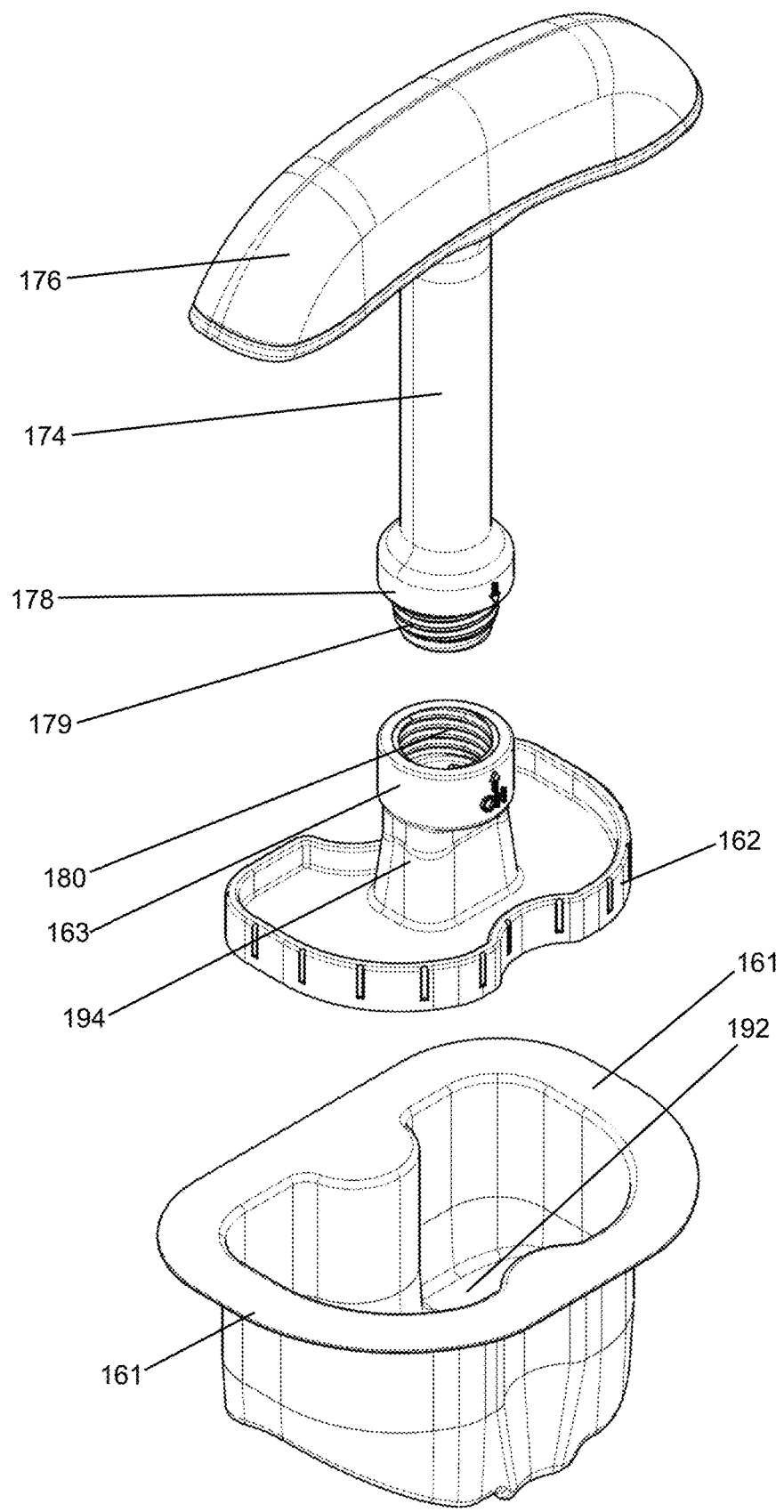
FIG. 17 shows a schematic perspective external view of a third exemplary device according to the invention for producing a tibial component.

FIGS. 11 to 15 are drawings of a second exemplary embodiment of a device according to the invention for producing a knee spacer component 110 in the form of a femoral component for a knee spacer and parts of the device, in various views. FIG. 16 shows the knee spacer component 110 which has been produced using such a second device according to the invention as the result of a method according to the invention, the method steps of which are shown chronologically in FIGS. 13 to 16.

The second device according to the invention is suitable and provided for producing a femoral component of a knee spacer. The device comprises a casting mold which is composed of two parts. The casting mold may have a trough-shaped mold 61 and a punch 62. The punch 62 can be inserted into the trough-shaped mold 61 and can be pushed into the trough-shaped mold 61 and preferably also withdrawn again. The trough-shaped mold 61 can be inexpensively fabricated from plastics film. The plastics film may have a plurality of layers. An opening for throughflow of bone cement paste 51, which may be delimited by a cylindrical wall of the punch 62, may be formed on one side of the punch 62. A valve seat 63 may be arranged in this opening. The valve seat 63 may be firmly connected to the punch 62 of the casting mold or even be formed as one part, as shown in FIGS. 11 to 15.

The valve seat 63 may take the form of a hollow cylinder which, apart from two first feed-throughs 65, is closed on a head side 64 oriented in the direction of the opening in the punch 62. The two first feed-throughs 65 may be quadrant-shaped and may preferably be arranged rotated or offset relative to one another by 180° with regard to the cylinder axis of the valve seat 63.

A valve body 78 may be or have been arranged in the interior of the valve seat 63 so as to be axially rotatable relative to the valve seat 63. The valve body 78 may have a sealing face 67 or surface oriented in the direction of the head side 64 of the valve seat 63, which sealing face may be delimited by a closing pin 82 for closing the two first feed-throughs 65.

Two second feed-throughs 68 may be arranged in the valve body 78. The two second feed-throughs 68 may, similarly to the first feed-throughs 65, be quadrant-shaped and may preferably be arranged rotated relative to one another by 180° with regard to the cylinder axis of the valve body 78. The valve seat 63 and valve body 78 together form a valve of the device.

The device may have a handle 74 which forms a handgrip 76 at one end (see FIGS. 11, 12, 14 and 15). The valve body 78 with an outer thread 79 may be arranged at the opposite end of the handle 74. The valve body 78 may be or have been arranged in the valve seat 63 so as to be axially rotatable relative to the valve seat 63 by means of the handle 74 (see FIGS. 14 and 15). The valve body 78 may have the closing pin 82 oriented in the direction of the head side 64 of the valve seat 63, which closing pin forms the sealing face 67 of the valve body 78. The valve body 78 may be screwed or put into the valve seat 63.

The handle 74 may have a hollow interior. The cavity in the interior of the handle 74 may be connected to the two second feed-throughs 68 of the handle 74. As a result, the cavity in the interior of the handle may form a collecting vessel for receiving excess bone cement 117, wherein the excess bone cement paste 51 from the casting mold can flow through the two second feed-throughs 68 into the collecting vessel when the valve formed by the valve body 78 and the valve seat 63 is in an open position in which the two first feed-throughs 65 in the valve seat 63 are connected liquid-permeably for the bone cement paste 51 to the two second feed-throughs 68 or are arranged above one another.

The punch 62 can be pushed into the trough-shaped mold 61. The casting mold can be closed to the outside by putting the punch 62 into the trough-shaped mold 61. When the trough-shaped mold 61 and the punch 62 are nested in one another, a gap may be present for venting the interior of the casting mold (not visible in FIGS. 11 to 15). Air or gas can escape through the gap from the interior of the closed casting mold when a bone cement paste 51 is filled into the casting mold.

The valve seat 63 may have an inner thread 80 on its inside. The outer thread 79 of the handle 74 matches the inner thread 80 of the valve seat 63, such that the valve body 78 can be screwed into the valve seat 63.

The first feed-throughs 65 and the second feed-throughs 68 may be brought into overlap with one another by screwing the valve body 78 into the valve seat 63 until the limit stop is reached. The valve is then in the open state. In this open state, a bone cement paste 51 may flow through the first feed-throughs 65 and through the second feed-throughs 68 out of the casting mold into the collecting vessel in the handle 74.

By making a quarter rotation (by 90°) of the valve body 78 relative to the valve seat 63, i.e. by unscrewing the valve body 78 from the valve seat 63, the first feed-throughs 65 and the second feed-throughs 68 may be offset relative to one another, such that the sealing face 67 of the valve body 78 covers the first feed-throughs 65 of the valve seat 63 and the closed regions of the head side 64 of the valve seat 63 cover the second feed-throughs 68 of the valve body 78. The valve is then in the closed state. Due to the small stroke of the valve body 78 relative to the valve seat 63 in the event of a quarter rotation, the gap arising between the valve body 78 and the valve seat 63 is so narrow (less than 1 mm wide) that a bone cement paste 51 of a normal, let alone high, viscosity, is incapable of passing through the gap. This is particularly the case because the bone cement paste 51 is deflected from its actual direction of flow by 90° in the gap.

The inner thread 80 of the valve seat 63 and the outer thread 79 of the valve body 78 may all have the same direction of rotation, i.e., all these threads are right-hand threads or left-hand threads. As a result, the valve may be opened by screwing the handle 74 into the valve seat 63. At the same time, the valve body 78 provides a seal relative to the valve seat 63.

The casting mold may have a bottom plate 92 for molding a sliding surface of a knee spacer component 110 molded with the casting mold. In the present case, this may be a sliding surface 112 of structures of the femoral component which replicate the condyles of a femur (see FIG. 16). The knee spacer component 110 may additionally have a stem 114 and, on the stem 114, a piece of flash 116. The bottom plate 92 may form the base or bottom of the trough-shaped mold 61. The punch 62 can be pushed into the trough-shaped mold 61 in the direction of the bottom plate 92. As a result, a bone cement paste 51 filled into the casting mold can be pressed against the bottom plate 92 of the trough-shaped mold 61. The casting mold and in particular the punch 62 of the casting mold may further have a stem molding 94 for forming the stem 114 of the knee spacer component 110.

Figure 11:
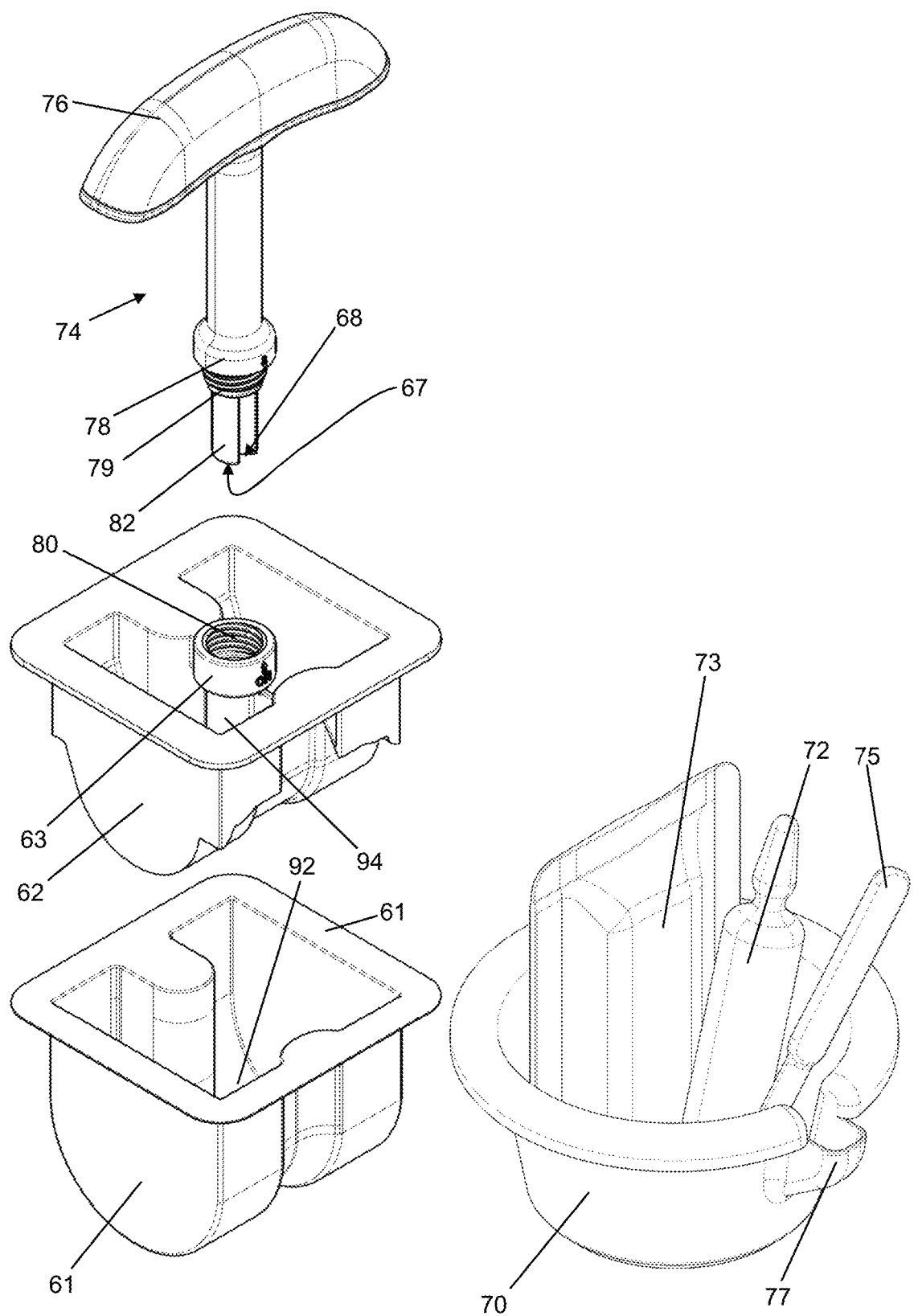
FIG. 11 shows a schematic perspective view of an exemplary second device according to the invention for producing a femoral component.
Figure 12:
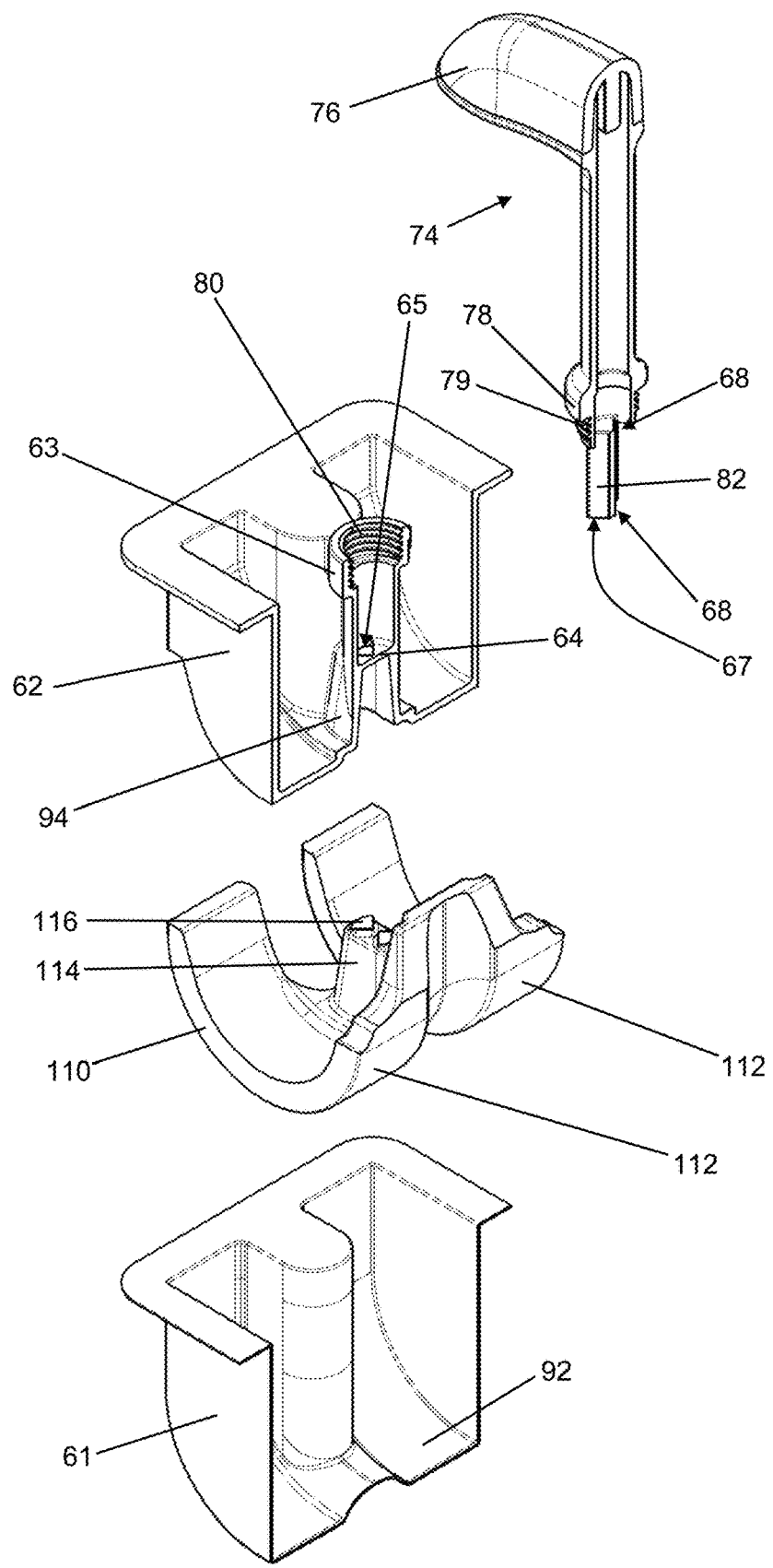
FIG. 12 shows a schematic perspective cross-sectional view through the parts of the second device according to the invention according to FIG. 11 with a femoral component produced therewith.
Figure 13:
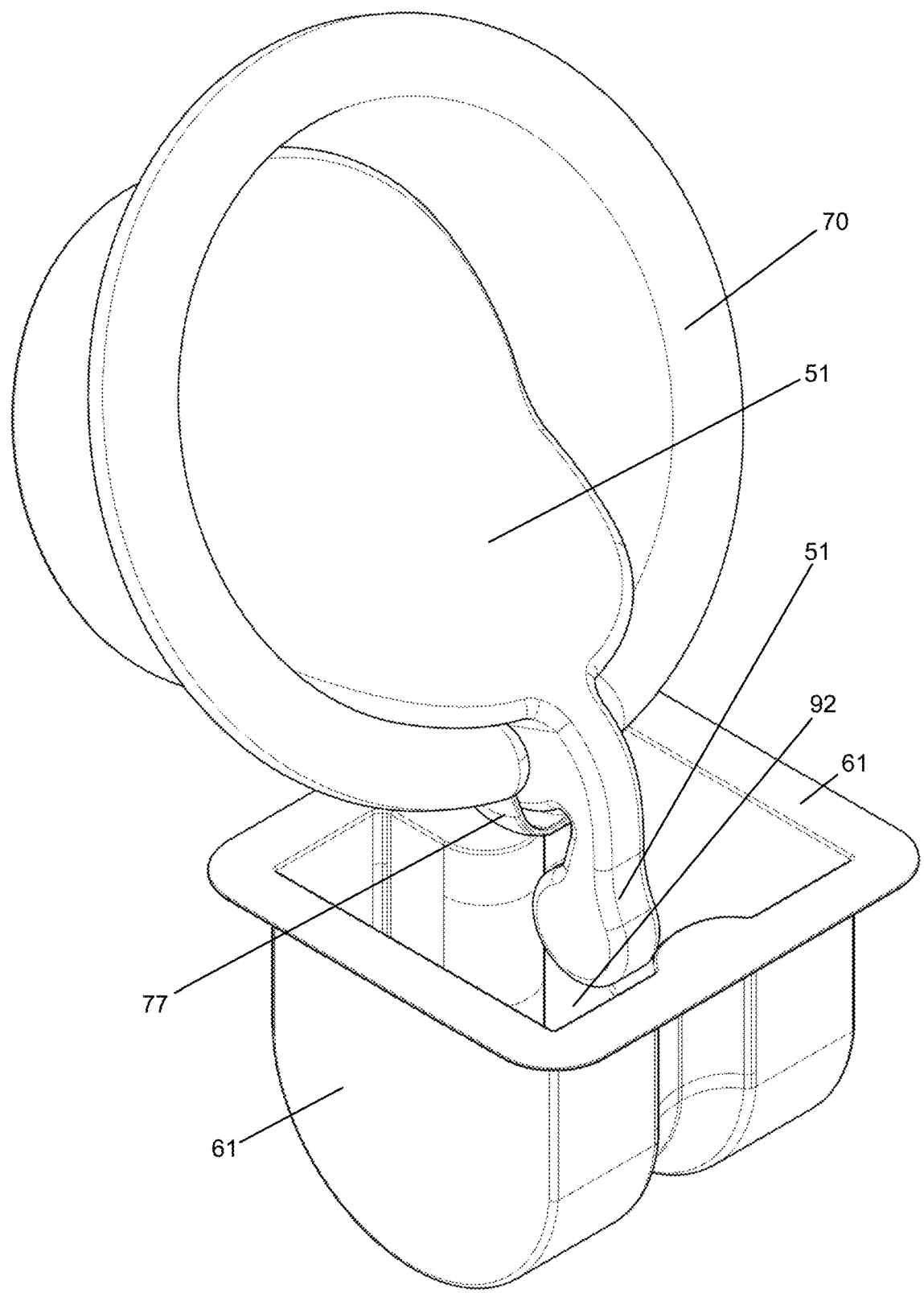
FIG. 13 shows filling bone cement paste into part of the casting mold of the second device according to the invention.

The bone cement paste 51 may be mixed in a mixing cup 70 (see FIGS. 11 and 13). The device may to this end have a monomer liquid container 72 containing monomer liquid and a bone cement powder container 73 containing bone cement powder. The bone cement paste 51 may be mixed in the mixing cup 70 from the bone cement powder and the monomer liquid. The device may have a spatula 75 or another mixing tool for mixing the bone cement paste 51 in the mixing cup 70. The monomer liquid container 72 may be a glass ampoule. The mixing cup 70 may have a spout 77 for pouring out the bone cement paste 51. The mixed bone cement paste 51 may be filled from the mixing cup 70 via the spout 77 of the mixing cup 70 into the trough-shaped mold 61 (see FIG. 13).

Alternatively, a bone cement cartridge may also be used for producing and filling a bone cement paste into the trough-shaped mold 61 or into the casting mold in a similar manner to the first exemplary embodiment according to FIGS. 1 to 10.

The course of a method according to the invention is explained below with reference to FIGS. 13 to 16 on the basis of the second device according to the invention. A bone cement paste 51 may be mixed in the mixing cup 70. The bone cement powder from the bone cement powder container 73 and the monomer liquid from the monomer liquid container 72 are to this end filled into the mixing cup 70 and there mixed with the spatula 75 or with another auxiliary means until the bone cement paste 51 is obtained. The mixed bone cement paste 51 mixed in this manner is then filled from the mixing cup 70 via the spout 77 into the trough-shaped mold 61 (see FIG. 13).

The handle 74 may now be screwed into the inner thread 80 of the valve seat 63 to adjust the desired height of the knee spacer component 110 to be produced. The valve body 78 here forms a valve with the valve seat 63. The valve is brought into the open position by screwing the handle 74 in until the limit stop is reached. FIG. 14 shows this situation.

Due to a reduction in the height of the interior of the casting mold by pushing the punch 62 into the trough-shaped mold 61, part of the bone cement paste 51 is expelled from the casting mold and through the two first feed-throughs 65 and the two second feed-throughs 68 into the collecting vessel of the handle 74. This is shown in FIG. 15. The handle 74 is then rotated by a quarter rotation (by 90°) and thus the two second openings 68 are rotated relative to the two first openings 65, so closing the valve. In so doing, the bone cement paste 51 is sheared off or largely sheared off in the valve. In this way, the excess bone cement 117 held in the collecting vessel of the handle 74 may be removed from the knee spacer component 110 or from the bone cement paste 51 forming the knee spacer component 110 in the casting mold.

In this state, the bone cement paste 51 can be cured in the casting mold. The knee spacer component 110 molded in this manner is then removed from the casting mold (see FIG. 16). Any flash 116 caused by the valve seat 63 and the first passages 65 can be cut off and removed. The surface of the knee spacer component 110 can be polished and/or coated, for example with antibiotics.

Instead of a casting mold for molding a femoral component, it is also straightforwardly possible to use a casting mold for molding a tibial component.

Figure 22:
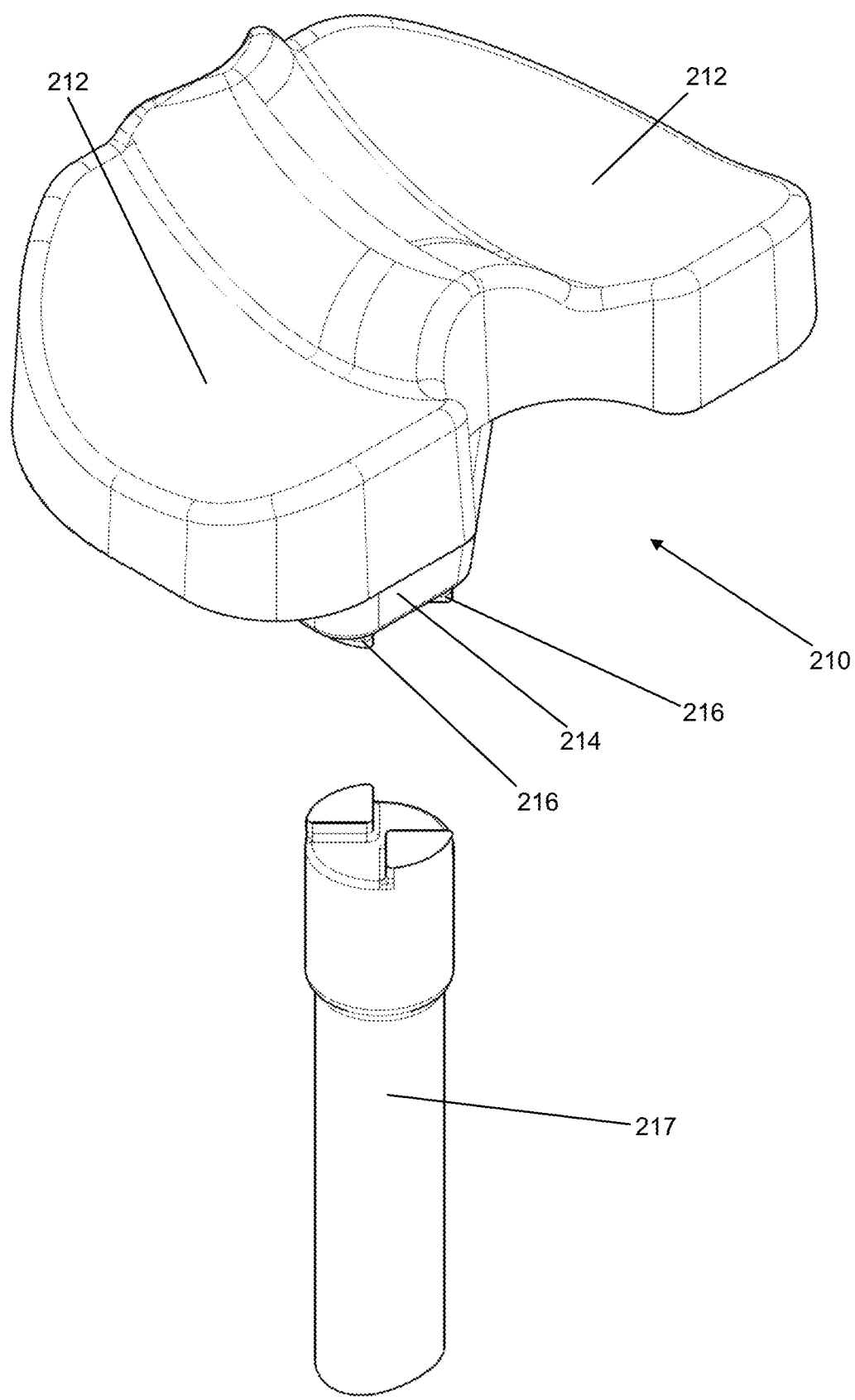
FIG. 22 shows a perspective view of a tibial component which has been produced using a third device according to the invention according to FIGS. 17 to 21, together with a bone cement residue.
Figure 23:
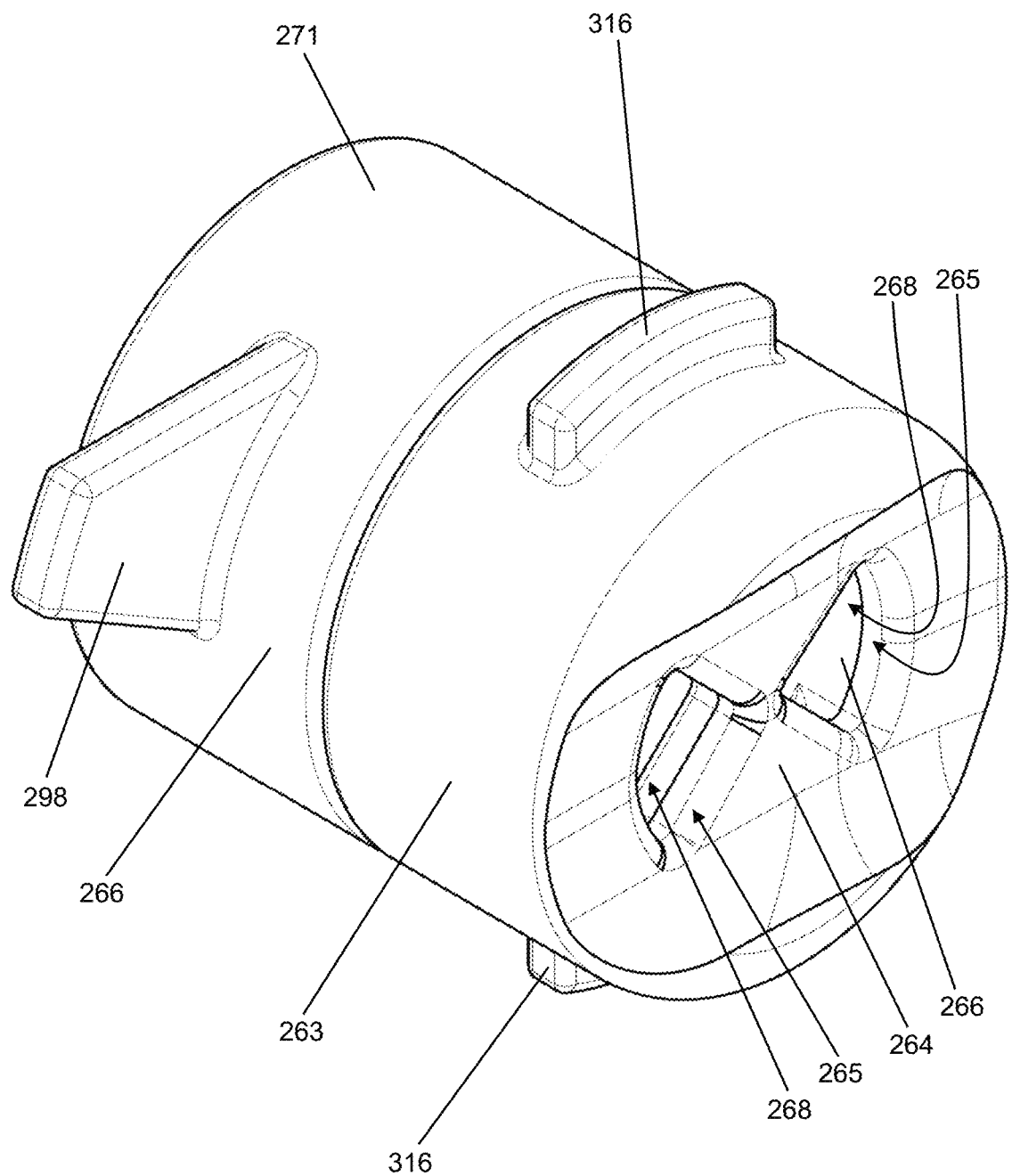
FIG. 23 shows a schematic perspective view of a valve for a device according to the invention in the open state.
Figure 24:
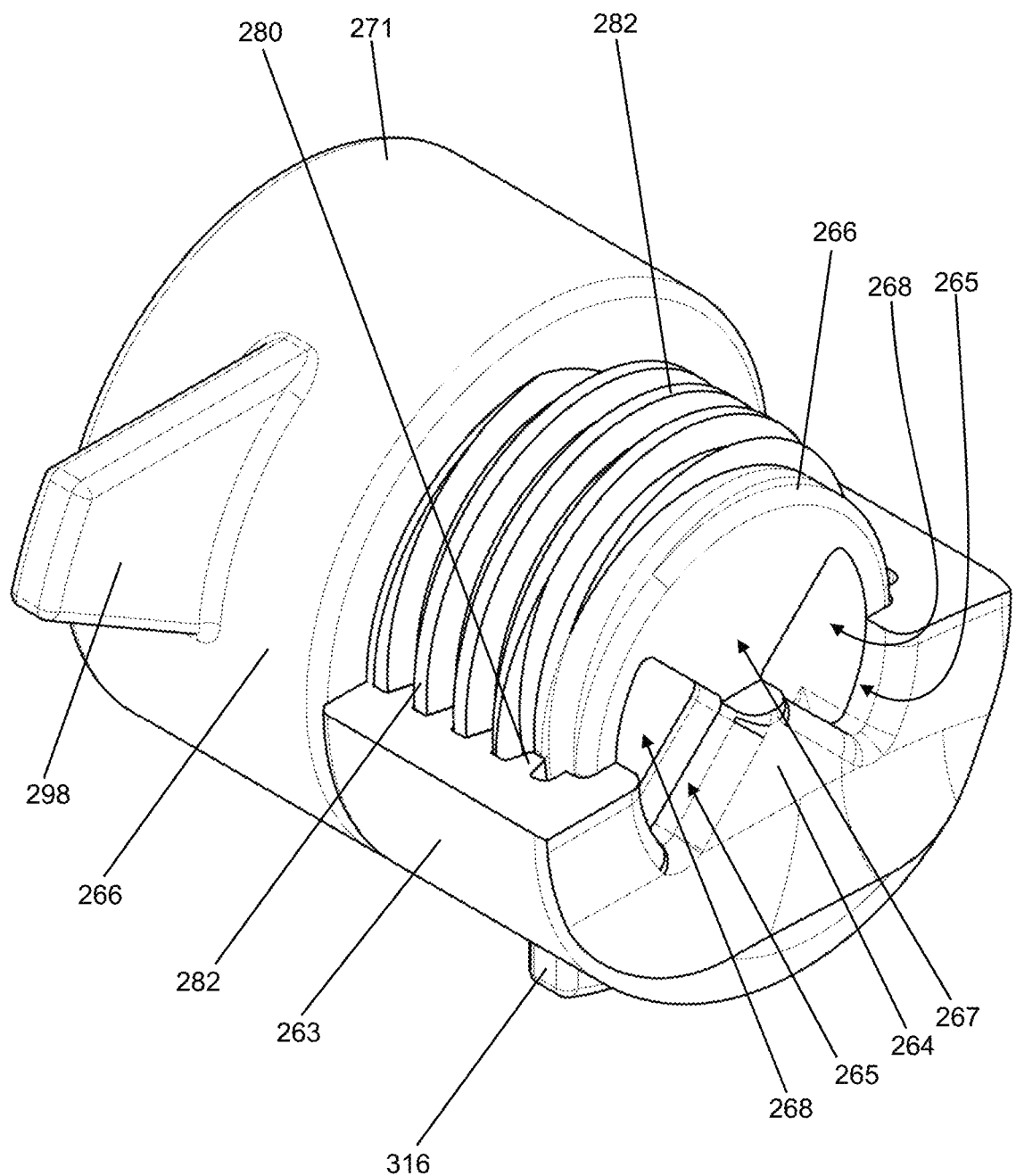
FIG. 24 shows a schematic perspective partial cross-sectional view of the valve according to FIG. 23 in the open state.
Figure 25:
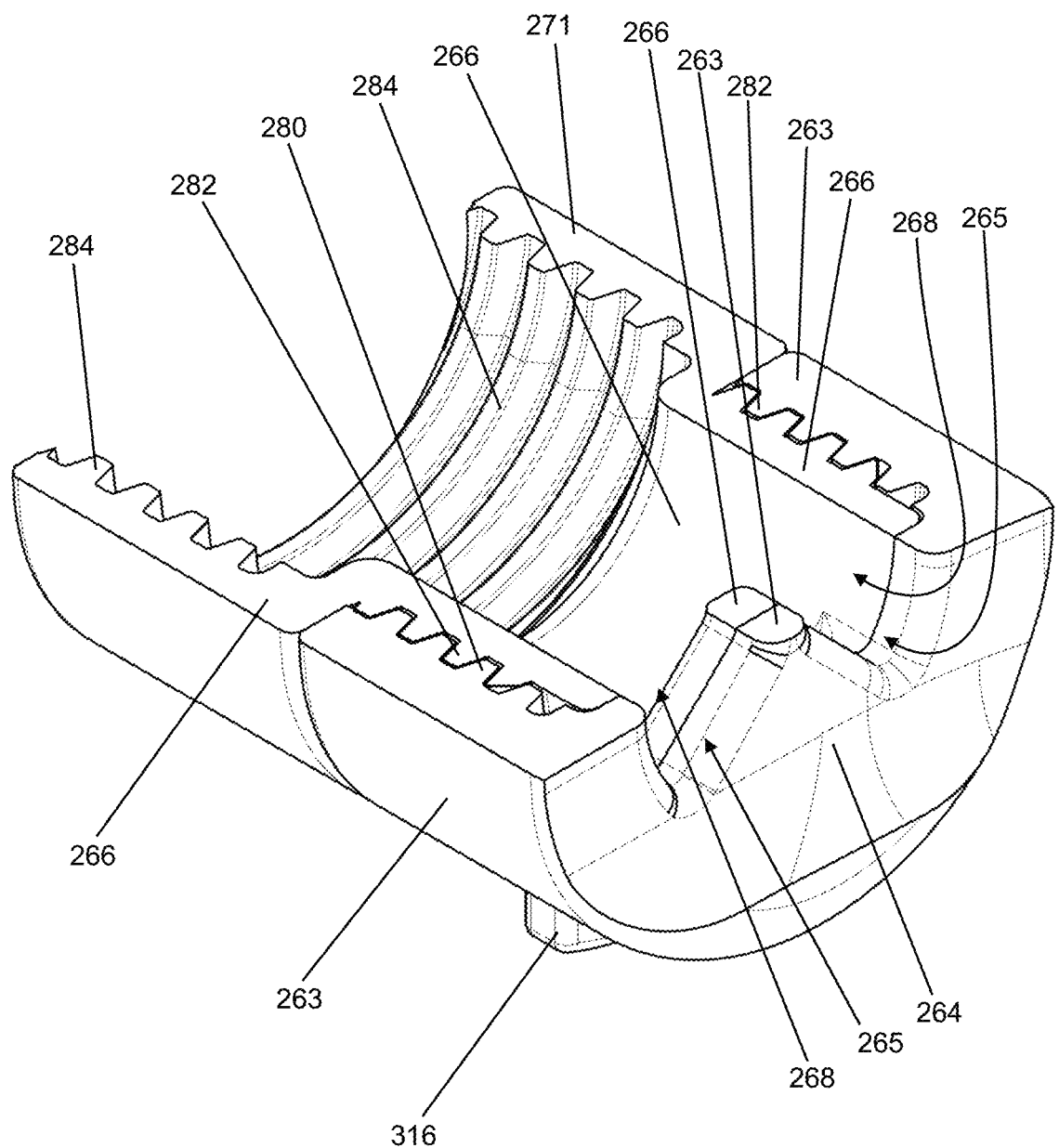
FIG. 25 shows a schematic perspective cross-sectional view through the valve according to FIGS. 23 and 24 in the open state.
Figure 26:
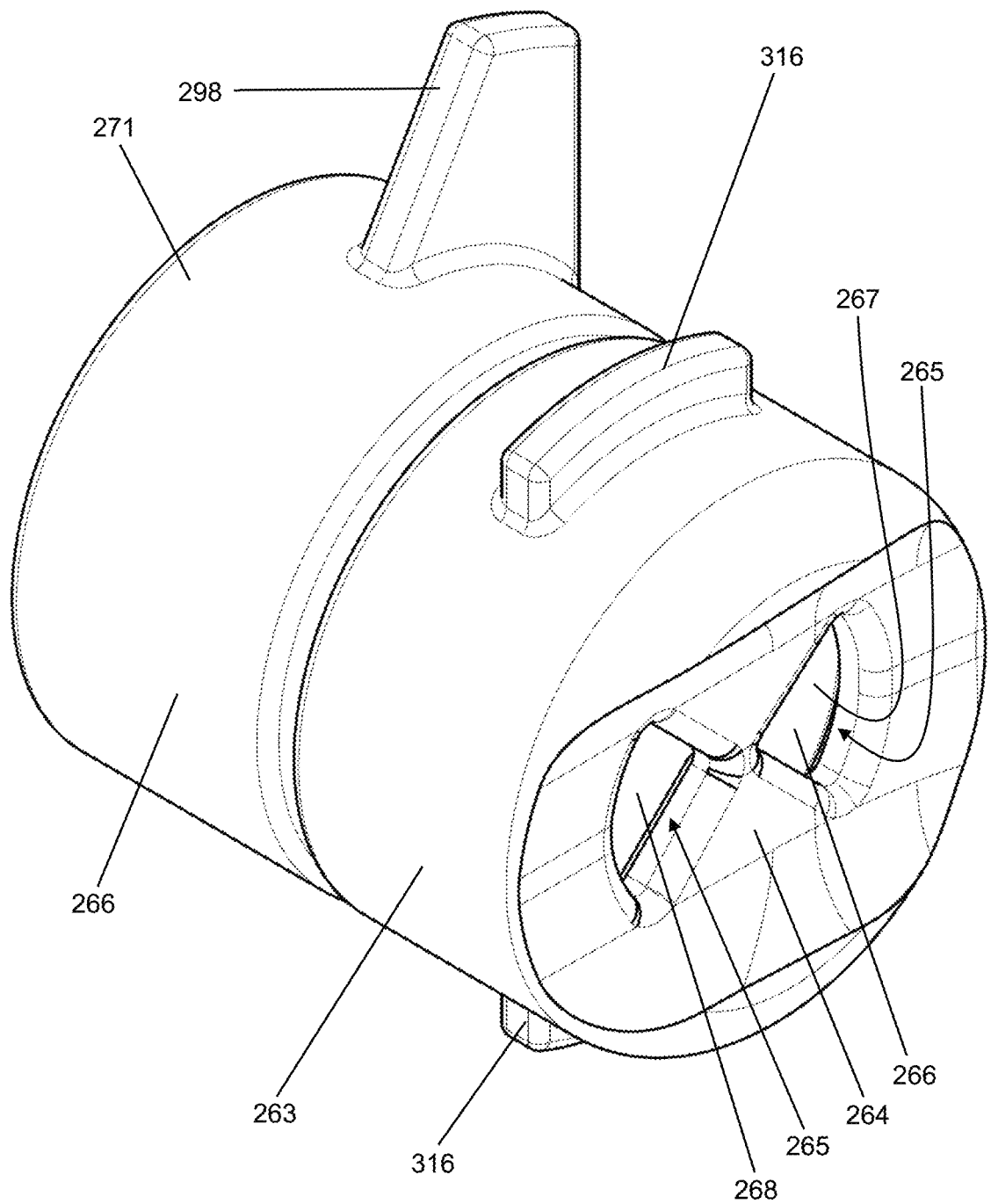
FIG. 26 shows a schematic perspective view of the valve according to FIGS. 23 to 25 in the closed state.
Figure 27:
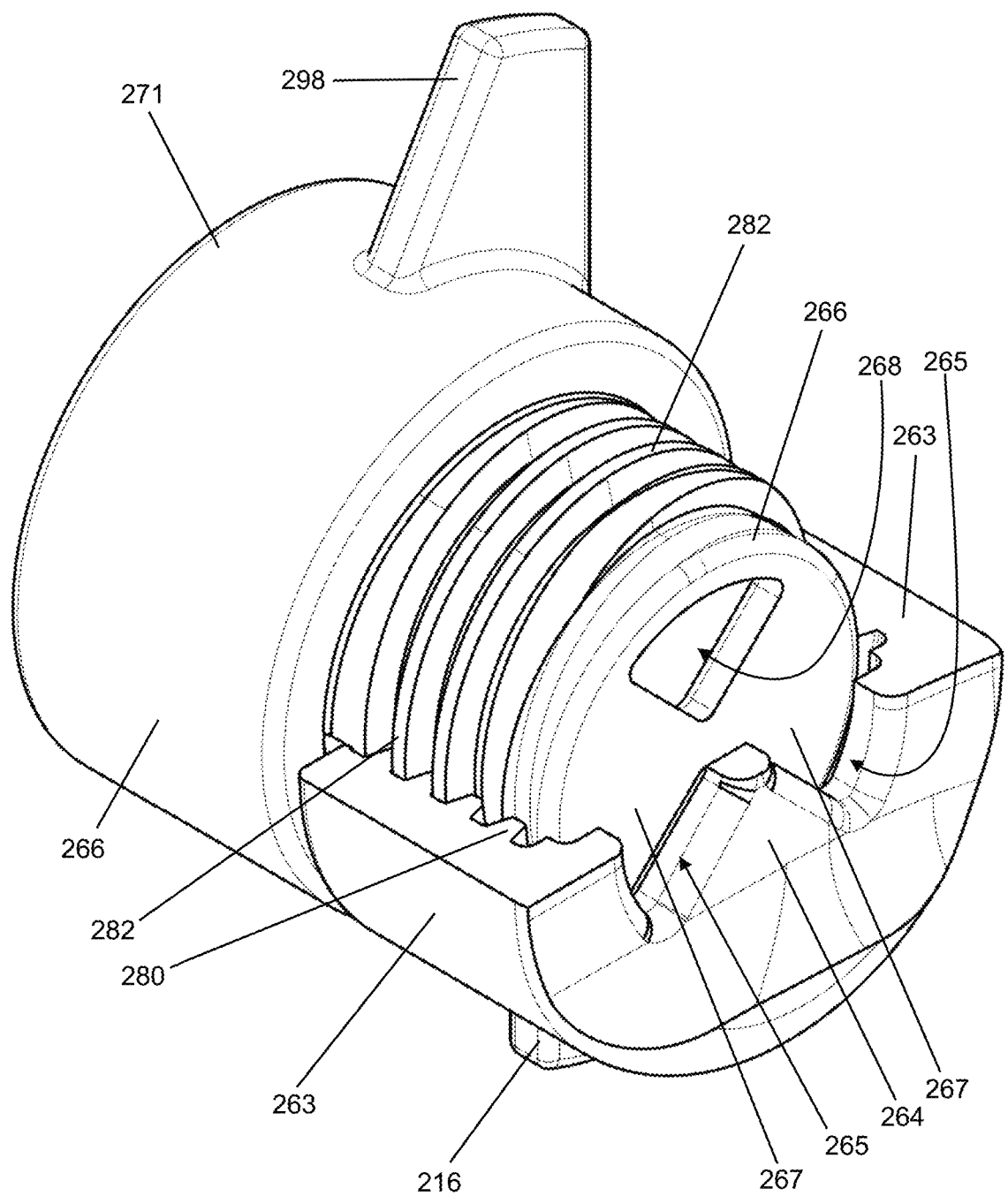
FIG. 27 shows a schematic perspective partial cross-sectional view of the valve according to FIGS. 23 to 26 in the closed state.
Figure 28:
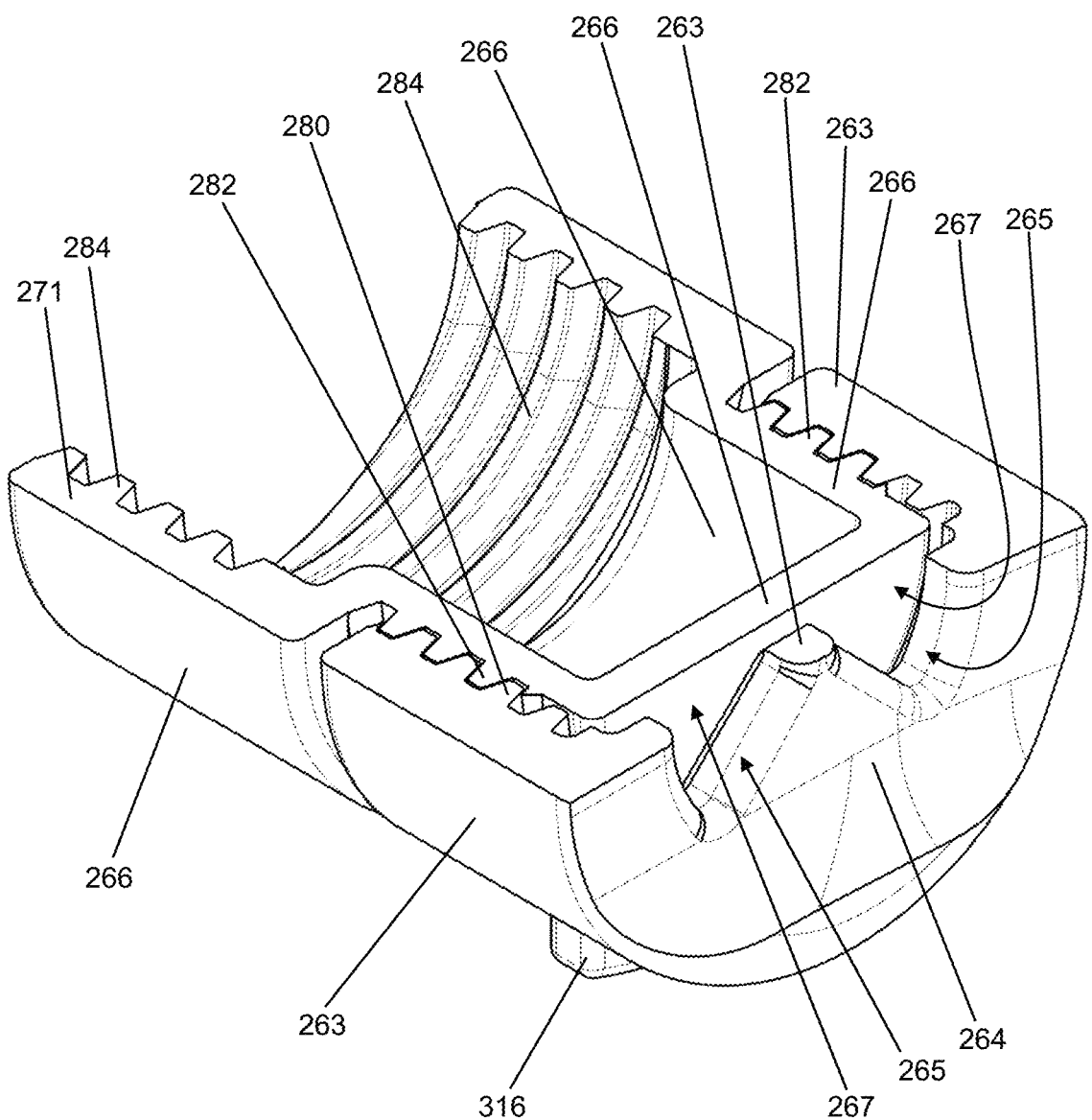
FIG. 28 shows a schematic perspective cross-sectional view of the valve according to FIGS. 23 to 27 in the closed state.
Figure 29:
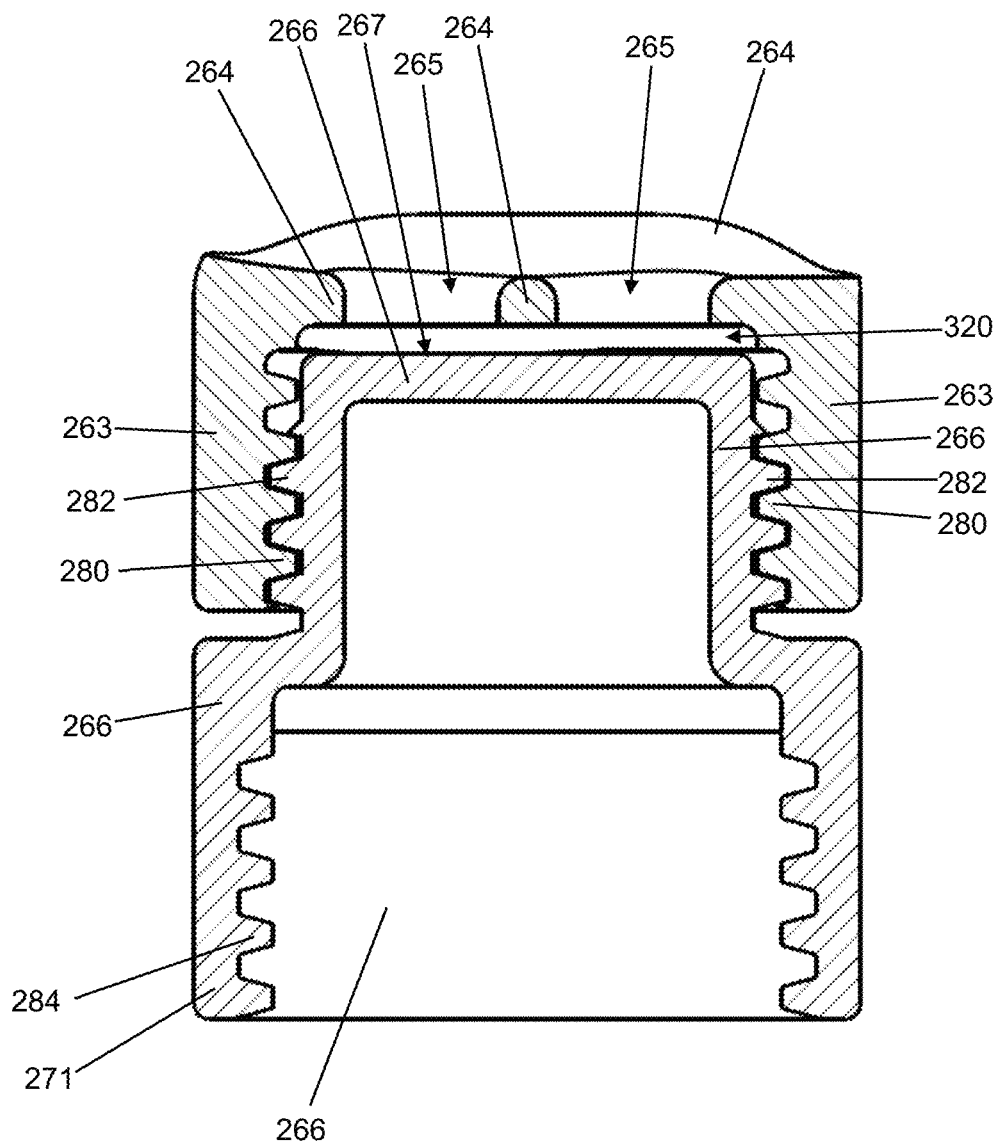
FIG. 29 shows a schematic cross-sectional view of the valve according to FIGS. 22 to 27 in the closed state.

FIGS. 17 to 21 are drawings of a third exemplary embodiment of a device according to the invention for producing a knee spacer component 210 in the form of a tibial component for a knee spacer and parts of the device, in various views. FIG. 22 shows the knee spacer component 210 and removed excess bone cement 217 which has been produced using such a third device according to the invention as the result of a method according to the invention, the method steps of which are shown chronologically in FIGS. 13 to 16.

The third device according to the invention is suitable and provided for producing a tibial component of a knee spacer. The device comprises a casting mold which is composed of two parts. The casting mold may have a trough-shaped mold 161 and a punch 162. The punch 162 can be inserted into the trough-shaped mold 161 and can be pushed into the trough-shaped mold 161 and preferably also withdrawn again. The trough-shaped mold 161 can be inexpensively fabricated from plastics film. The plastics film may have a plurality of layers. An opening for throughflow of bone cement paste (not shown), which may be delimited by a cylindrical wall of the punch 162, may be formed on one side of the punch 162. A valve seat 163 may be arranged in this opening. The valve seat 163 may be firmly connected to the punch 162 of the casting mold or even be formed as one part, as shown in FIGS. 17 to 21.

The valve seat 163 may take the form of a hollow cylinder which, apart from two first feed-throughs 165, is closed on a head side 164 oriented in the direction of the opening in the punch 162. The two first feed-throughs 165 may be quadrant-shaped and may preferably be arranged rotated or offset relative to one another by 180° with regard to the cylinder axis of the valve seat 163.

A valve body 178 may be or have been arranged in the interior of the valve seat 163 so as to be axially rotatable relative to the valve seat 163. The valve body 178 may have a sealing face 167 or surface oriented in the direction of the head side 164 of the valve seat 163, which sealing face may be suitable for closing the two first feed-throughs 165.

Two second feed-throughs 168 may be arranged in the valve body 178. The two second feed-throughs 168 may, similarly to the first feed-throughs 165, be quadrant-shaped and may preferably be arranged rotated relative to one another by 180° with regard to the cylinder axis of the valve body 178. The valve seat 163 and valve body 178 together form a valve of the device.

The device may have a handle 174 which forms a handgrip 176 at one end (see FIGS. 17 to 21). The valve body 178 with an outer thread 179 may be arranged at the opposite end of the handle 174. The valve body 178 may be or have been arranged in the valve seat 163 so as to be axially rotatable relative to the valve seat 163 by means of the handle 174 (see FIGS. 18 to 21). The valve body 178 may be screwed or put into the valve seat 163.

The handle 174 may have a hollow interior. The cavity in the interior of the handle 174 may be connected to the two second feed-throughs 168 of the handle 174. As a result, the cavity in the interior of the handle may form a collecting vessel for receiving excess bone cement 217, wherein the excess bone cement paste from the casting mold can flow through the two second feed-throughs 168 into the collecting vessel when the valve formed by the valve body 178 and the valve seat 163 is in an open position in which the two first feed-throughs 165 in the valve seat 163 are connected liquid-permeably for the bone cement paste to the two second feed-throughs 168 or are arranged above one another.

The punch 162 can be pushed into the trough-shaped mold 161. The casting mold can be closed to the outside by putting the punch 162 into the trough-shaped mold 161. When the trough-shaped mold 161 and the punch 162 are nested in one another, a gap may be present for venting the interior of the casting mold (not visible in FIGS. 17 to 21). Air or gas can escape through the gap from the interior of the closed casting mold when a bone cement paste is filled into the casting mold.

The valve seat 163 may have an inner thread 180 on its inside. The outer thread 179 of the handle 174 matches the inner thread 180 of the valve seat 163, such that the valve body 178 can be screwed into the valve seat 163.

The first feed-throughs 165 and the second feed-throughs 168 may be brought into overlap with one another by screwing the valve body 178 into the valve seat 163 until the limit stop is reached. The valve is then in the open state. In this open state, a bone cement paste may flow through the first feed-throughs 165 and through the second feed-throughs 168 out of the casting mold into the collecting vessel in the handle 174.

By making a quarter rotation (by 90°) of the valve body 178 relative to the valve seat 163, i.e. by unscrewing the valve body 178 from the valve seat 163, the first feed-throughs 165 and the second feed-throughs 168 may be offset relative to one another, such that the sealing face 167 of the valve body 178 covers the first feed-throughs 165 of the valve seat 163 and the closed regions of the head side 164 of the valve seat 163 cover the second feed-throughs 168 of the valve body 178. The valve is then in the closed state. Due to the small stroke of the valve body 178 relative to the valve seat 163 in the event of a quarter rotation, the gap arising between the valve body 178 and the valve seat 163 is so narrow (less than 1 mm wide) that a bone cement paste of a normal, let alone high, viscosity, is incapable of passing through the gap. This is particularly the case because the bone cement paste is deflected from its actual direction of flow by 90° in the gap.

The inner thread 180 of the valve seat 163 and the outer thread 179 of the valve body 178 may all have the same direction of rotation, i.e. all these threads are right-hand threads or left-hand threads. As a result, the valve may be opened by screwing the handle 174 into the valve seat 163. At the same time, the valve body 178 provides a seal relative to the valve seat 163.

The casting mold may have a bottom plate 192 for molding a sliding surface of a knee spacer component 210 molded with the casting mold. In the present case, this may be a sliding surface 212 of a tibial plateau of a tibial component (see FIG. 22). The knee spacer component 210 may additionally have a stem 214 and, on the stem 214, a piece of flash 216. The bottom plate 192 may form the base or bottom of the trough-shaped mold 161. The punch 162 can be pushed into the trough-shaped mold 161 in the direction of the bottom plate 192. As a result, a bone cement paste filled into the casting mold can be pressed against the bottom plate 192 of the trough-shaped mold 161. The casting mold and in particular the punch 162 of the casting mold may further have a stem molding 194 for forming the stem 214 of the knee spacer component 210.

The course of a method according to the invention is explained below with reference to FIGS. 17 to 22 on the basis of the third device according to the invention. A bone cement paste is filled into the trough-shaped mold 161.

Figure 18:
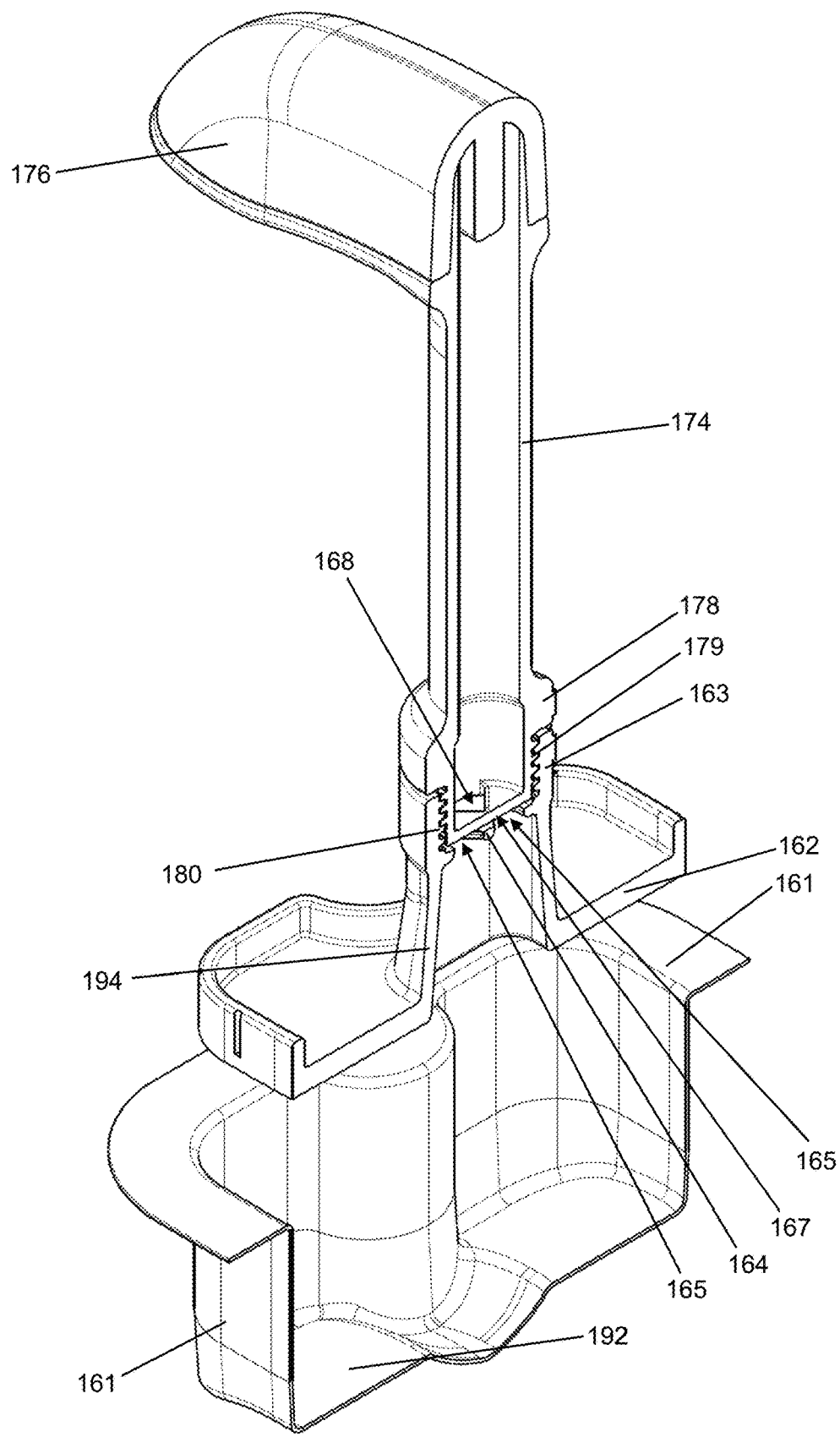
FIG. 18 shows a schematic perspective cross-sectional view of the third device according to the invention with the valve closed.
Figure 19:
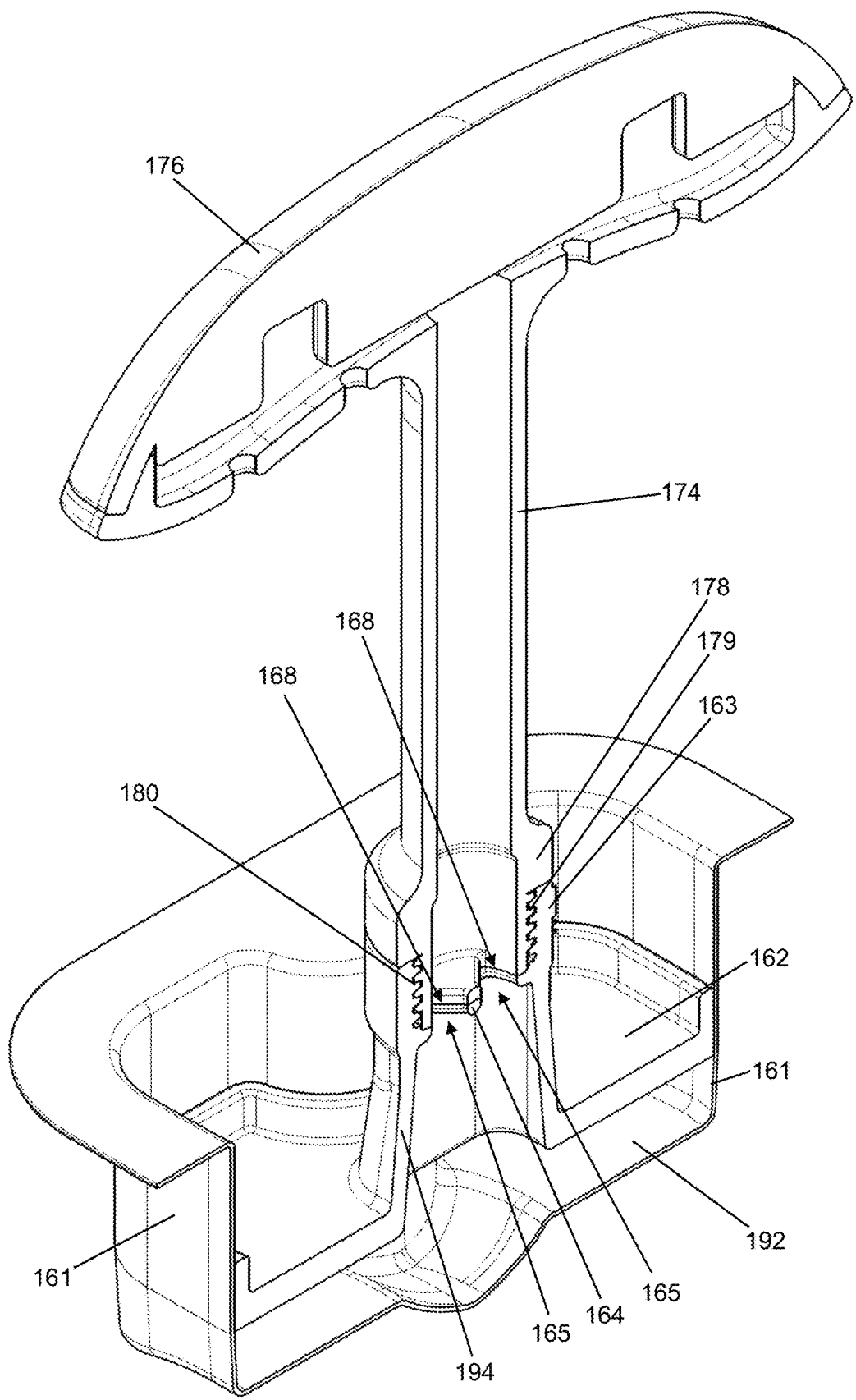

The handle 174 may now be screwed into the inner thread 180 of the valve seat 163 to adjust the desired height of the knee spacer component 210 to be produced. The valve body 178 here forms a valve with the valve seat 163. FIG. 18 shows this situation. The valve is brought into the open position by screwing the handle 174 in until the limit stop is reached (see FIG. 19).

Figure 20:
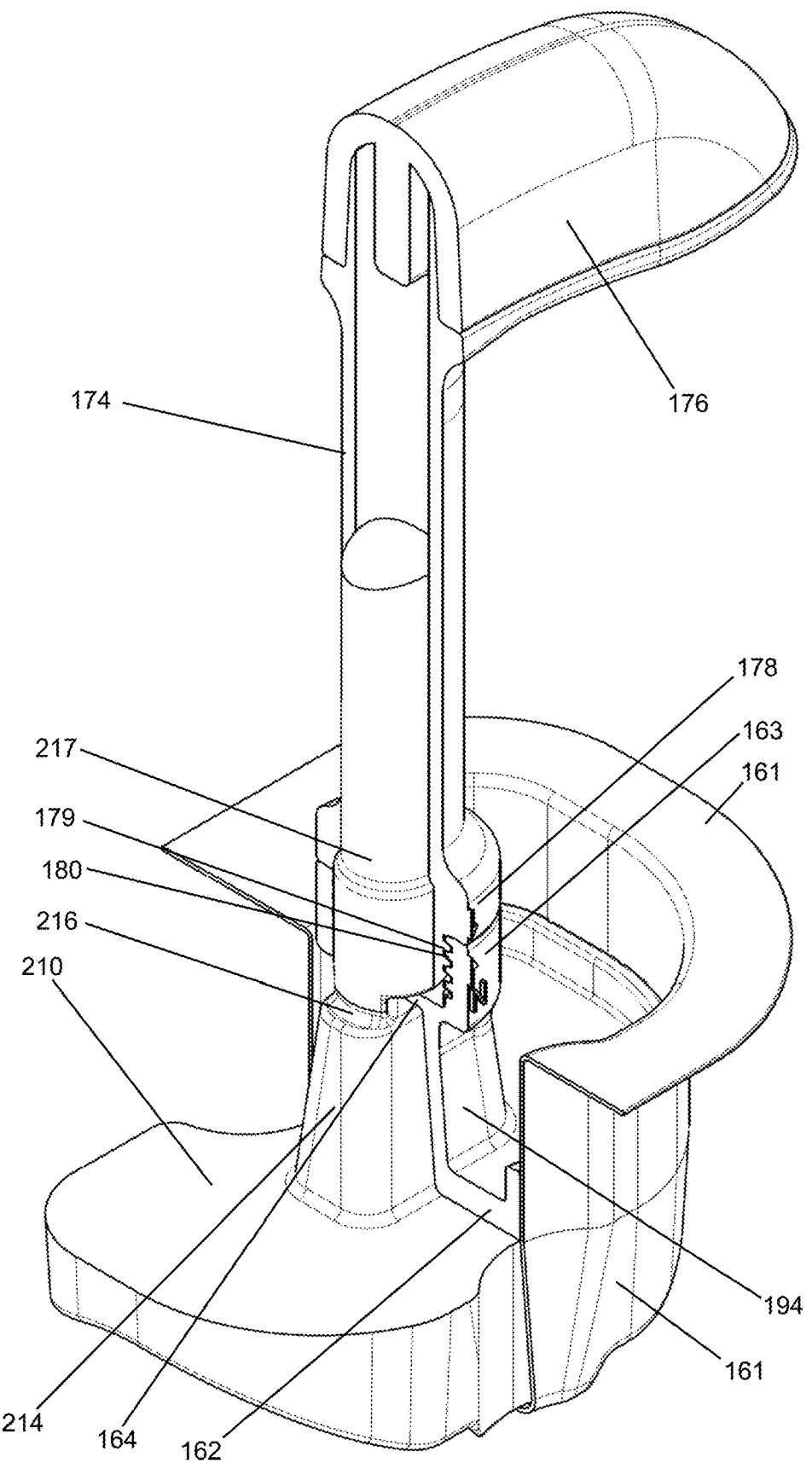
FIG. 20 shows a schematic perspective cross-sectional view of the third device according to the invention according to FIGS. 17 to 19 during forming of a tibial component.
Figure 21:
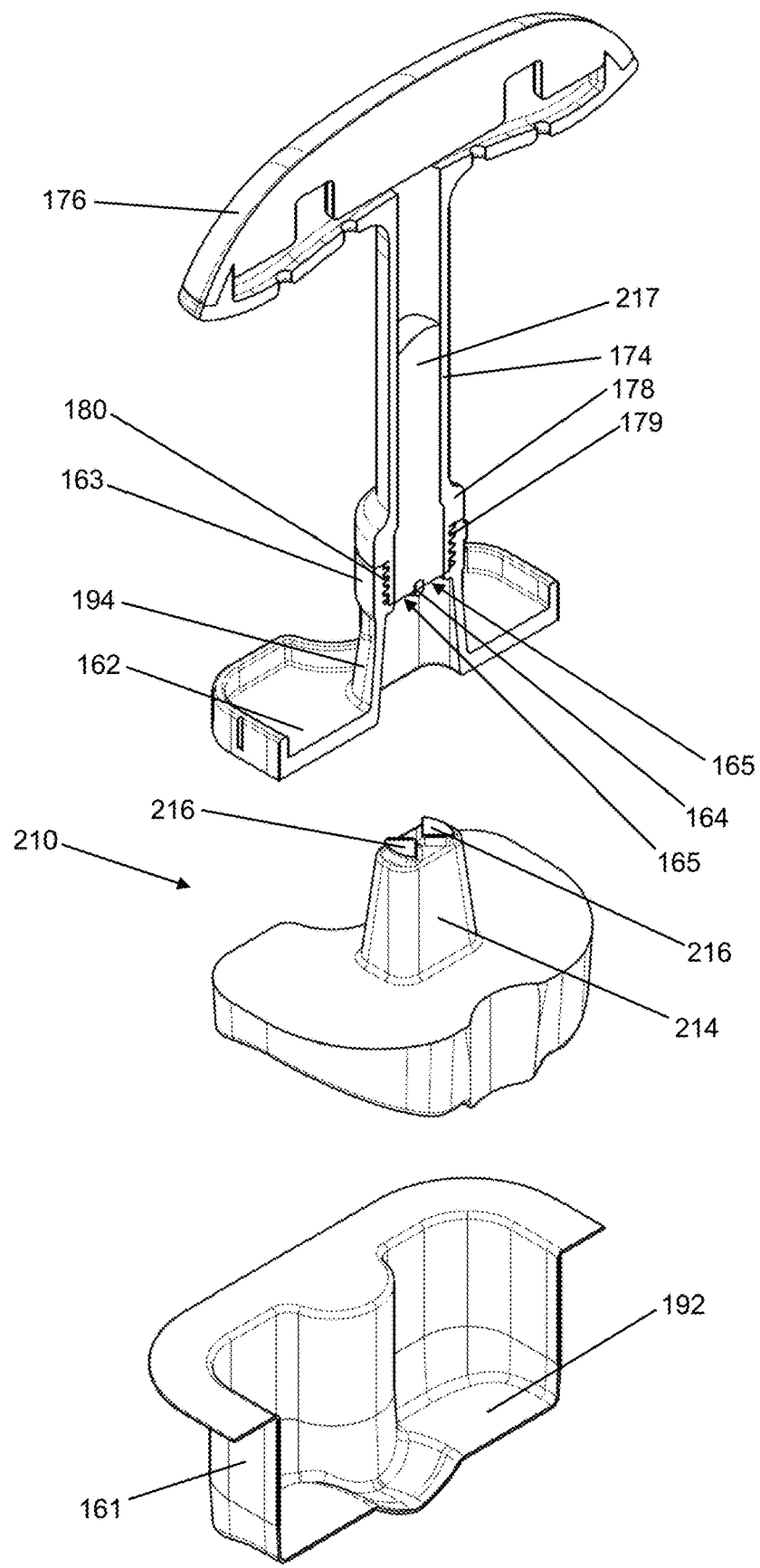
FIG. 21 shows a schematic perspective cross-sectional view of the third device according to the invention according to FIGS. 17 to 20 after forming of the tibial component.

Due to a reduction in the height of the interior of the casting mold by pushing the punch 162 into the trough-shaped mold 161, part of the bone cement paste is expelled from the casting mold and through the two first feed-throughs 165 and the two second feed-throughs 168 into the collecting vessel of the handle 174. This is shown in FIG. 20. The handle 174 is then rotated by a quarter rotation (by 90°) and thus the two second openings 168 are rotated relative to the two first openings 165, so closing the valve. In so doing, the bone cement paste is sheared off or largely sheared off in the valve. In this way, the excess bone cement 217 held in the collecting vessel of the handle 174 may be removed from the knee spacer component 210 or from the bone cement paste forming the knee spacer component 210 in the casting mold.

In this state, the bone cement paste can be cured in the casting mold. The knee spacer component 210 molded in this manner is then removed from the casting mold (see FIG. 22). Any flash 216 caused by the valve seat 163 and the first passages 165 can be cut off and removed. The surface of the knee spacer component 210 can be polished and/or coated, for example with antibiotics.

Instead of a casting mold for molding a tibial component, it is also straightforwardly possible to use a casting mold for molding a femoral component.

FIGS. 23 to 29 show a valve for a device according to the invention for producing a knee spacer in the open position (FIGS. 23 to 25) and in the closed position (FIGS. 26 to 29). The valve corresponds to the valves of the first device according to the invention according to FIGS. 1 to 10, of the second device according to the invention according to FIGS. 11 to 15 and of the third device according to the invention according to FIGS. 17 to 21, but may also be used with other casting molds to produce other knee spacers and knee spacer components.

The valve has a valve seat 263 which may be arranged in a casting mold (not shown) or have been made in one piece with a casting mold (not shown). The valve seat 263 may, however, also have been firmly connected to a part of the casting mold in another manner or also have been made in one piece with the casting mold or a part of the casting mold.

The valve seat 263 may take the form of a hollow cylinder which, apart from two first feed-throughs 265, is closed on a head side 264. The two first feed-throughs 265 may be quadrant-shaped and may preferably be arranged rotated relative to one another by 180° with regard to the cylinder axis of the valve seat 263. A valve body 266 may be arranged in the interior of the valve seat 263 so as to be axially rotatable relative to the valve seat 263. The valve body 266 may have a sealing face 267 or surface oriented in the direction of the head side 264 of the valve seat 263. The valve body 266 may be constructed as a stepped hollow cylinder, the front part of which can be screwed or put into the valve seat 263.

Two second feed-throughs 268 may be arranged in the sealing face 267. The two second feed-throughs 268 may, similarly to the first feed-throughs 265, be quadrant-shaped and may preferably be arranged rotated or offset relative to one another by 180° with regard to the cylinder axis of the valve body 266. The valve seat 263 and valve body 266 together form the valve of a device according to the invention. A handle (not shown) or an adapter element (not shown) for liquid-tight connection of a bone cement cartridge (not shown) may be screwed into the valve body 266. The valve body 266 may on its open side, which is remote from the sealing face 267, be formed as a port 271 for connecting the handle or an adapter element.

The valve seat 263 may have an inner thread 280 on its inside. On the front half of the valve body 266 facing the sealing face 267, the valve body 266 may have on the outside thereof an outer thread 282 matching the inner thread 280 of the valve seat 263. The valve body 266 may be screwed with its outer thread 282 into the inner thread 280 of the valve seat 263.

The first feed-throughs 265 and the second feed-throughs 268 may be brought into overlap with one another by screwing the valve body 266 into the valve seat 263 until the limit stop is reached. The valve is then in the open state. In this open state (see FIGS. 23 to 25), a bone cement paste may flow through the first feed-throughs 265 and through the second feed-throughs 268. By making a quarter rotation (by 90°) of the valve body 266 relative to the valve seat 263, i.e. by unscrewing the valve body 266 from the valve seat 263, the first feed-throughs 265 and the second feed-throughs 268 may be offset relative to one another, such that the sealing face 267 of the valve body 266 covers the first feed-throughs 265 of the valve seat 263 and the closed regions of the head side 264 of the valve seat 263 cover the second feed-throughs 268 of the valve body 266. The valve is then in the closed state (see FIGS. 26 to 29). Due to the small stroke of the valve body 266 relative to the valve seat 263 in the event of a quarter rotation, the gap 320 arising between the valve body 266 and the valve seat 263 is so narrow (less than 1 mm wide) that a bone cement paste of a normal, let alone high, viscosity, is incapable of passing through the gap 320 (see FIG. 29). This is particularly the case because the bone cement paste is deflected from its actual direction of flow by 90° in the gap 320.

The reverse side of the valve body 266 may have an inner thread 284 arranged in the port 271. A handle (not shown) or an adapter element (not shown) may accordingly be screwed into the port 271 of the valve body 266. The inner thread 280 of the valve seat 263, the outer thread 282 of the valve body 266 and the inner thread 284 of the valve body 266 may all have the same direction of rotation, i.e., all these threads are right-hand threads or left-hand threads. As a result, the valve can be opened by screwing a handle or an adapter element into the port 271 and continuing to rotate the handle or adapter element in the same direction. At the same time, the valve body 266 also provides a seal relative to the valve seat 263.

Furthermore, a grip 298 may be arranged on the valve body 266. The valve body 266 can be rotated in the valve seat 263 with the grip 298. As a result, the valve may be transferred manually from outside, with the assistance of the grip 298, from the open state into the closed state or from the closed state into the open state even if a bone cement cartridge is connected to the port 271.

Figure 33:
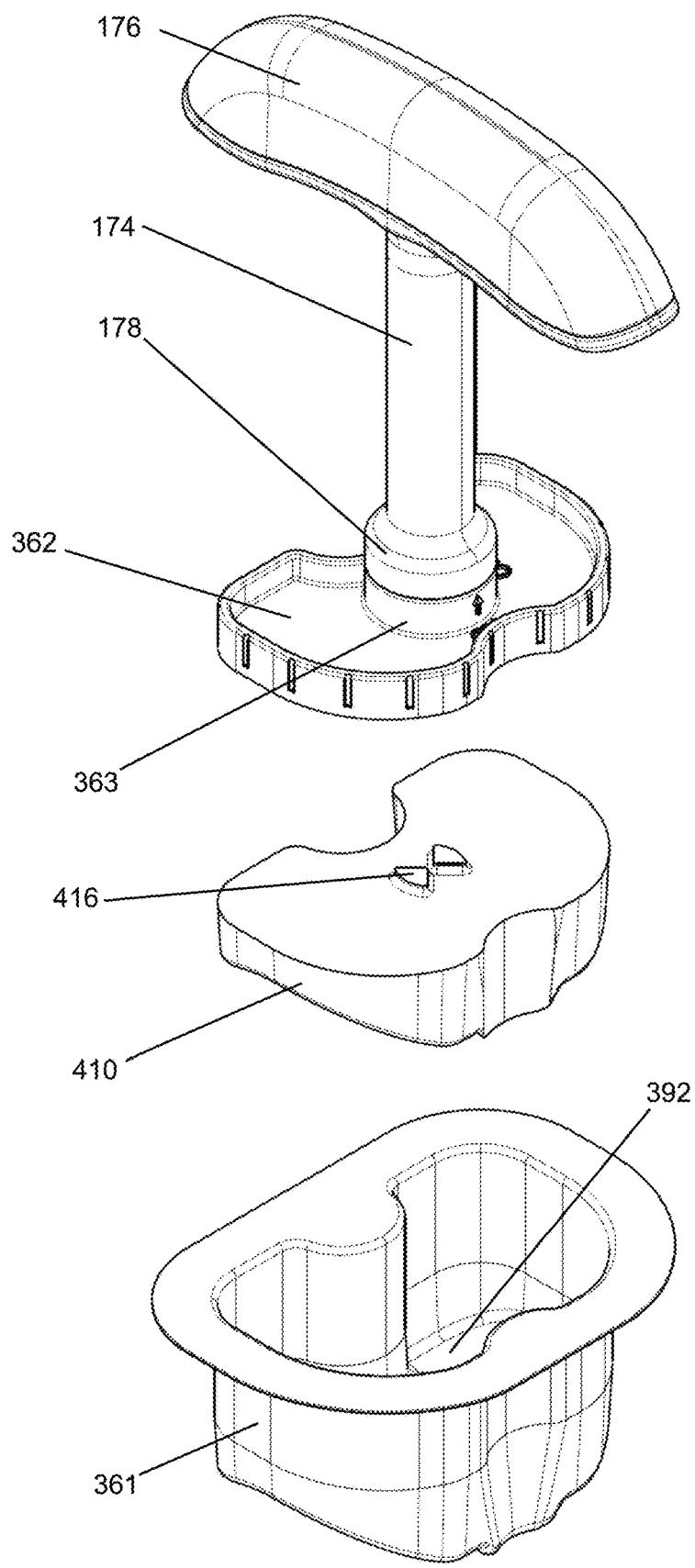
FIG. 33 shows a schematic perspective cross-sectional view of the fourth device according to the invention according to FIGS. 30 to 32 after forming of the tibial component.

FIGS. 30 to 33 are drawings of a fourth exemplary embodiment of a device according to the invention for producing a knee spacer component 410 in the form of a tibial component for a knee spacer and parts of the device, in various views. FIG. 33 shows inter alia the knee spacer component 410 which has been produced using such a fourth device according to the invention as the result of a method according to the invention, the method steps of which are shown chronologically in FIGS. 30 to 33.

The fourth device according to the invention is suitable and provided for producing a tibial component of a knee spacer. The device comprises a casting mold which is composed of two parts. The casting mold may have a trough-shaped mold 361 and a punch 362. The punch 362 can be inserted into the trough-shaped mold 361 and can be pushed into the trough-shaped mold 361 and preferably also withdrawn again. The trough-shaped mold 361 can be inexpensively fabricated from plastics film. The plastics film may have a plurality of layers. An opening for throughflow of bone cement paste (not shown), which may be delimited by a cylindrical wall of the punch 362, may be formed on one side of the punch 362. A valve seat 363 may be arranged in this opening. The valve seat 363 may be firmly connected to the punch 362 of the casting mold or even be formed as one part, as shown in FIGS. 30 to 33.

The valve seat 363 may take the form of a hollow cylinder which, apart from two first feed-throughs 365, is closed on a head side 364 oriented in the direction of the opening in the punch 362. The two first feed-throughs 365 may be quadrant-shaped and may preferably be arranged rotated or offset relative to one another by 180° with regard to the cylinder axis of the valve seat 363.

A valve body 178 may be or have been arranged in the interior of the valve seat 363 so as to be axially rotatable relative to the valve seat 363. The valve body 178 may have a sealing face 167 or surface oriented in the direction of the head side 364 of the valve seat 363, which sealing face may be suitable for closing the two first feed-throughs 365.

Two second feed-throughs 168 may be arranged in the valve body 178. The two second feed-throughs 168 may, similarly to the first feed-throughs 365, be quadrant-shaped and may preferably be arranged rotated relative to one another by 180° with regard to the cylinder axis of the valve body 178. The valve seat 363 and valve body 178 together form a valve of the device.

The device may have a handle 174 which forms a handgrip 176 at one end (see FIGS. 30 to 33). The handle 174 of the fourth exemplary embodiment according to FIGS. 30 to 33 is embodied identically to the handle 174 of the third exemplary embodiment according to FIGS. 17 to 21. The same reference signs have accordingly been used. The valve body 178 may have an outer thread 179 at the opposite end of the handle 174. The valve body 178 may be or have been arranged in the valve seat 363 so as to be axially rotatable relative to the valve seat 363 by means of the handle 174 (see FIGS. 31 and 32). The valve body 178 may be screwed or put into the valve seat 363.

The handle 174 may have a hollow interior. The cavity in the interior of the handle 174 may be connected to the two second feed-throughs 168 of the handle 174. As a result, the cavity in the interior of the handle may form a collecting vessel for receiving excess bone cement, wherein the excess bone cement paste from the casting mold can flow through the two second feed-throughs 168 into the collecting vessel when the valve formed by the valve body 178 and the valve seat 363 is in an open position in which the two first feed-throughs 365 in the valve seat 363 are connected liquid-permeably for the bone cement paste to the two second feed-throughs 168 or are arranged above one another.

The punch 362 can be pushed into the trough-shaped mold 361. The casting mold can be closed to the outside by putting the punch 362 into the trough-shaped mold 361. When the trough-shaped mold 361 and the punch 362 are nested in one another, a gap may be present for venting the interior of the casting mold (not visible in FIGS. 30 to 33). Air or gas can escape through the gap from the interior of the closed casting mold when a bone cement paste is filled into the casting mold.

The valve seat 363 may have an inner thread 380 on its inside. The outer thread 179 of the handle 174 matches the inner thread 380 of the valve seat 363, such that the valve body 178 can be screwed into the valve seat 363.

The first feed-throughs 365 and the second feed-throughs 168 may be brought into overlap with one another by screwing the valve body 178 into the valve seat 363 until the limit stop is reached. The valve is then in the open state. In this open state, a bone cement paste may flow through the first feed-throughs 365 and through the second feed-throughs 168 out of the casting mold into the collecting vessel in the handle 174.

By making a quarter rotation (by 90°) of the valve body 178 relative to the valve seat 363, i.e. by unscrewing the valve body 178 from the valve seat 363, the first feed-throughs 365 and the second feed-throughs 168 may be offset relative to one another, such that the sealing face 167 of the valve body 178 covers the first feed-throughs 365 of the valve seat 363 and the closed regions of the head side 364 of the valve seat 363 cover the second feed-throughs 168 of the valve body 178. The valve is then in the closed state. Due to the small stroke of the valve body 178 relative to the valve seat 363 in the event of a quarter rotation, the gap arising between the valve body 178 and the valve seat 363 is so narrow (less than 1 mm wide) that a bone cement paste of a normal, let alone high, viscosity, is incapable of passing through the gap. This is particularly the case because the bone cement paste is deflected from its actual direction of flow by 90° in the gap.

The inner thread 380 of the valve seat 363 and the outer thread 179 of the valve body 178 may all have the same direction of rotation, i.e. all these threads are right-hand threads or left-hand threads. As a result, the valve may be opened by screwing the handle 174 into the valve seat 363. At the same time, the valve body 178 provides a seal relative to the valve seat 363.

The casting mold may have a bottom plate 392 for molding a sliding surface of a knee spacer component 410 molded with the casting mold. In the present case, this may be a sliding surface of a tibial plateau of a tibial component (see FIG. 33). The knee spacer component 410 may have a piece of flash 416. In contrast with the other exemplary embodiments 1 to 3, the knee spacer component 410 according to the fourth exemplary embodiment has no stem. The bottom plate 392 may form the base or bottom of the trough-shaped mold 361. The punch 362 can be pushed into the trough-shaped mold 361 in the direction of the bottom plate 392. As a result, a bone cement paste filled into the casting mold can be pressed against the bottom plate 392 of the trough-shaped mold 361.

A method according to the invention proceeds similarly to the exemplarily described methods of exemplary embodiments two and three.

Figure 30:
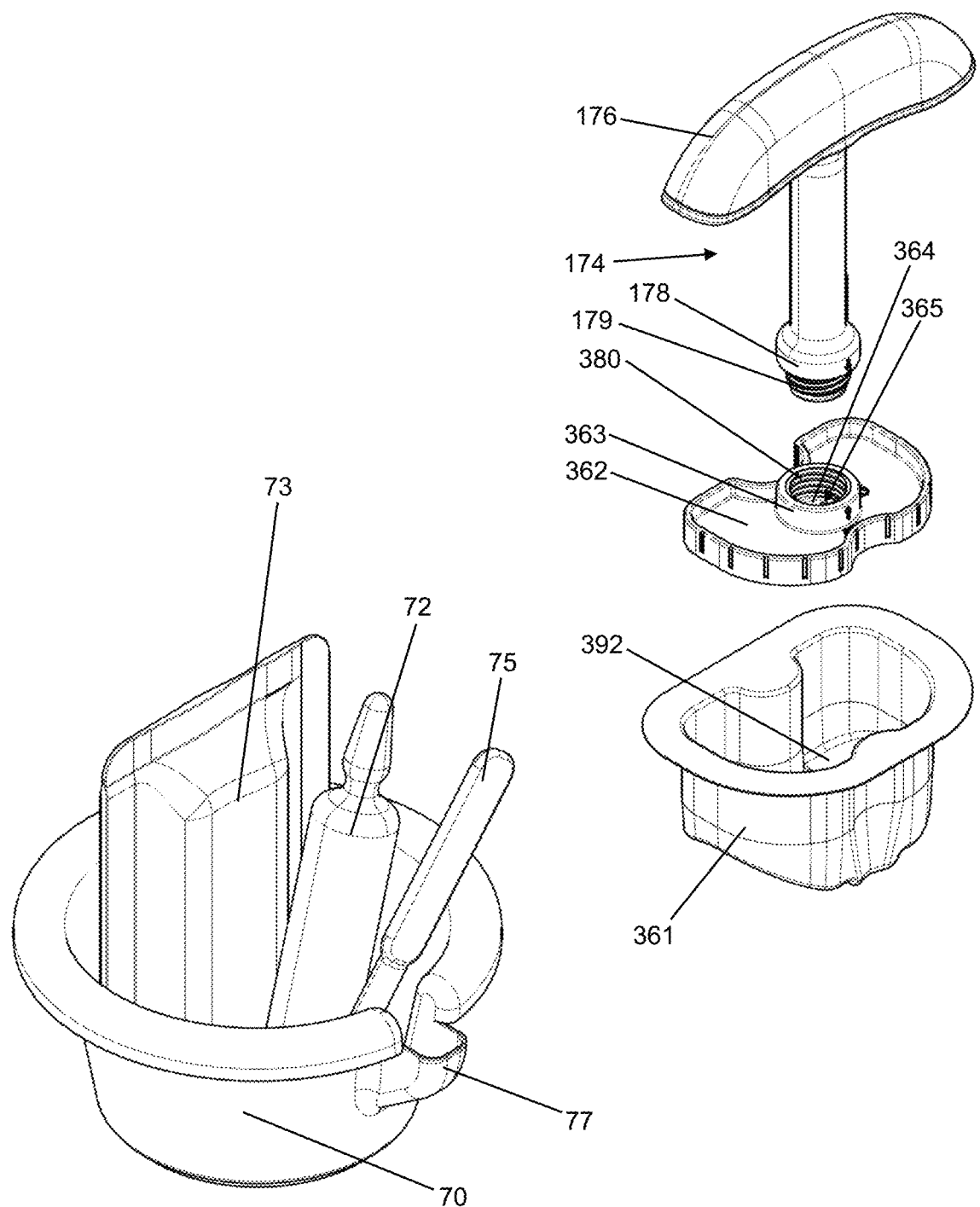
FIG. 30 shows a schematic perspective external view of a fourth exemplary device according to the invention for producing a tibial component.
Figure 31:
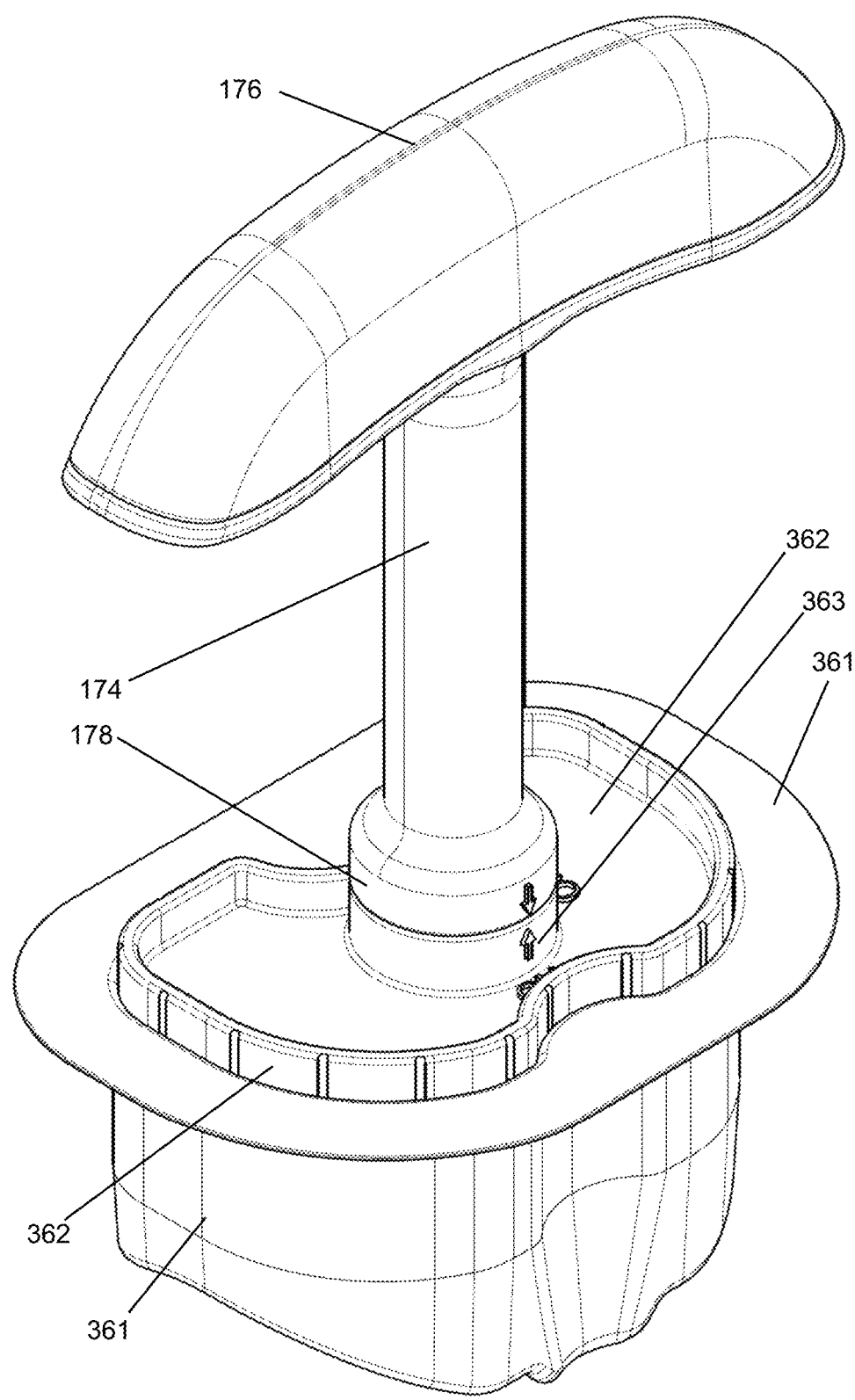
FIG. 31 shows a schematic perspective external view of the fourth device according to the invention with inserted punch.
Figure 32:
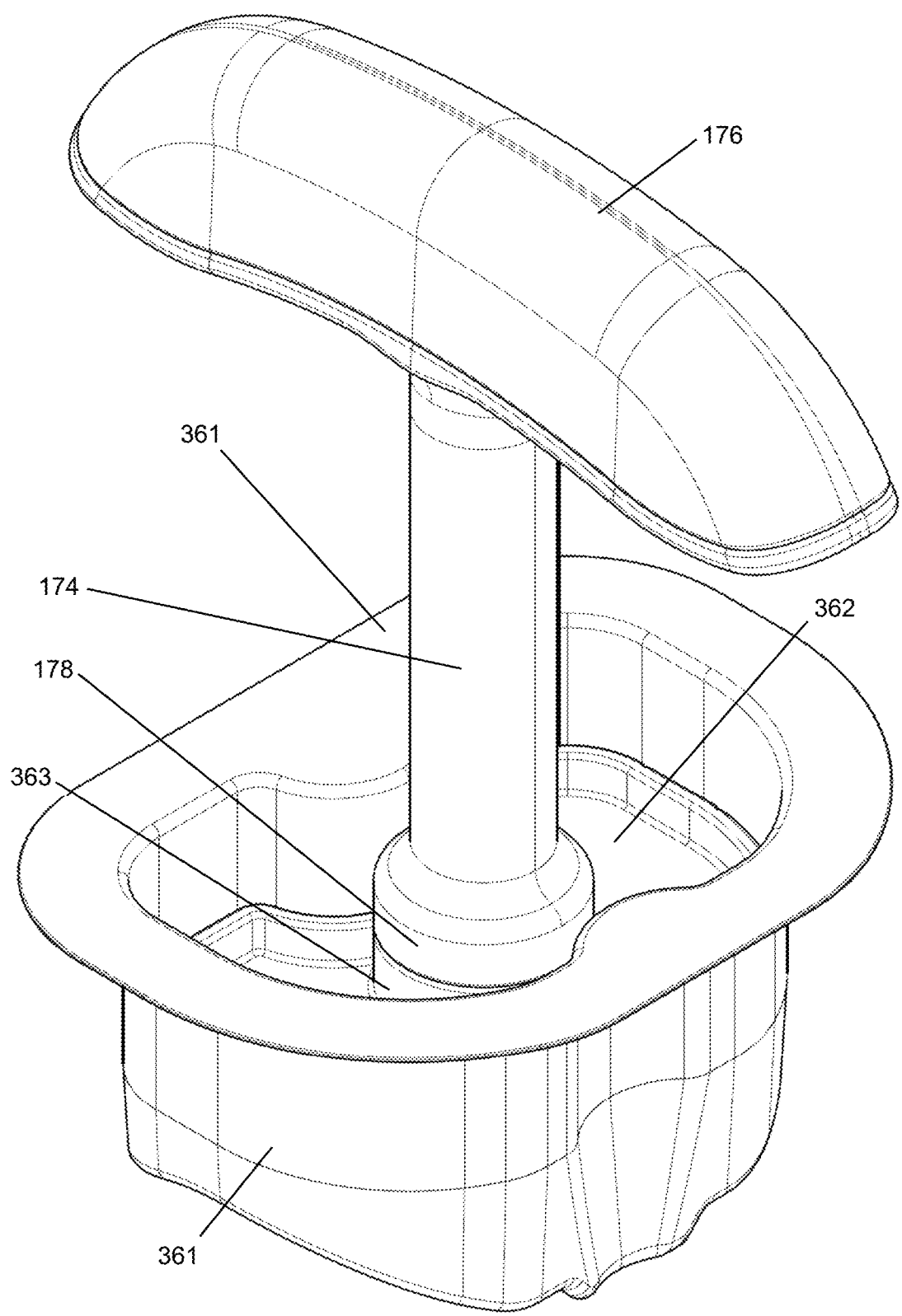

The bone cement paste may here be mixed in a mixing cup 70 (see FIG. 30). The device may to this end have a monomer liquid container 72 containing monomer liquid and a bone cement powder container 73 containing bone cement powder. The bone cement paste may be mixed in the mixing cup 70 from the bone cement powder and the monomer liquid. The device may have a spatula 75 or another mixing tool for mixing the bone cement paste in the mixing cup 70. The monomer liquid container 72 may be a glass ampoule. The mixing cup 70 may have a spout 77 for pouring out the bone cement paste. The mixed bone cement paste may be filled from the mixing cup 70 via the spout 77 of the mixing cup 70 into the trough-shaped mold 361.

Alternatively, a bone cement cartridge may also be used for producing and filling a bone cement paste into the trough-shaped mold 361 or into the casting mold in a similar manner to the first exemplary embodiment according to FIGS. 1 to 10.

Instead of a casting mold for molding a tibial component, it is also straightforwardly possible to use a casting mold for molding a femoral component.

The features of the invention disclosed in the preceding description, as well as in the claims, figures and exemplary embodiments, may be essential both individually and in any combination for realizing the invention in its various embodiments.

LIST OF REFERENCE NUMERALS 1, 61, 161, 361 Trough-shaped mold/casting mold
2, 62, 162, 362 Punch/casting mold
3, 63, 163, 263, 363 Valve seat
4, 64, 164, 264, 364 Head side
5, 65, 165, 265, 365 Feed-through
6, 266 Valve body
7, 67, 167, 267 Sealing face
8, 68, 168, 268 Feed-through
9 Adapter element
10 Bone cement cartridge
11, 271 Port
12 Delivery opening
13 Delivery tube
14, 74, 174 Handle
15 Mixer
16, 76, 176 Handgrip
17 Seal
18, 78, 178 Valve body
19, 79, 179 Outer thread
20, 80, 180, 280, 380 Inner thread
21 Feed-through
22, 182, 282 Outer thread
24, 184, 284 Inner thread
26 Outer thread
28 Latching means
30 Mating latch
32, 92, 192, 392 Bottom plate for molding a sliding surface
34, 94, 194 Stem molding
38, 298 Grip
44 Vacuum port
46 Piston
48 Seal
50, 51 Bone cement paste
52 Porous disk
54 Seal
70 Mixing cup
72 Monomer liquid container
73 Bone cement powder container
75 Spatula
77 Spout
82 Closing pin
110 Knee spacer component/femoral component
112, 212 Sliding surface
114, 214 Stem
116, 216, 416 Flash
117, 217 Excess bone cement
210, 410 Knee spacer component/tibial component
316 Projection
320 Gap

The invention claimed is:

1. A device for producing a knee spacer component by curing bone cement paste, wherein the knee spacer component is provided in a medical field for replacing part of a knee joint comprising an articulating surface of the knee joint, the device having
a casting mold for molding the knee spacer component from a bone cement paste;
a valve seat which is connected to the casting mold, wherein the valve seat has a closed head side with at least one first feed-through, wherein the at least one first feed-through opens into the casting mold;
a valve body which is mounted so as to be rotatable relative to the valve seat and which has a sealing face, wherein the sealing face is oriented in a direction of the closed head side of the valve seat, wherein at least one second feed-through is arranged in the sealing face;
wherein the valve seat and the valve body together form a valve, wherein the valve is reversibly transferable into an open position and a closed position by rotation of the valve body relative to the valve seat, wherein, in the open position of the valve, the at least one first feed-through of the valve seat and the at least one second feed-through of the valve body are located above one another and provide a connection through the valve which is permeable to the bone cement paste, wherein, in the closed position of the valve, the at least one first feed-through of the valve seat is covered by the sealing face of the valve body, wherein, in the closed position of the valve, the casting mold is closed in liquid-tight manner for the bone cement paste;
wherein the valve body is mounted so as to be rotatable about an axis of rotation relative to the valve seat, and wherein the axis of rotation extends along an axis of rotational symmetry of the sealing face of the valve body.

2. The device according to claim 1, characterized in that the valve seat is connected to the casting mold so as not to be rotatable relative to the casting mold, and the valve seat is connected fixedly and/or rigidly to the casting mold or is formed as one part with the casting mold.

3. The device according to claim 1, characterized in that the valve is manually operable from outside the device, wherein the valve body is manually rotatable relative to the valve seat and the valve is transferable by rotation from the closed position into the open position and from the open position into the closed position.

4. The device according to claim 1, characterized in that, in the closed position of the valve, the at least one first feed-through of the valve seat is covered by the sealing face of the valve body, wherein the closed head side of the valve seat and the sealing face of the valve body are spaced apart from one another by a maximum of 2 mm.

5. The device according to claim 1, characterized in that the valve body has a port for liquid-tight connection of a bone cement cartridge or for liquid-tight connection of a handle of the device or is firmly connected to such a port.

6. The device according to claim 5, characterized in that the device has an adapter element which is connected or connectable to the bone cement cartridge, wherein the adapter element is detachably and interlockingly connected or connectable to the port, such that an interior of the bone cement cartridge is connected or connectable permeably for the bone cement paste via the adapter element to the at least one second feed-through in the valve body, and/or;
the port comprises, for liquid-tight connection of the bone cement cartridge or the handle, an inner thread in the valve body or an outer thread on the valve body, wherein a counter adapter element of the bone cement cartridge has a mating thread matching the inner thread or the outer thread, or the handle of the device has a mating thread matching the inner thread or the outer thread.

7. The device according to claim 1, characterized in that the device has a bone cement cartridge for mixing bone cement starting components and for delivering mixed bone cement paste from the bone cement cartridge or the device has a bone cement cartridge for mixing polymethyl methacrylate bone cement starting components and for delivering mixed polymethyl methacrylate bone cement paste from the bone cement cartridge, wherein the bone cement cartridge contains the bone cement starting components for producing the bone cement paste in mutually separate regions.

8. The device according to claim 1, characterized in that the device has a handle which is connectable to the valve body and with which the valve body is rotatable relative to the valve seat, wherein the handle has a cavity for receiving the bone cement paste, wherein the cavity is connected to the at least one second feed-through in liquid-permeable manner.

9. The device according to claim 1, characterized in that a sum of all free openings of the at least one first feed-through in the closed head side is at most as large as the closed surface of the head side and a sum of all free openings of the at least one second feed-through in the sealing face is at most as large as the closed surface of the sealing face.

10. The device according to claim 1, characterized in that the valve seat has an inner thread on an inside and the valve body has a matching outer thread on an outside, such that the valve body is able to be screwed into the valve seat.

11. The device according to claim 1, characterized in that the casting mold has a trough-shaped mold with a cavity and a punch, wherein the punch is insertable or inserted into the cavity of the trough-shaped mold and the punch is axially displaceable in the cavity, and wherein the trough-shaped mold has a cavity bottom, wherein the cavity bottom forms a contour of one or more articulating sliding surfaces of the knee spacer component.

12. The device according to claim 11, characterized in that the valve seat is arranged at an end of a portion of the punch which shapes a stem of the knee spacer component.

13. The device according to claim 1, characterized in that the at least one first feed-through in the closed head side has the same size and shape as the at least one second feed-through in the sealing face and/or
the at least one first feed-through in the closed head side is two first feed-throughs and the at least one second feed-through in the sealing face is two second feed-throughs, wherein the two first feed-throughs are arranged in the valve seat in quadrants arranged opposingly with regard to an axis of rotation of the valve body and the two second feed-throughs are arranged in the sealing face in quadrants arranged opposingly with regard to the axis of rotation of the valve body.

14. The device according to claim 1, characterized in that a collar is arranged on the sealing face of the valve body, which said collar on the sealing face of the valve body rests on an edge of the valve seat or a collar is arranged on the closed head side of the valve seat, which said collar on the closed head side of the valve seat rests on an edge of the valve body.

15. The device according to claim 1, characterized in that a handgrip is fastened or fastenable to the valve body, wherein the handgrip has at least one radial extent with regard to an axis of rotation of the valve body, wherein the handgrip is fastened or fastenable to an opposite side of the valve body from the sealing face, wherein the valve body may be rotated by a maximum of 90° relative to the valve seat.

16. The device according to claim 1, characterized in that the valve body and the valve seat are fabricated of a thermoplastic, wherein the valve seat is formed as one part with the casting mold.

17. The device according to claim 1, characterized in that a latch element is arranged on the sealing face of the valve body and a mating latch element is arranged on the head side of the valve seat wherein the latch element is able to be brought into engagement with the mating latch element, wherein the latch element is positioned on the valve body such that rotation or unscrewing of the valve body from the valve seat is limited to an angle of rotation of a maximum of 90° when the valve body is put into the valve seat.

18. The device according to claim 1, characterized in that the casting mold is in two parts or multiple parts, wherein a gap through which air or gas can escape from an interior of the casting mold is present between at least two of the parts of the assembled casting mold.

19. The device according to claim 1, characterized in that the device has a collecting vessel, wherein the valve is connected or connectable on a side remote from the casting mold to the collecting vessel for receiving excess bone cement paste which emerges from the casting mold through the valve in the open position or the valve is formed as one part with the collecting vessel.

20. A method for producing a knee spacer component for temporarily replacing part of a knee joint comprising an articulating surface of the knee joint, wherein the method is carried out with a device according to claim 1, the method having the following chronological steps:
  A) connecting a bone cement cartridge to the device in liquid-tight manner;
  B) injecting bone cement paste from the bone cement cartridge through the valve in the open position into the casting mold;
  C) rotating the valve body relative to the valve seat and so transferring the valve into the closed position and shearing off the bone cement paste at the at least one first feed-through in the closed head side of the valve seat by rotation of the valve body relative to the valve seat;
  D) detaching the bone cement cartridge from the casting mold;
  E) curing the bone cement paste in the casting mold; and
  F) removing the resultant molded and cured knee spacer component from the casting mold.

21. The method according to claim 20, characterized in that
  the following intermediate steps proceed after step D) and before step E):
  D2) connecting a new bone cement cartridge to the device in liquid-tight manner, wherein the bone cement paste or starting components for producing the bone cement paste is/are present in the new bone cement cartridge;
  D3) rotating the valve body relative to the valve seat and so transferring the valve into the open position;
  D4) injecting the bone cement paste from the new bone cement cartridge through the valve in the open position into the casting mold;
  D5) rotating the valve body relative to the valve seat and so transferring the valve into the closed position and shearing off the bone cement paste at the at least one first feed-through in the closed head side of the valve seat by rotation of the valve body relative to the valve seat; and
  D6) detaching the new bone cement cartridge from the casting mold;
  wherein steps D2) to D6) are repeated once or multiple times with in each case new bone cement cartridges which contain the bone cement paste or the starting components thereof until the casting mold is filled completely or as required with the bone cement paste.

22. The method according to claim 21, characterized in that, for liquid-tight connection of the bone cement cartridge and/or the new bone cement cartridge, said cartridge is connected to a port on the valve body of the device, wherein the bone cement cartridge or the new bone cement cartridge is rotated or screwed into the port and, for detaching the bone cement cartridge and/or the new bone cement cartridge from the port, the bone cement cartridge or the new bone cement cartridge is rotated out of or unscrewed from the port, and/or injection of the bone cement paste from the bone cement cartridge or the new bone cement cartridge proceeds by pushing a piston into an interior of the bone cement cartridge.

23. The method according to claim 20, characterized in that
  the casting mold has a trough-shaped mold and a punch, wherein, before step E), the punch is pressed into the trough-shaped mold and as a result the knee spacer component is molded from the bone cement paste in the casting mold, wherein, on pressing the punch into the trough-shaped mold, part of the bone cement paste is expelled from the casting mold through the valve in the open position and wherein the part of the bone cement paste which is pressed into a collecting vessel is that associated with the at least one second passage of the valve.

24. A method for producing a knee spacer component for temporarily replacing part of a knee joint comprising an articulating surface of the knee joint, wherein the method is carried out with a device according to claim 1, the method having the following chronological steps:
  A) producing a bone cement paste;
  B) filling a mixed bone cement paste into the casting mold;
  C) compressing the casting mold and so expelling part of the bone cement paste from the casting mold through the valve in the open position;
  D) rotating the valve body relative to the valve seat and so transferring the valve into the closed position and shearing off the bone cement paste at the at least one first feed-through in the closed head side of the valve seat by rotation of the valve body relative to the valve seat;
  E) curing the bone cement paste in the casting mold; and
  F) removing the resultant molded and cured knee spacer component from the casting mold.

25. The method according to claim 24, characterized in that
  a step B1) proceeds between steps B) and C):
  closing the casting mold apart from the valve.

26. The method according to claim 24, characterized in that,
  the casting mold has a trough-shaped mold and a punch, wherein, in step C), the punch is pressed into the trough-shaped mold and as a result the knee spacer component is molded from the bone cement paste in the casting mold, wherein, on pressing the punch into the trough-shaped mold, part of the bone cement paste is expelled from the casting mold through the valve in the open position.

27. The method according to claim 21, characterized in that the bone cement paste is mixed before step B) in the bone cement cartridge from a monomer liquid and a cement powder, wherein, optionally before step D3) and before step D2), the bone cement paste is mixed in the new bone cement cartridge from a monomer liquid and a cement powder.

28. The method according to claim 20, characterized in that
the valve body is rotated relative to the valve seat by screwing the valve body in the valve seat or by manually rotating the valve body relative to the valve seat, wherein manual turning proceeds by operation of a handgrip on the valve body.

29. The method according to claim 22, characterized in that the bone cement paste is mixed before step B) in the bone cement cartridge from a monomer liquid and a cement powder, wherein, optionally before step D3) and before step D2), the bone cement paste is mixed in the new bone cement cartridge from a monomer liquid and a cement powder.

30. The method according to claim 26, characterized in that
the valve body is rotated relative to the valve seat by screwing the valve body in the valve seat or by manually rotating the valve body relative to the valve seat, wherein manual turning proceeds by operation of a handgrip on the valve body.

* * * * *